(12) United States Patent
Tong et al.

(10) Patent No.: US 12,329,396 B2
(45) Date of Patent: Jun. 17, 2025

(54) KIDNEY STONE TREATMENT SYSTEM

(71) Applicant: CALYXO, INC., Pleasanton, CA (US)

(72) Inventors: Ling Tong, Pleasanton, CA (US); Calvin Lam, Pleasanton, CA (US); Kejin Wang, Pleasanton, CA (US); Joseph Catanese, III, Pleasanton, CA (US); Jee Shin, Pleasanton, CA (US); Alex Lim, Pleasanton, CA (US); Brian Y. Tachibana, Pleasanton, CA (US); Matthew Yurek, Pleasanton, CA (US); Caralin Riva Adair, Pleasanton, CA (US); Andrew J. Hudson, Pleasanton, CA (US); Andrew Johnston, Pleasanton, CA (US); Eddie Gonzalez, Pleasanton, CA (US); Ailee Pham, Pleasanton, CA (US)

(73) Assignee: CALYXO, INC., Pleasanton, CA (US)

( * ) Notice: Subject to any disclaimer, the term of this patent is extended or adjusted under 35 U.S.C. 154(b) by 0 days.

(21) Appl. No.: 18/278,081

(22) PCT Filed: Mar. 1, 2023

(86) PCT No.: PCT/US2023/014276
§ 371 (c)(1),
(2) Date: Aug. 21, 2023

(87) PCT Pub. No.: WO2023/167926
PCT Pub. Date: Sep. 7, 2023

(65) Prior Publication Data
US 2024/0032951 A1 Feb. 1, 2024

Related U.S. Application Data

(60) Provisional application No. 63/411,568, filed on Sep. 29, 2022, provisional application No. 63/357,468, (Continued)

(51) Int. Cl.
*A61B 17/22* (2006.01)
*A61B 18/26* (2006.01)
(Continued)

(52) U.S. Cl.
CPC .............. *A61B 17/22* (2013.01); *A61B 18/26* (2013.01); *A61M 1/741* (2021.05);
(Continued)

(58) Field of Classification Search
CPC .......... A61B 17/22; A61B 2017/22079; A61B 2217/2215; A61B 2217/2217; A61M 1/76;
(Continued)

(56) References Cited

U.S. PATENT DOCUMENTS 3,065,749 A 11/1962 Brass
3,438,607 A 4/1969 Williams et al.
(Continued)

FOREIGN PATENT DOCUMENTS

CN 203776869 U 8/2014
CN 203776946 U 8/2014
(Continued)

OTHER PUBLICATIONS

Non-final office action mailed Jan. 21, 2022 for U.S. Appl. No. 17/489,733; 6 pages.
(Continued)

*Primary Examiner* — Diane D Yabut
*Assistant Examiner* — Christian D Knauss
(74) *Attorney, Agent, or Firm* — Squire Patton Boggs (US) LLP

(57) ABSTRACT

Kidney stone removal system is disclosed having components including a handle mechanism, a nozzle tip, and a guiding device. The handle mechanism employs a trigger
(Continued)

that enables control of irrigation and vacuum/suction. Depression of a trigger in the trigger mechanism conveys status of vacuum/suction and irrigation to a user by providing increased resistance at different points of depression. When the trigger is in a home (undepressed) position, irrigation and vacuum/suction are turned off. When the trigger is in a fully depressed position, irrigation and vacuum/suction are turned on. When the trigger is in an intermediate position, irrigation may be turned on, while vacuum/suction remains turned off. The nozzle includes one or more irrigation ports positioned at a distal end of the nozzle and having an irrigation port departure angle of 30 to 60 degrees for directing irrigation fluid forward and laterally from the distal end of the nozzle. The guiding device is configured to be removably positioned in the nozzle for receiving a debris fragmentizing device, such as a laser device. The guiding device is configured to prevent an unintended movement of the fragmentizing device when the fragmentizing device is positioned in the nozzle while allowing fluid and debris to flow past the fragmentizing device and through a vacuum tube.

7 Claims, 60 Drawing Sheets

Related U.S. Application Data filed on Jun. 30, 2022, provisional application No. 63/315,815, filed on Mar. 2, 2022.

(51) Int. Cl.
*A61M 1/00* (2006.01)
*A61M 3/02* (2006.01)
*A61B 18/00* (2006.01)

(52) U.S. Cl.
CPC .............. *A61M 3/0233* (2013.01); *A61B 2017/22079* (2013.01); *A61B 2018/00196* (2013.01); *A61B 2018/00511* (2013.01); *A61B 2018/00744* (2013.01); *A61B 2018/0091* (2013.01); *A61B 2018/263* (2013.01); *A61B 2217/005* (2013.01); *A61B 2218/002* (2013.01); *A61B 2218/007* (2013.01); *A61M 2210/1082* (2013.01)

(58) Field of Classification Search
CPC ........ A61M 1/77; A61M 1/774; A61M 1/777; A61M 39/225
See application file for complete search history.

(56) References Cited

U.S. PATENT DOCUMENTS

| | | |
|---|---|---|
| 3,749,090 A | 7/1973 | Stewart |
| 3,830,240 A | 8/1974 | Antonevich et al. |
| 4,146,300 A | 3/1979 | Kaiser |
| 4,203,430 A | 5/1980 | Takahashi |
| 4,215,476 A | 8/1980 | Armstrong |
| 4,294,233 A | 10/1981 | Takahashi |
| 4,295,464 A | 10/1981 | Shihata |
| 4,393,872 A | 7/1983 | Reznik et al. |
| 4,418,688 A | 12/1983 | Loeb |
| 4,458,877 A * | 7/1984 | Holmes ............... A61M 39/225 251/117 |
| 4,483,326 A | 11/1984 | Yamaka et al. |
| 4,519,385 A | 5/1985 | Atkinson et al. |
| 4,630,598 A | 12/1986 | Bonnet |
| 4,648,871 A | 3/1987 | Jacob |
| 4,655,197 A | 4/1987 | Atkinson |
| 4,662,871 A | 5/1987 | Rafelson |
| 4,680,026 A | 7/1987 | Weightman et al. |
| 4,688,555 A | 8/1987 | Wardle |
| 4,696,669 A | 9/1987 | Menhusen |
| 4,706,656 A | 11/1987 | Kuboto |
| 4,708,717 A | 11/1987 | Deane et al. |
| 4,802,461 A | 2/1989 | Cho |
| 4,852,551 A | 8/1989 | Opie et al. |
| 4,874,360 A | 10/1989 | Goldberg et al. |
| 4,941,872 A | 7/1990 | Felix et al. |
| 4,950,265 A | 8/1990 | Taylor |
| 4,995,872 A | 2/1991 | Ferrara |
| 4,996,974 A | 3/1991 | Ciarlei |
| 5,057,080 A | 10/1991 | Takahashi |
| 5,095,889 A | 3/1992 | Weissmuller et al. |
| 5,120,305 A | 6/1992 | Boehringer et al. |
| 5,156,142 A | 10/1992 | Anapliotis et al. |
| 5,186,714 A | 2/1993 | Boudreault et al. |
| 5,191,881 A | 3/1993 | Beck |
| 5,226,885 A | 7/1993 | Takahashi |
| 5,230,704 A | 7/1993 | Moberg et al. |
| 5,263,938 A | 11/1993 | Orr et al. |
| 5,265,840 A | 11/1993 | Gillespie et al. |
| 5,273,524 A | 12/1993 | Fox et al. |
| 5,281,212 A | 1/1994 | Savage et al. |
| 5,295,956 A | 3/1994 | Bales et al. |
| 5,300,043 A | 4/1994 | Devlin et al. |
| 5,307,803 A | 5/1994 | Matsuura et al. |
| 5,312,327 A | 5/1994 | Bales et al. |
| 5,312,332 A | 5/1994 | Bales et al. |
| 5,312,400 A | 5/1994 | Bales et al. |
| 5,314,406 A | 5/1994 | Arias et al. |
| 5,318,541 A | 6/1994 | Viera et al. |
| 5,336,172 A | 8/1994 | Bales et al. |
| 5,336,220 A | 8/1994 | Ryan et al. |
| 5,350,356 A | 9/1994 | Bales et al. |
| 5,354,291 A | 10/1994 | Bales et al. |
| 5,429,596 A | 7/1995 | Arias et al. |
| 5,476,450 A | 12/1995 | Ruggio |
| 5,484,402 A | 1/1996 | Saravia et al. |
| 5,512,035 A | 4/1996 | Konstorum et al. |
| 5,512,045 A | 4/1996 | Gurchumelidze |
| 5,549,547 A | 8/1996 | Cohen et al. |
| 5,579,779 A | 12/1996 | Humphrey |
| 5,588,634 A | 12/1996 | Nettekoven |
| 5,607,420 A | 3/1997 | Schuman |
| 5,609,573 A | 3/1997 | Sandock |
| 5,643,304 A | 7/1997 | Schechter et al. |
| 5,658,258 A | 8/1997 | Kneer et al. |
| 5,776,096 A | 7/1998 | Fields |
| 5,827,229 A | 10/1998 | Auth et al. |
| 5,830,214 A | 11/1998 | Flom et al. |
| 5,836,909 A | 11/1998 | Cosmescu |
| 5,885,228 A | 3/1999 | Rosenman et al. |
| 5,885,288 A | 3/1999 | Aust et al. |
| 5,944,690 A | 8/1999 | Falwell et al. |
| 5,961,485 A | 10/1999 | Martin |
| 5,980,504 A | 11/1999 | Sharkey et al. |
| 6,066,150 A | 5/2000 | Gonon |
| 6,168,577 B1 | 1/2001 | Niederjohn et al. |
| 6,179,807 B1 | 1/2001 | Henniges et al. |
| 6,213,970 B1 | 4/2001 | Nelson et al. |
| 6,328,730 B1 | 12/2001 | Harkrider |
| 6,358,200 B1 | 3/2002 | Grossi |
| 6,471,639 B2 | 10/2002 | Rudischhauser et al. |
| 6,551,281 B1 | 4/2003 | Raulerson et al. |
| 6,623,445 B1 | 9/2003 | Nelson et al. |
| 6,635,028 B1 | 10/2003 | Ielpo et al. |
| 6,645,140 B2 | 11/2003 | Brommersma et al. |
| 6,755,806 B1 | 6/2004 | Von Casimir |
| 6,776,765 B2 | 8/2004 | Soukup et al. |
| 6,827,701 B2 | 12/2004 | MacMahon et al. |
| 6,830,556 B2 | 12/2004 | Harmon et al. |
| 6,857,617 B2 | 2/2005 | Forberg |
| 6,887,221 B1 | 5/2005 | Baillargeon et al. |
| 6,929,236 B1 | 8/2005 | Height et al. |
| 6,932,788 B2 | 8/2005 | Kamiyama et al. |
| 6,960,189 B2 | 11/2005 | Bates et al. |
| 6,969,368 B2 | 11/2005 | Anspach et al. |

(56) References Cited

U.S. PATENT DOCUMENTS

| | | |
|---|---|---|
| 6,997,867 B2 | 2/2006 | Soble et al. |
| 7,004,931 B2 | 2/2006 | Hogendijk |
| 7,025,720 B2 | 4/2006 | Boebel et al. |
| 7,179,269 B2 | 2/2007 | Welch et al. |
| 7,249,602 B1 | 7/2007 | Emanuel |
| 7,297,133 B2 | 11/2007 | Nelson et al. |
| 7,465,288 B2 | 12/2008 | Dudney et al. |
| 7,500,947 B2 | 3/2009 | Kucklick et al. |
| 7,503,893 B2 | 3/2009 | Kucklick |
| 7,530,976 B2 | 5/2009 | MacMahon et al. |
| 7,540,868 B2 | 6/2009 | Elliott et al. |
| 7,571,889 B2 | 8/2009 | Miyahara |
| 7,802,574 B2 | 9/2010 | Schultz |
| 7,810,784 B2 | 10/2010 | Abe et al. |
| 7,846,126 B2 | 12/2010 | Steen et al. |
| 7,857,770 B2 | 12/2010 | Raulerson et al. |
| 7,883,516 B2 | 2/2011 | Huang et al. |
| 7,935,049 B2 | 5/2011 | Michel et al. |
| 7,947,039 B2 | 5/2011 | Sartor |
| 7,972,282 B2 | 7/2011 | Clark et al. |
| 8,002,732 B2 | 8/2011 | Visconti |
| 8,052,607 B2 | 11/2011 | Byrd |
| 8,062,214 B2 | 11/2011 | Shener et al. |
| 8,118,731 B2 | 2/2012 | Kucklick et al. |
| 8,123,676 B2 | 2/2012 | Kucklick |
| 8,192,500 B2 | 6/2012 | Chung |
| 8,226,548 B2 | 7/2012 | Kucklick |
| 8,241,278 B2 | 8/2012 | Sartor |
| 8,313,081 B2 | 11/2012 | Adelberg |
| 8,353,860 B2 | 1/2013 | Boulais et al. |
| 8,419,626 B2 | 4/2013 | Shener-Irmakoglu et al. |
| 8,454,536 B2 | 6/2013 | Raulerson et al. |
| 8,460,182 B2 | 6/2013 | Ouyang et al. |
| 8,475,453 B2 | 7/2013 | Marczyk et al. |
| 8,613,735 B2 | 12/2013 | Omeda et al. |
| 8,672,928 B2 | 3/2014 | Liu et al. |
| 8,702,681 B2 | 4/2014 | Douglas et al. |
| 8,721,595 B2 | 5/2014 | Stiehl et al. |
| 8,740,773 B2 | 6/2014 | Kucklick et al. |
| 8,808,168 B2 | 8/2014 | Ettwein et al. |
| 8,845,521 B2 | 9/2014 | Maruyama |
| D715,921 S | 10/2014 | Wan |
| 8,858,569 B2 | 10/2014 | Wan |
| 8,870,748 B2 | 10/2014 | Kucklick |
| 8,888,683 B2 | 11/2014 | Mejia |
| 8,894,601 B2 | 11/2014 | Moehle et al. |
| 8,945,093 B2 | 2/2015 | Ahluwalia |
| 9,011,412 B2 | 4/2015 | Albritton et al. |
| 9,089,631 B2 | 7/2015 | Schaeffer et al. |
| 9,095,646 B2 | 8/2015 | Chow et al. |
| 9,095,682 B2 | 8/2015 | Romoscanu |
| 9,119,926 B2 | 9/2015 | Cuevas et al. |
| 9,138,347 B2 | 9/2015 | Wiljanen et al. |
| 9,155,453 B2 | 10/2015 | Kumar et al. |
| 9,155,454 B2 | 10/2015 | Sahney et al. |
| 9,167,958 B2 | 10/2015 | Banik et al. |
| 9,179,968 B2 | 11/2015 | Leo et al. |
| 9,186,044 B2 | 11/2015 | Kucklick et al. |
| 9,186,055 B2 | 11/2015 | Kucklick |
| 9,192,284 B2 | 11/2015 | Hirsch et al. |
| 9,204,786 B2 | 12/2015 | Kucklick |
| 9,241,612 B2 | 1/2016 | Hoshino |
| 9,248,228 B2 | 2/2016 | Bono et al. |
| 9,339,631 B2 | 5/2016 | Graham et al. |
| 9,358,061 B2 | 6/2016 | Plascencia et al. |
| 9,360,124 B2 | 6/2016 | Schaeffer et al. |
| 9,387,121 B2 | 7/2016 | Wiljanen et al. |
| 9,427,504 B2 | 8/2016 | Newman |
| 9,545,334 B2 | 1/2017 | Steen et al. |
| 9,572,933 B2 | 2/2017 | Grannell et al. |
| 9,622,646 B2 | 4/2017 | Ouyang et al. |
| 9,668,643 B2 | 6/2017 | Kennedy et al. |
| 9,717,397 B2 | 8/2017 | Kucklick |
| 9,743,827 B2 | 8/2017 | Yasunaga et al. |
| 9,744,276 B2 | 8/2017 | Ahluwalia |
| 9,757,195 B2 | 9/2017 | Plascencia et al. |
| 9,775,674 B2 | 10/2017 | Schaeffer et al. |
| 9,810,836 B2 | 11/2017 | Okagami et al. |
| 9,814,490 B2 | 11/2017 | Neoh et al. |
| 9,820,762 B2 | 11/2017 | Cadeddu et al. |
| 9,827,009 B2 | 11/2017 | Kucklick et al. |
| 9,833,130 B2 | 12/2017 | Schaeffer et al. |
| 9,839,739 B2 | 12/2017 | Qian |
| 9,861,788 B2 | 1/2018 | Yu et al. |
| 9,878,145 B2 | 1/2018 | Holm et al. |
| 9,883,960 B2 | 2/2018 | Cummins et al. |
| 9,884,143 B2 | 2/2018 | Kobida et al. |
| 9,918,859 B2 | 3/2018 | Cummins et al. |
| 9,936,963 B2 | 4/2018 | Batchelor et al. |
| 9,968,249 B2 | 5/2018 | Huang et al. |
| 9,974,554 B2 | 5/2018 | Antonelli et al. |
| 9,980,631 B2 | 5/2018 | Schaeffer et al. |
| 9,982,791 B2 | 5/2018 | Schaeffer et al. |
| 10,004,385 B2 | 6/2018 | Bresco Torras et al. |
| 10,010,657 B2 | 7/2018 | Torrance et al. |
| 10,010,700 B2 | 7/2018 | Romoscanu |
| 10,028,763 B2 | 7/2018 | Kumar et al. |
| 10,076,432 B2 | 9/2018 | Cummins et al. |
| 10,085,624 B2 | 10/2018 | Isoda et al. |
| 10,092,173 B2 | 10/2018 | Dejima |
| 10,098,768 B2 | 10/2018 | Cummins et al. |
| 10,105,247 B2 | 10/2018 | Cummins et al. |
| 10,154,919 B2 | 12/2018 | Cummins et al. |
| 10,165,933 B2 | 1/2019 | Dejima |
| 10,166,013 B2 | 1/2019 | Nguyen et al. |
| 10,213,533 B2 | 2/2019 | Walter |
| 10,220,123 B2 | 3/2019 | Monty et al. |
| 10,231,793 B2 | 3/2019 | Romo |
| 10,244,927 B2 | 4/2019 | Kennedy, II et al. |
| 10,245,359 B2 | 4/2019 | Bono et al. |
| 10,251,539 B2 | 4/2019 | Sahney et al. |
| 10,251,671 B2 | 4/2019 | Dejima |
| 10,265,056 B2 | 4/2019 | Stanton et al. |
| 10,271,716 B2 | 4/2019 | Ferreira et al. |
| 10,286,141 B2 | 5/2019 | Monty et al. |
| 10,293,105 B2 | 5/2019 | Panotopoulos |
| 10,383,656 B2 | 8/2019 | Raulerson et al. |
| 10,434,259 B2 | 10/2019 | Dejima et al. |
| 10,441,134 B2 | 10/2019 | Ouyang et al. |
| 10,441,153 B2 | 10/2019 | Huang et al. |
| 10,441,460 B2 | 10/2019 | Ross et al. |
| 10,456,519 B2 | 10/2019 | Ngo-Chu et al. |
| 10,478,596 B2 | 11/2019 | Graham et al. |
| 10,492,662 B2 | 12/2019 | Govrin et al. |
| 10,500,323 B2 | 12/2019 | Huering et al. |
| 10,507,303 B2 | 12/2019 | Terwey |
| 10,531,883 B1 | 1/2020 | Deville et al. |
| 10,561,440 B2 | 2/2020 | Look et al. |
| 10,583,272 B2 | 3/2020 | Yu et al. |
| 10,595,715 B2 | 3/2020 | Dejima |
| 10,596,306 B2 | 3/2020 | Ahluwalia |
| 10,610,622 B2 | 4/2020 | Jeong |
| 10,624,708 B2 | 4/2020 | Hunter |
| 10,625,062 B2 | 4/2020 | Matlock et al. |
| 10,694,927 B2 | 6/2020 | Kucklick |
| 10,722,253 B2 | 7/2020 | Deville et al. |
| 10,722,620 B2 | 7/2020 | Chuang et al. |
| 10,758,385 B2 | 9/2020 | Cummins et al. |
| 10,765,449 B2 | 9/2020 | Dejima |
| 10,842,519 B2 | 11/2020 | Suh et al. |
| 10,850,013 B2 | 12/2020 | Hsu et al. |
| 10,888,349 B2 | 1/2021 | Pereira et al. |
| 10,905,446 B2 | 2/2021 | Chae |
| 10,912,873 B2 | 2/2021 | Nitzan et al. |
| 10,918,365 B2 | 2/2021 | Kirkemo |
| 10,925,666 B2 | 2/2021 | Plascencia et al. |
| 10,932,798 B2 | 3/2021 | Shelton et al. |
| 10,952,758 B1 | 3/2021 | Evans |
| 10,959,868 B2 | 3/2021 | Cummins et al. |
| 10,966,737 B2 | 4/2021 | Nguyen |
| 10,967,107 B2 | 4/2021 | Forsberg et al. |
| 10,980,554 B2 | 4/2021 | Sperry et al. |
| 11,013,522 B2 | 5/2021 | Ciulla |
| 11,026,715 B2 | 6/2021 | Mayberry |

(56) References Cited

U.S. PATENT DOCUMENTS

| | | |
|---|---|---|
| 11,035,481 B2 | 6/2021 | Schaeffer et al. |
| 11,051,678 B2 | 7/2021 | Nieman |
| 11,064,869 B2 | 7/2021 | McWeeney et al. |
| 11,064,871 B2 | 7/2021 | Gerbo et al. |
| 11,076,755 B2 | 8/2021 | Huang et al. |
| 11,089,944 B2 | 8/2021 | Rentschler et al. |
| 11,090,072 B2 | 8/2021 | Morey et al. |
| 11,096,555 B2 | 8/2021 | Harrah et al. |
| 11,096,568 B2 | 8/2021 | Harrah et al. |
| 11,109,874 B2 | 9/2021 | Gavala et al. |
| 11,116,530 B2 | 9/2021 | Yurek |
| 11,123,483 B2 | 9/2021 | Panotopoulos |
| 11,141,177 B2 | 10/2021 | Ganz et al. |
| 11,141,185 B2 | 10/2021 | Efremkin |
| 11,167,077 B2 | 11/2021 | Long et al. |
| 11,179,520 B2 | 11/2021 | Farah et al. |
| 11,185,380 B2 | 11/2021 | Burbank et al. |
| 11,241,243 B2 | 2/2022 | Pereira et al. |
| 11,241,290 B2 | 2/2022 | Waterbury et al. |
| 11,260,928 B2 | 3/2022 | Taylor |
| 11,278,300 B2 | 3/2022 | Bahmanyar et al. |
| 11,284,912 B2 | 3/2022 | St. George |
| 11,284,940 B2 | 3/2022 | Shelton |
| 11,324,526 B2 | 5/2022 | Yurek |
| 11,330,966 B2 | 5/2022 | Harrah et al. |
| 11,357,523 B2 | 6/2022 | Bionda et al. |
| 11,382,643 B2 | 7/2022 | Horowitz et al. |
| 11,382,650 B2 | 7/2022 | Noonan et al. |
| 11,382,652 B2 | 7/2022 | Wasdyke et al. |
| 11,382,693 B2 | 7/2022 | Harrah et al. |
| 11,399,892 B2 | 8/2022 | Yu et al. |
| 11,419,679 B2 | 8/2022 | Khachaturov et al. |
| 11,433,172 B2 | 9/2022 | Gao et al. |
| 11,452,436 B2 | 9/2022 | Chu et al. |
| 11,452,534 B2 | 9/2022 | Pereira et al. |
| 11,471,175 B2 | 10/2022 | Nguyen et al. |
| 11,471,176 B2 | 10/2022 | Greenhalgh et al. |
| 11,490,912 B2 | 11/2022 | Bonneau et al. |
| 11,490,913 B2 | 11/2022 | Nguyen et al. |
| 11,503,993 B2 | 11/2022 | Chu et al. |
| 11,510,691 B2 | 11/2022 | Nguyen et al. |
| 11,534,190 B2 | 12/2022 | Chu |
| 11,534,249 B2 | 12/2022 | Romo et al. |
| 11,547,479 B2 | 1/2023 | Shelton et al. |
| 11,559,360 B2 | 1/2023 | Romo |
| 11,571,229 B2 | 2/2023 | Shah |
| 11,576,692 B2 | 2/2023 | Gatineau et al. |
| 11,576,853 B2 | 2/2023 | Petkoska et al. |
| 11,577,056 B2 | 2/2023 | Rentschler et al. |
| 11,589,881 B2 | 2/2023 | Horowitz et al. |
| 11,596,423 B2 | 3/2023 | Nguyen et al. |
| 11,602,262 B2 | 3/2023 | Chu |
| 11,602,363 B2 | 3/2023 | Nguyen |
| 11,607,484 B2 | 3/2023 | Hanna et al. |
| 11,653,827 B2 | 5/2023 | Chu et al. |
| 11,672,598 B2 | 6/2023 | Morey et al. |
| 11,672,601 B2 | 6/2023 | Chu et al. |
| 2003/0199986 A1 | 10/2003 | Mcweeney et al. |
| 2003/0216760 A1 | 11/2003 | Welch et al. |
| 2004/0019358 A1 | 1/2004 | Kear |
| 2004/0143197 A1 | 7/2004 | Soukup et al. |
| 2004/0153095 A1 | 8/2004 | Seddon |
| 2004/0153111 A1* | 8/2004 | Hosoada ........ A61B 17/320016 |
| | | 604/48 |
| 2004/0193103 A1 | 9/2004 | Kumar |
| 2004/0236312 A1 | 11/2004 | Nistal et al. |
| 2004/0267213 A1 | 12/2004 | Knapp |
| 2005/0085692 A1 | 4/2005 | Kiehn et al. |
| 2005/0085769 A1 | 4/2005 | MacMahon et al. |
| 2005/0143678 A1 | 6/2005 | Schwarz et al. |
| 2005/0149201 A1 | 7/2005 | Mcweeney et al. |
| 2006/0041186 A1 | 2/2006 | Vancaillie |
| 2006/0069343 A1 | 3/2006 | Rontal |
| 2006/0135948 A1 | 6/2006 | Vrma |
| 2006/0149127 A1 | 7/2006 | Seddiqui et al. |
| 2006/0206004 A1 | 9/2006 | Dehmel et al. |
| 2006/0264995 A1 | 11/2006 | Fanton et al. |
| 2007/0185383 A1 | 8/2007 | Mulhern et al. |
| 2007/0298069 A1 | 12/2007 | Bucay-couto et al. |
| 2008/0004578 A1 | 1/2008 | Nixon et al. |
| 2008/0058588 A1 | 3/2008 | Emanuel |
| 2008/0146991 A1 | 6/2008 | Hernandez et al. |
| 2008/0167526 A1 | 7/2008 | Crank et al. |
| 2008/0167527 A1* | 7/2008 | Slenker ................ A61B 1/0051 |
| | | 600/156 |
| 2008/0249483 A1 | 10/2008 | Slenker et al. |
| 2009/0163846 A1 | 6/2009 | Aklog et al. |
| 2009/0270894 A1 | 10/2009 | Rubin et al. |
| 2010/0010431 A1 | 1/2010 | Tulley |
| 2010/0056867 A1 | 3/2010 | Labombard et al. |
| 2010/0137846 A1 | 6/2010 | Desai et al. |
| 2010/0305475 A1 | 12/2010 | Hinchliffe et al. |
| 2011/0004197 A1 | 1/2011 | Sansoucy |
| 2011/0060315 A1 | 3/2011 | Windheuser et al. |
| 2011/0202039 A1 | 8/2011 | Schaaf |
| 2011/0224489 A1 | 9/2011 | Deal et al. |
| 2011/0245841 A1 | 10/2011 | Shohat et al. |
| 2012/0041358 A1 | 2/2012 | Mann et al. |
| 2012/0220832 A1 | 8/2012 | Nakade et al. |
| 2013/0024003 A1 | 1/2013 | Mcweeney et al. |
| 2013/0123721 A1 | 5/2013 | Stiehl et al. |
| 2013/0131445 A1 | 5/2013 | Zerfas et al. |
| 2013/0138036 A1 | 5/2013 | Solomon et al. |
| 2013/0165944 A1 | 6/2013 | Gal et al. |
| 2013/0231605 A1 | 9/2013 | Walter |
| 2013/0253387 A1 | 9/2013 | Bonutti et al. |
| 2014/0107565 A1 | 4/2014 | Wiljanen et al. |
| 2014/0171922 A1 | 6/2014 | Douglas et al. |
| 2014/0180010 A1 | 6/2014 | Kumar et al. |
| 2014/0207056 A1 | 7/2014 | Bono et al. |
| 2014/0276207 A1 | 9/2014 | Ouyang et al. |
| 2014/0276377 A1 | 9/2014 | Chang et al. |
| 2014/0288460 A1 | 9/2014 | Ouyang et al. |
| 2014/0296868 A1 | 10/2014 | Garrison et al. |
| 2014/0296894 A1 | 10/2014 | Kojima et al. |
| 2015/0038785 A1 | 2/2015 | Govrin et al. |
| 2015/0141907 A1 | 5/2015 | Clement et al. |
| 2015/0150441 A1 | 6/2015 | Ouyang et al. |
| 2015/0164595 A1 | 6/2015 | Bogusky et al. |
| 2015/0305759 A1 | 10/2015 | St. George et al. |
| 2015/0328394 A1 | 11/2015 | Chow et al. |
| 2016/0001050 A1 | 1/2016 | Yee et al. |
| 2016/0022289 A1 | 1/2016 | Wan |
| 2016/0030070 A1 | 2/2016 | Eisner |
| 2016/0120557 A1* | 5/2016 | Goddard ............. A61M 3/0283 |
| | | 606/127 |
| 2016/0270804 A1 | 9/2016 | Honda et al. |
| 2016/0374710 A1 | 12/2016 | Sinelnikov et al. |
| 2016/0374755 A1 | 12/2016 | Mirigian et al. |
| 2017/0027604 A1 | 2/2017 | Wallace |
| 2017/0065752 A1 | 3/2017 | Eisner |
| 2017/0215897 A1 | 8/2017 | Fan |
| 2017/0215899 A1 | 8/2017 | Harrah et al. |
| 2017/0215964 A1 | 8/2017 | Harrah et al. |
| 2017/0215965 A1 | 8/2017 | Harrah et al. |
| 2017/0252051 A1 | 9/2017 | Wan et al. |
| 2017/0252103 A1 | 9/2017 | Griefeneder et al. |
| 2017/0258550 A1 | 9/2017 | Vazales |
| 2017/0266046 A1 | 9/2017 | Steen et al. |
| 2017/0303940 A1 | 10/2017 | Sperry et al. |
| 2017/0303941 A1 | 10/2017 | Eisner |
| 2017/0319776 A1 | 11/2017 | Eisner |
| 2017/0333614 A1 | 11/2017 | Gao et al. |
| 2017/0340862 A1 | 11/2017 | Calabrese et al. |
| 2017/0354431 A1 | 12/2017 | Rubin et al. |
| 2018/0055568 A1 | 3/2018 | Shelton et al. |
| 2018/0206866 A1 | 7/2018 | Wan |
| 2018/0360480 A1 | 12/2018 | Ciulla |
| 2019/0038817 A1 | 2/2019 | Forsberg et al. |
| 2019/0059988 A1 | 2/2019 | Davison et al. |
| 2019/0099209 A1 | 4/2019 | Witt et al. |
| 2019/0192222 A1 | 6/2019 | Mirigian et al. |
| 2019/0274699 A1 | 9/2019 | Morey et al. |
| 2019/0290811 A1 | 9/2019 | Bono et al. |

(56) References Cited

U.S. PATENT DOCUMENTS

| | | |
|---|---|---|
| 2019/0314044 A1 | 10/2019 | Long et al. |
| 2019/0328412 A1 | 10/2019 | Mazhar et al. |
| 2019/0343586 A1 | 11/2019 | Bonneau et al. |
| 2019/0357762 A1 | 11/2019 | Clayman et al. |
| 2020/0009302 A1 | 1/2020 | Pyle |
| 2020/0046393 A1 | 2/2020 | Kendale et al. |
| 2020/0069319 A1 | 3/2020 | Harrah et al. |
| 2020/0147294 A1 | 5/2020 | Edwards |
| 2020/0178767 A1 | 6/2020 | Miller |
| 2020/0178773 A1 | 6/2020 | Miller |
| 2020/0188014 A1 | 6/2020 | Woloszko et al. |
| 2020/0196843 A1 | 6/2020 | Tah et al. |
| 2020/0229907 A1 | 7/2020 | Duehlmeier |
| 2020/0297362 A1 | 9/2020 | Deville et al. |
| 2020/0397507 A1 | 12/2020 | Liu |
| 2020/0397975 A1 | 12/2020 | Kirk et al. |
| 2021/0015507 A1 | 1/2021 | Roberts et al. |
| 2021/0015509 A1 | 1/2021 | Wan |
| 2021/0022756 A1 | 1/2021 | Ciulla |
| 2021/0022757 A1 | 1/2021 | Wan |
| 2021/0022759 A1 | 1/2021 | Wan |
| 2021/0076904 A1 | 3/2021 | Calabrese et al. |
| 2021/0084766 A1 | 3/2021 | Govrin |
| 2021/0085158 A1 | 3/2021 | Ikuma et al. |
| 2021/0093338 A1 | 4/2021 | Baker et al. |
| 2021/0093340 A1 | 4/2021 | Baker et al. |
| 2021/0093341 A1 | 4/2021 | Baker et al. |
| 2021/0113268 A1 | 4/2021 | Waisman et al. |
| 2021/0121188 A1 | 4/2021 | Yurek |
| 2021/0177444 A1 | 6/2021 | Shelton et al. |
| 2021/0178032 A1 | 6/2021 | Hsu et al. |
| 2021/0228274 A1 | 7/2021 | Pyro et al. |
| 2021/0236204 A1 | 8/2021 | Tower et al. |
| 2021/0275248 A1 | 9/2021 | Pyro et al. |
| 2021/0307589 A1 | 10/2021 | Rentschler et al. |
| 2021/0315595 A1 | 10/2021 | Crawford et al. |
| 2021/0315608 A1 | 10/2021 | Mozloom, Jr |
| 2021/0321861 A1 | 10/2021 | McWeeney et al. |
| 2021/0322040 A1 | 10/2021 | Gavala et al. |
| 2021/0330309 A1 | 10/2021 | Ma et al. |
| 2021/0338064 A1 | 11/2021 | Fitterer et al. |
| 2021/0338257 A1 | 11/2021 | Morey et al. |
| 2021/0361356 A1 | 11/2021 | Shelton et al. |
| 2021/0369095 A1 | 12/2021 | Stem et al. |
| 2021/0378740 A1 | 12/2021 | Chu et al. |
| 2021/0386273 A1 | 12/2021 | Purohit et al. |
| 2022/0000508 A1 | 1/2022 | Schmitt et al. |
| 2022/0022912 A1 | 1/2022 | Efremkin et al. |
| 2022/0023528 A1 | 1/2022 | Long et al. |
| 2022/0023563 A1 | 1/2022 | Ganz et al. |
| 2022/0031392 A1 | 2/2022 | Maher et al. |
| 2022/0047283 A1 | 2/2022 | Baker et al. |
| 2022/0047287 A1 | 2/2022 | Stender et al. |
| 2022/0047332 A1 | 2/2022 | Schmitt et al. |
| 2022/0053995 A1 | 2/2022 | Knollman et al. |
| 2022/0053998 A1 | 2/2022 | Ghani et al. |
| 2022/0054162 A1 | 2/2022 | Efremkin |
| 2022/0061827 A1 | 3/2022 | Schmitt et al. |
| 2022/0061866 A1 | 3/2022 | Crawford et al. |
| 2022/0072213 A1 | 3/2022 | Thoreson |
| 2022/0087697 A1 | 3/2022 | Yurek |
| 2022/0087698 A1 | 3/2022 | Yurek |
| 2022/0096108 A1 | 3/2022 | Baker et al. |
| 2022/0104839 A1 | 4/2022 | Horowitz et al. |
| 2022/0104840 A1 | 4/2022 | Horowitz et al. |
| 2022/0133340 A1 | 5/2022 | Schaeffer et al. |
| 2022/0135171 A1 | 5/2022 | Taylor |
| 2022/0142463 A1 | 5/2022 | Altshuler et al. |
| 2022/0142659 A1 | 5/2022 | Melsheimer et al. |
| 2022/0168003 A1 | 6/2022 | Crowley |
| 2022/0183706 A1 | 6/2022 | Pereira et al. |
| 2022/0202285 A1 | 6/2022 | Bukesov et al. |
| 2022/0226016 A1 | 6/2022 | Ganz et al. |
| 2022/0218367 A1 | 7/2022 | Ghani et al. |
| 2022/0218416 A1 | 7/2022 | Vogel |
| 2022/0233199 A1 | 7/2022 | Du et al. |
| 2022/0240761 A1 | 8/2022 | Harrah et al. |
| 2022/0240762 A1 | 8/2022 | Rentschler et al. |
| 2022/0265350 A1 | 8/2022 | Clayman et al. |
| 2022/0273860 A1 | 9/2022 | Wiener et al. |
| 2022/0280021 A1 | 9/2022 | Chu |
| 2022/0287774 A1 | 9/2022 | Ikuma et al. |
| 2022/0287775 A1 | 9/2022 | Harrah et al. |
| 2022/0296300 A1 | 9/2022 | Takata |
| 2022/0304548 A1 | 9/2022 | Chu |
| 2022/0313290 A1 | 10/2022 | Obermiller et al. |
| 2022/0323153 A1 | 10/2022 | Yu et al. |
| 2022/0338891 A1 | 10/2022 | Johnson et al. |
| 2022/0354520 A1 | 11/2022 | Mannion et al. |
| 2022/0362449 A1 | 11/2022 | Gao et al. |
| 2022/0362511 A1 | 11/2022 | Gavalis et al. |
| 2022/0369906 A1 | 11/2022 | Wilson et al. |
| 2022/0369919 A1 | 11/2022 | Chu et al. |
| 2022/0370085 A1 | 11/2022 | Reagan, Jr. et al. |
| 2022/0370127 A1 | 11/2022 | Khachaturov et al. |
| 2022/0386852 A1 | 12/2022 | Chu et al. |
| 2022/0387534 A1 | 12/2022 | Petkoska |
| 2022/0401119 A1 | 12/2022 | Pereira et al. |
| 2023/0028334 A1 | 1/2023 | Aljure |
| 2023/0030708 A1 | 2/2023 | Noonan et al. |
| 2023/0031136 A1 | 2/2023 | Ikuma |
| 2023/0055911 A1 | 2/2023 | Chu et al. |
| 2023/0063701 A1 | 3/2023 | Horowitz et al. |
| 2023/0066304 A1 | 3/2023 | Nguyen et al. |
| 2023/0075988 A1 | 3/2023 | Scheib et al. |
| 2023/0081712 A1 | 3/2023 | Shelton et al. |
| 2023/0083127 A1 | 3/2023 | Hayashi et al. |
| 2023/0103647 A1 | 4/2023 | Nguyen et al. |
| 2023/0113437 A1 | 4/2023 | Horie et al. |
| 2023/0113650 A1 | 4/2023 | Sasaguchi |
| 2023/0115997 A1 | 4/2023 | Sato et al. |
| 2023/0125143 A1 | 4/2023 | Schmitt |
| 2023/0130679 A1 | 4/2023 | Avolos |
| 2023/0130759 A1 | 4/2023 | Shelton |
| 2023/0131637 A1 | 4/2023 | Shelton et al. |
| 2023/0145569 A1 | 5/2023 | McWeeney et al. |
| 2023/0146163 A1 | 5/2023 | Yurek |
| 2023/0146598 A1 | 5/2023 | Yurek |
| 2023/0148845 A1 | 5/2023 | McWeeney et al. |
| 2023/0165599 A1 | 6/2023 | Nguyen et al. |
| 2023/0181011 A1 | 6/2023 | Chu |
| 2023/0181203 A1 | 6/2023 | Nguyen et al. |
| 2023/0181204 A1 | 6/2023 | Shah |
| 2023/0190078 A1 | 6/2023 | Clayman et al. |
| 2023/0190316 A1 | 6/2023 | Nguyen |
| 2023/0190317 A1 | 6/2023 | Horowitz et al. |
| 2023/0190373 A1 | 6/2023 | Hutchens et al. |
| 2023/0210586 A1 | 7/2023 | Mantri et al. |
| 2023/0263369 A1 | 8/2023 | Chu et al. |
| 2023/0263571 A1 | 8/2023 | Chu et al. |
| 2023/0301718 A1 | 9/2023 | Harrah et al. |
| 2023/0346202 A1 | 11/2023 | Harrah et al. |
| 2024/0057855 A1 | 2/2024 | Reed et al. |
| 2024/0099563 A1 | 3/2024 | Wales et al. |
| 2024/0130743 A1 | 4/2024 | Hajjar |
| 2024/0138666 A1 | 5/2024 | Chu et al. |
| 2024/0138913 A1 | 5/2024 | Carlson et al. |
| 2024/0148394 A1 | 5/2024 | Baker et al. |

FOREIGN PATENT DOCUMENTS

| | | |
|---|---|---|
| CN | 203988361 U | 12/2014 |
| KR | 10-2167406 B1 | 10/2020 |
| WO | WO 2010/068467 A1 | 6/2010 |
| WO | WO 2014/160201 A1 | 10/2014 |
| WO | WO 2017/135980 A1 | 8/2017 |
| WO | WO 2018/215954 A1 | 11/2018 |
| WO | WO 2019/178387 A1 | 9/2019 |
| WO | WO 2020/146454 A1 | 7/2020 |

(56) References Cited

FOREIGN PATENT DOCUMENTS

| | | |
|---|---|---|
| WO | WO 2020/150713 A2 | 7/2020 |
| WO | WO 2020/247103 A1 | 12/2020 |

OTHER PUBLICATIONS

Non-Final Office Action dated Apr. 28, 2023 for U.S. Appl. No. 18/090,802; 29 pages.

Communication dated Oct. 26, 2021 forwarding the extended European Search Report for European Patent Application No. 19746731.9; 12 pages.

Chew, et al., "Natural History, Complications and Re-Intervention Rates of Asymptomatic Residual Stone Fragments after Ureteroscopy: a Report from the EDGE Research Consortium", The Journal of Urology; Apr. 2016 (published online Nov. 2015); vol. 195, pp. 982-986.

Deng, et al., "Suctioning flexible ureteroscopy with automatic controlof renal pelvic pressure: a porcine model", International Journal of Clinical and Experimental Medicine, Mar. 30, 2016.

Deng, et al., "A Novel Flexible Ureteroscopy with Intelligent Control of Renal Pelvic Pressure: An Initial Experience of 93 Cases", Journal of Endourology; Oct. 2016 (published online Aug. 2016); vol. 30(10), pp. 1067-1072.

Emmott, et al., "Complications, Re-Intervention Rates, and Natural History of Residual Stone Fragments After Percutaneous Nephrolithotomy", Journal of Endourology; Jan. 2018; vol. 32(1), pp. 28-32.

Huang, et al., "Endourology and Stones | The Application of Suctioning Flexible Ureteroscopy With Intelligent Pressure Control in Treating Upper Urinary Tract Calculi on Patients With a Solitary Kidney", Urology Jan. 2018; vol. 111, pp. 44-47.

Kim, et al., "The Clinical Efficacy of Dual-Lumen Catheter Technique in Retrograde Intrarenal Surgery for the Management of Nephrolithiasis: A Propensity Score Analysis", Journal of Endourology; Dec. 2018; vol. 32(12).

Leveillee, et al., "Impressive Performance: New Disposable Digital Ureteroscope Allows for Extreme Lower Pole Access and Use of 365 μm Holmium Laser Fiber", Journal of Endourology Case Reports; Jun. 1, 2016; vol. 2(1), pp. 114-116.

Li, et al., "A Novel Semirigid Ureterorenoscope with Vacuum Suctioning System for Management of Single Proximal Ureteral and Renal Pelvic Stones: An Initial Experience", Journal of Endourology; Dec. 2018; vol. 32(12), pp. 1154-1159.

Peng, et al., "Suctioning flexible ureteroscopic lithotripsy in the oblique supine lithotomy position and supine lithotomy position: a comparative retrospective study", Minerva Urologica e Nefrologica, Dec. 2018; vol. 70(6), pp. 612-616.

Portis, et al., "Endourology and Stones | Repeat Surgery After Ureteroscopic Laser Lithotripsy With Attempted Complete Extraction of Fragments: Long-term Follow-up", Urology Jun. 2015; vol. 85(6), pp. 1272-1278.

Raman, et al., "Natural History of Residual Fragments Following Percutaneous Nephrostolithotomy", Journal of Urology Mar. 2009; vol. 181(3), pp. 1163-1168.

Rebuck, et al., "Endourology and Stones | The Natural History of Renal Stone Fragments Following Ureteroscopy", Urology Mar. 2011; vol. 77(3), pp. 564-568.

Scales, et al., "The impact of unplanned postprocedure visits in the management of patients with urinary stones", Surgery May 2014; vol. 155(5), pp. 769-775.

Skolarikos, et al., "Urolithiasis/Endourology | Outcomes of Flexible Ureterorenoscopy for Solitary Renal Stones in the CROES URS Global Study", Journal of Urology Jul. 2015; vol. 194(1), pp. 137-143.

Villanueva, et al., "Silicone Catheters May Be Superior to Latex Catheters in Difficult Urethral Catheterization After Urethral Dilation", Journal of Endourology 2011, vol. 25(5), pp. 841-844.

Zeng, et al., "Modified Access Sheath for Continuous Flow Ureteroscopic Lithotripsy: A Preliminary Report of a Novel Concept and Technique", Journal of Endourology Sep. 2016; vol. 30(9), pp. 992-996.

Ali, et al: "Retrograde Cystonephroscopy for Complex Renal Calculi Using Novel Dual-Action Aspiration, Irrigation Cystoscope: Initial Case Series", Journal of Endourology; Jul. 2022; vol. 36 (7); pp. 898-905.

Chen, et al: "The Comparison Study of Flexible Ureteroscopic Suctioning Lithotripsy With Intelligent Pressure Control Versus Minimally Invasive Percutaneous Suctioning Nephrolithotomy in Treating Renal Calculi of 2 to 3 cm in Size", Surgical Innovation 2019; vol. 26(5); pp. 528-535.

Jiang, et al: "Ex Vivo Renal Stone Dusting: Impact of Laser Modality, Ureteral Access Sheath, and Suction on Total Stone Clearance", Journal of Endourology; Apr. 2022; vol. 36(4); pp. 499-507.

Karani, et al: "Evaluation of a Novel Female Gender Flexible Ureteroscope: Comparison of Flow and Deflection to a Standard Flexible Ureteroscope", Journal of Endourology; Jun. 2021; vol. 35(6); pp. 840-846.

Keller, et al: "Next-Generation Fiberoptic and Digital Ureteroscopes", Urol Clin North Am.; May 2019; vol. 46(2); pp. 147-163.

Lai, et al: "RIRS with Vacuum-Assisted Ureteral Access Sheath versus MPCNL for the Treatment of 2-4cm Renal Stone", BioMed Research International 2020; vol. 2020, Article ID 8052013, 8 pages.

Schneider, et al: "In Vitro Evaluation of Stone Fragment Evacuation by Suction", Journal of Endourology; Feb. 2021; vol. 35(2); pp. 187-191.

Williams, et al: "The Fluid Mechanics of Ureteroscope Irrigation", Journal of Endourology; Jan. 2019; vol. 33(1); pp. 28-34.

Williams, et al: "A lumped-parameter model for kidney pressure during stone removal," IMA Journal of Applied Mathematics; Oct. 2020; vol. 85(5); pp. 703-723.

Williams, et al: "Cavity Flow Characteristics and Applications to Kidney Stone Removal," Journal of Fluid Mechanics 2020; vol. 902; A16.

Williams, et al: "Effects of Geometry on Resistance in Elliptical Pipe Flows," Journal of Fluid Mechanics 2020; vol. 891; A4-1.

Williams, et al: "Shape optimisation for faster washout in recirculating flows," Journal of Fluid Mechanics 2021; vol. 914; A37.

Zanetti, et al: "Vacuum-assisted mini-percutaneous nephrolithotomy: a new perspective in fragments clearance and intrarenal pressure control", World Journal of Urology 2021; vol. 39; pp. 1717-1723.

Non-final office action mailed Aug. 9, 2023 for U.S. Appl. No. 16/966,856; 40 pages.

Non-final office action mailed Aug. 9, 2023 for U.S. Appl. No. 17/489,723; 25 pages.

Non-final office action mailed Aug. 9, 2023 for U.S. Appl. No. 18/091,308; 27 pages.

Invitation To Pay Additional Fees And, Where Applicable, Protest Fee mailed May 24, 2023 for International Patent Application No. PCT/US2023/014276; 14 pages.

International Search Report and Written Opinion mailed Jul. 31, 2023 for International Patent Application No. PCT/US2023/014276; 60 pages.

Final Office Action dated Aug. 25, 2023, for U.S. Appl. No. 18/090,802, 29 pages.

* cited by examiner

KIDNEY STONE TREATMENT SYSTEM

CROSS-REFERENCE TO RELATED APPLICATIONS

This application is a National Stage filing under 35 U.S.C. § 371 of International Patent Application No. PCT/US2023/014276, filed Mar. 1, 2023, which claims the benefit of and priority to U.S. Provisional Application No. 63/315,815 filed Mar. 2, 2022, U.S. Provisional Application No. 63/357,468 filed Jun. 30, 2022, and U.S. Provisional Application No. 63/411,568 filed Sep. 29, 2022, the contents of all of which are hereby incorporated by reference in their entireties for all purposes.

FIELD

The present inventions generally relate to systems, devices, and methods for guided removal of objects in vivo; and more particularly to mechanisms for irrigation and removal of objects, such as kidney stones.

BACKGROUND

Kidney stones are a common medical problem that negatively impacts millions of individuals worldwide. Kidney stones include one or more solid masses of material that are usually made of crystals and form in parts of the urinary tract including in the ureter, the kidney, and/or the bladder of the individual. Kidney stones range in size from small (less than about 1 cm) to very large (more than 4 cm) and may cause significant pain to the individual and damage to the kidney. The overwhelming majority of stones that are treated by surgeons are less than 1 cm.

The recommended treatment for removal of kidney stones varies according to numerous factors including the size of the kidney stones, the number of kidney stones, and the location of the kidney stones. The most common treatments for kidney stones are shock wave lithotripsy (ultrasound waves used to fracture the stones), ureteroscopy (fracture and removal of the stones using an endoscope that is introduced through the bladder), and percutaneous nephrolithotomy (fracture and removal of the stones using an endoscope that is introduced through a sheath placed through the patient's back into the kidney).

The largest kidney stones are usually removed through percutaneous nephrolithotomy or nephrolithotripsy. In these procedures, a small incision is made through the patient's back adjacent the kidney and a sheath is passed into the kidney to accommodate a larger endoscope used to fracture and remove stones. The stone may be removed directly through the tube or may be broken up into small fragments while still in the patient's body and then removed via a vacuum or other known methods.

There are numerous drawbacks associated with nephrolithotomy, nephrolithotripsy, and other invasive surgeries requiring an incision in the skin. Namely, such surgical techniques may require significantly more anesthesia administered to the patient, the surgeries are more complicated and pose a higher risk of infection and complications for the patient, and the surgeries require a substantial incision in the patient, which may leave a scar. Additionally, given the invasiveness of the procedure, percutaneous procedures are usually not preferred for smaller kidney stones (e.g., less than 1 cm) depending on the size and location of the stones.

Traditionally, smaller kidney stones have been treated using less invasive techniques including through ureteroscopy. In ureteroscopy, the surgeon typically inserts a ureteroscope into the urethra, through the bladder, and the ureter to provide the surgeon with a direct visualization of the kidney stones which may reside in the ureter or kidney. The surgeon then removes the kidney stone directly using a basketing device if the kidney stone is small enough to pass through the urinary tract without difficulty, or the surgeon fractures the kidney stone into smaller pieces using a laser or other breaking device. A laser lithotripsy device is inserted through the ureteroscope and is used to fragmentize the larger kidney stones into smaller pieces. After breaking the kidney stone into smaller pieces, the surgeon removes the laser or breaking device and inserts a basket or an extraction catheter to capture the kidney stone fragments under the direct visualization of the ureteroscope. Upon retrieving some of the kidney stone fragments, the surgeon removes the basket from the patient and empties the kidney stone fragments therefrom. This process is repeated until clinically significant kidney stones and kidney stone fragments are broken up and removed from the body.

It should be apparent that this process is extremely time consuming, costly, and inefficient because the surgeon is required to insert and remove the scope and basket into and out of the patient many times to completely remove the kidney stones and kidney stone fragments. Using a basket removal device to capture kidney stones or kidney stone fragments suffers from other drawbacks in that the basket is difficult to position adjacent the kidney stone fragments and maneuver in a manner that effectively retrieves the fragments. The training required for such a procedure is not insignificant and the basket removal technique can be difficult for even the most skilled surgeons. Additionally, the surgeon is susceptible to hand fatigue due to the extended amount of time required to operate the kidney stone retrieval baskets. Further, the patient is required to be under local anesthesia and/or remain immobile over an extended amount of time. Still further, the basket retrieval devices cause irritation to the urinary tract due to the repeated insertion and removal.

Thus, there is an unmet need for new devices and methods that permit minimally invasive removal of kidney stones.

SUMMARY

In accordance with one aspect of the invention, a kidney stone removal mechanism is provided. The mechanism comprises an irrigation tube; a vacuum tube; and a trigger mechanism. The trigger mechanism includes a trigger operable by a user. The trigger can be located at a proximal end of the kidney stone removal mechanism. The trigger mechanism can be operable to selectively constrict, close, and open the irrigation tube to irrigate an area of treatment upon user operation of the trigger, and to selectively initiate vacuum within the vacuum tube to remove partial or entire kidney stones upon user operation of the trigger. A user depression of the trigger can progressively open the irrigation tube. In an embodiment, the trigger comprises a first protrusion, such that a user operation of the trigger causes the first protrusion to selectively constrict, close, and open the irrigation tube. The user depression of the trigger can cause the first protrusion to progressively open the irrigation tube. In an embodiment, the trigger can comprise a second protrusion, such that a user depression of the trigger causes the second protrusion to selectively initiate vacuum within the vacuum tube. The user depression of the trigger can cause the second protrusion to progressively initiate vacuum within the vacuum tube. The kidney stone removal mechanism can further comprise
a catheter connected at its proximal end to a distal end of the kidney stone removal mechanism. The catheter has a distal tip at a distal end of the catheter. A steering mechanism can be located at the proximal end of the kidney stone removal mechanism. The steering mechanism is operable to steer the distal tip to facilitate removal of partial or entire kidney stones. The steering mechanism can comprise at least one wire, connected between the steering mechanism and the catheter, to move the distal tip to a desired location to facilitate removal of partial or entire kidney stones.

The first protrusion can comprise a roller. The second protrusion can comprise a roller. The trigger can comprise a third protrusion and the trigger mechanism can comprise a first detent that is selectively engageable with the third protrusion, to alert the user to a predetermined amount of depression of the trigger. The first detent can comprise an edge of a protrusion inside the trigger mechanism or can comprise an edge of a depression inside the trigger mechanism. The third protrusion of the trigger can comprise a roller. The kidney stone removal mechanism can further comprise a second detent to alert the user to a full amount of depression of the trigger. The second detent can comprise the protrusion inside the trigger mechanism. The second detent can comprise an opposite edge of the depression inside the trigger mechanism. The roller can engage with the opposite edge of the depression to alert the user to a full amount of depression of the trigger.

In accordance with an embodiment, the trigger mechanism can be located at the proximal end of the kidney stone removal mechanism so as to be operable by a user's thumb. The trigger mechanism can be located at the proximal end of the kidney stone removal mechanism so as to be operable by a user's finger. The steering mechanism can be located at the proximal end of the kidney stone removal mechanism so as to be operable by a user's thumb.

In accordance with an embodiment, the kidney stone removal mechanism further comprises a resilient device that interacts with the trigger mechanism to cause the trigger mechanism to return to a home position in response to user release of the trigger. The resilient device can comprise a spring.

In accordance with an embodiment, the kidney stone removal mechanism further comprises a vacuum activation tube connected to the vacuum tube. The second protrusion can initiate vacuum within the vacuum tube by pinching the vacuum activation tube shut. The second protrusion can initiate vacuum within the vacuum tube by covering a port of the vacuum activation tube.

In accordance with an aspect of the invention, a kidney stone removal mechanism is provided comprising an irrigation tube configured carry fluid and having a portion passing within a trigger mechanism and a bypass structure connected in two places with the irrigation tube and configured to allow fluid to flow from a first part of the irrigation tube to a second part of the irrigation tube without passing through the portion of the irrigation tube within the trigger mechanism. The trigger mechanism includes a trigger operable by a user. The trigger mechanism can be operable to selectively constrict, close, and open the first irrigation tube to irrigate an area of treatment upon user operation of the trigger. The bypass structure can comprise a flow restriction. A user depression of the trigger can progressively open the irrigation tube. The kidney stone removal mechanism can further comprise a vacuum tube configured to be activated by the trigger mechanism. The kidney stone removal mechanism can further comprise a catheter connected at its proximal end to a distal end of the kidney stone removal mechanism, the catheter having a distal tip at a distal end of the catheter, and
a steering mechanism, located at the proximal end of the kidney stone removal mechanism, the steering mechanism operable to steer the distal tip to facilitate removal of partial or entire kidney stones.

In accordance with another aspect of the invention, a kidney stone removal mechanism is provided comprising an irrigation tube; a vacuum tube; and a flow indicator mechanism including a flow indicator connected to a stone catcher assembly. In an embodiment, the flow indicator can comprise one or more vanes that move in response to fluid or air flow. The kidney stone removal mechanism can further comprise a catheter connected at its proximal end to a distal end of the kidney stone removal mechanism, the catheter having a distal tip at a distal end of the catheter, and a steering mechanism, located at the proximal end of the kidney stone removal mechanism, the steering mechanism operable to steer the distal tip to facilitate removal of partial or entire kidney stones.

In accordance with one aspect, the kidney stone removal mechanism can further comprise a nozzle. The nozzle can include a vacuum lumen in communication with the vacuum tube and sized to remove kidney stones or fragments of kidney stones, and one or more irrigation ports in communication with the irrigation tube, the irrigation ports positioned at a distal end portion of the nozzle and having an irrigation port departure angle in the range of 30 to 60 degrees for directing irrigation fluid forward and laterally from the distal end portion of the nozzle. In an embodiment, at least one of the irrigation ports has a shape of an arc.

In accordance with another aspect of the invention, a kidney stone removal mechanism is provided, comprising a kidney stone removal catheter and a nozzle assembly included at a distal end of the catheter. The nozzle can comprise a vacuum lumen sized to remove kidney stones or fragments of kidney stones, and one or more irrigation ports at a distal end portion of the nozzle. At least one of the irrigation ports has an irrigation port departure angle in the range of 30 to 60 degrees for directing irrigation fluid forward and laterally from the distal end portion of the nozzle. In an embodiment, the kidney stone removal mechanism comprises a first irrigation port configured to direct irrigation fluid forward but not in a radially diverging direction and a second irrigation port configured to direction irrigation fluid in a radially diverging direction. In an embodiment, at least two of the irrigation ports have a different opening size, are of a different shape, and/or have a different irrigation port departure angle. In one embodiment, the first of the irrigation ports is one of circular, elliptical, or arc-shaped and a second of the irrigation ports has a different shape than the first irrigation port and is one of circular, elliptical, or arc-shaped. The first irrigation port can be positioned directly between a second and third irrigation ports, wherein the arc distance between the first and second irrigation ports is different than the arc distance between the first and third irrigation ports.

In an embodiment, the kidney stone removal mechanism additionally comprises an image sensor and a light source. The nozzle can include an upper recess for receiving the image sensor and the light source. The kidney stone removal mechanism can additionally comprise a distal manifold configured to be inserted within a proximal end of the nozzle, the distal manifold having conduits for directing irrigation fluid to the irrigation ports of the nozzle. The kidney stone removal mechanism can additionally comprise a shaft manifold configured to connect to the distal manifold, the shaft manifold having irrigation lumens for channeling irrigation fluid to the conduits of the distal manifold.

The nozzle can include a distal face having radiused or curved edges. The vacuum lumen can be offset from the center of the nozzle. The nozzle can comprise at least one conduit for providing a fluid path between the catheter and the irrigation ports. The at least one conduit can comprise a divider for directing fluid to the irrigation ports.

In accordance with one aspect of the invention, a kidney stone removal system is provided, comprising a vacuum tube and a laser guide configured to be removably inserted into the vacuum tube. The laser guide comprises a tubular body having a lumen configured to receive a laser device, and wings extending from a distal end segment of the tubular body for guiding the distal end segment of the tubular body in the vacuum tube and creating flow gaps between the tubular body and the vacuum tube.

In one embodiment, the tubular body is configured to not extend out of a distal end of the vacuum tube when the tubular body is inserted completely into the vacuum tube and placed in an operational position. In one embodiment, the guide comprises two to four wings. In one embodiment, the guide consists of three or four wings and a circumferential distance is the same between each pair of neighboring wings. In one embodiment, the guide consists of three or four wings and the circumferential distance between a first pair of the neighboring wings is different from a circumferential distance between a second pair of neighboring wings. The first pair and second pair of neighboring wings can share a common wing. In some embodiments, at least two of the gaps have different sizes.

In one embodiment, each wing comprises a middle segment having a rectangular shape, which transitions into tapered end segments that slope downward into the tubular body. In some embodiments, each wing has a variable thickness that increases from a proximal end of the wing to a distal end of the wing along a longitudinal axis. In some embodiments, each wing has a longitudinal axis that is at an angle relative to a longitudinal axis of the tubular body.

In accordance with another aspect of the inventions, the kidney stone removal system additionally comprising an actuator for moving the tubular body within the vacuum tube. In one embodiment, the actuator comprises a biasing element and a shaft coupled to the tubular body, such that actuation of the biasing element causes the shaft to move the tubular body in a back-and-forth direction within the vacuum tube. In one embodiment, the shaft is configured to be removably coupled to a proximal end of the tubular body. In an alternative embodiment, the shaft is permanently attached to a proximal end of the tubular body.

In one embodiment, the biasing element comprises a band coupled to a distal section of the shaft. The actuator can additionally comprise a cylindrical housing coupled to the band and configured to receive the shaft, such that an inward compression and release of the band causes a part of the shaft to telescopically move into and out from the cylindrical housing. The actuator comprises a channel for receiving the laser device. The channel is configured to be in commutation with the lumen of the tubular body.

In accordance with another aspect of the invention, a catheter assembly is provided comprising a vacuum tube and a guiding device configured to be removably positioned in the vacuum tube for receiving a debris fragmentizing device. The guiding device is configured to prevent an unintended movement of the fragmentizing device when the fragmentizing device is positioned at a distal end of the vacuum tube, while allowing fluid and debris to flow past the fragmentizing device and through the vacuum tube. The catheter system can additionally include an actuating device for moving the guiding device within the vacuum tube for clearance of debris. The fragmentizing device can be a laser fiber.

In accordance with another aspect of the invention, a method of kidney stone removal with the use of all of the embodiments of the present inventions is provided. In accordance with an aspect of the invention, methods of kidney stone removal are provided comprising operating kidney stone removal mechanisms as described above and herein.

BRIEF DESCRIPTION OF THE DRAWINGS

Aspects of the present invention now will be described in detail with reference to the accompanying drawings, which are not drawn to scale.

DESCRIPTION

Disclosed herein are systems, devices, and methods for the guided removal of objects in vivo. In particular, the systems, devices, and methods may be adapted to traverse compact areas, such as the urinary tract, and to remove debris, such as kidney stones or fragments of kidney stones, via aspiration through a vacuum tube. As used herein, the term "kidney stones" may refer to fragments of kidney stones, including fragments that have been created by therapeutic fracturing of kidney stones, such as with the device described herein or by another device.

Figure 1:
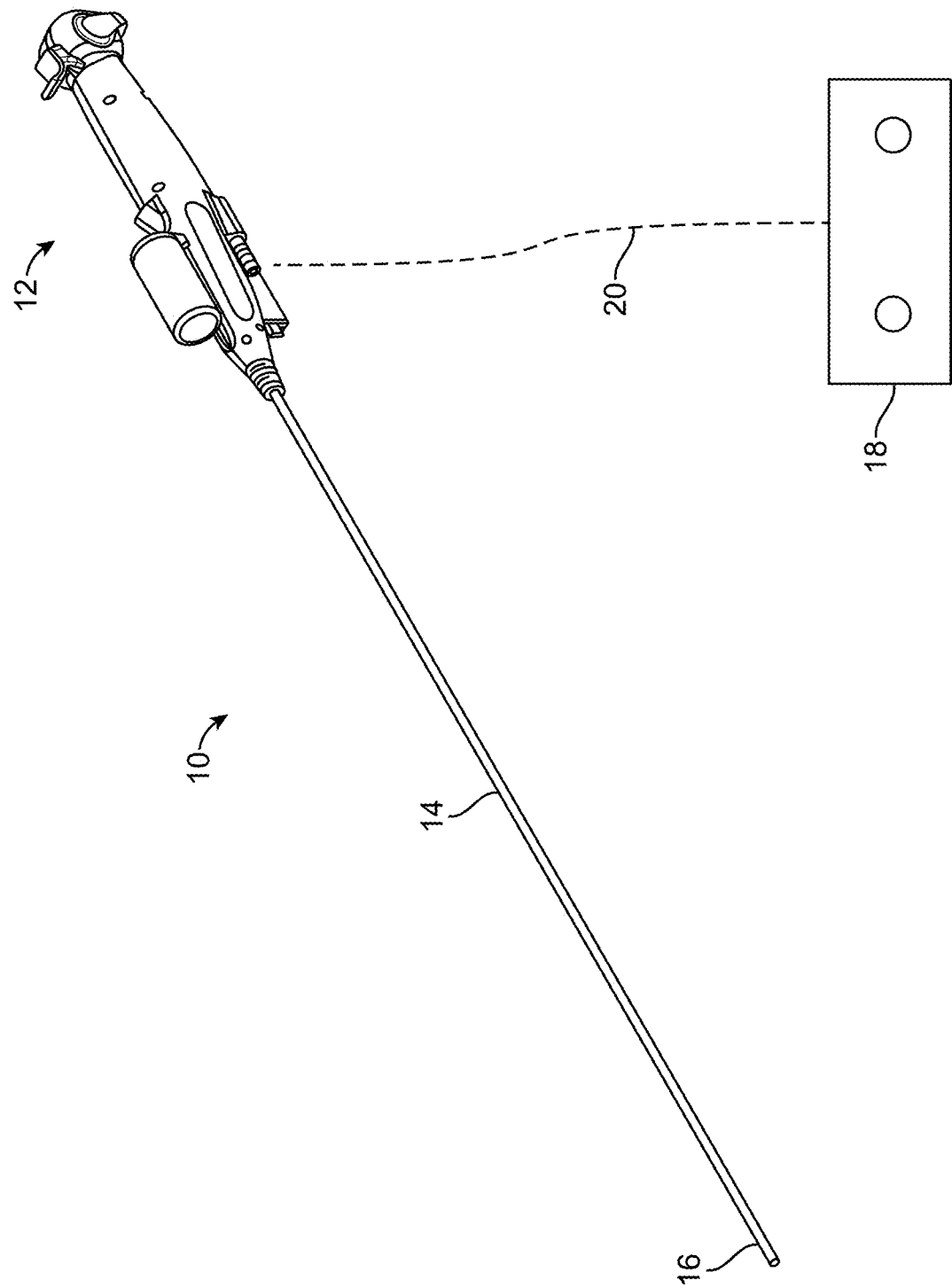
FIG. 1 is a perspective schematic of the kidney stone treatment system according to an embodiment.

FIG. 1 illustrates an embodiment of a treatment system 10 used to remove debris, such as kidney stones. The system 10 includes a handle mechanism 12 from which a catheter 14 extends. The system 10 includes a handle mechanism 12 from which a catheter 14 extends. In the embodiments described below, the handle 12 can be configured to provide, for example, a single trigger design comprising, or consisting of, two modes: an active irrigation mode only (i.e., active irrigation on/vacuum off) and an active irrigation mode in combination with a vacuum mode (i.e., active irrigation on/vacuum on). In the embodiments described below, the handle 12 can be configured to provide, for example, a single trigger design comprising, or consisting of, three modes: passive irrigation on/active irrigation off/vacuum off; passive irrigation on/active irrigation on/vacuum off; passive irrigation on/active irrigation on/vacuum on. In an embodiment, there may be a minimum, passive amount of negative pressure even in the modes where the vacuum is off. Some aspects of the flow design allow for an uninterrupted conduit between the end of the device and the vacuum source such that there is high flow when vacuum is activated and minimal or no flow when vacuum is not activated. The catheter 14 can include various ports and lumens, including a vacuum lumen and an irrigation lumen running along the length of the catheter 14. The system 10 can also include a camera (digital visualization and lighting, e.g., video chip and LED) positioned at an end, distal face or a distal portion of the catheter 14 for providing real time imaging to the physician. A distal assembly 16 is at the distal end of the catheter 14 for irrigation and removal of the debris, with the assistance of the negative pressure applied through the vacuum lumen. The handle mechanism 12 allows the physician to hold and operate the system 10. The handle mechanism 12 can include features that allow a physical to operate various functions of the system, including the camera, vacuum pressure, the amount of irrigation and irrigation pressure, and the maneuverability of the catheter 14. For example, the handle mechanism 12 can include mechanical and electronic controls that allow the physician to adjust the amount of negative pressure, regulate the discharge of the irrigation fluid, and steer the catheter through tortuous anatomical passageways via the use of wheels and/or levers attached to cables, as is well known in the art. The system 10 can be coupled to a control unit 18 via a connector 20. The control unit 18 can control or assist in controlling aspects of the operation of the system 10. For example, the control unit 18 can control or assist in controlling visualization aspects of the system 10. The connector 20 can be a wired connection and/or a wireless connection.

Handle Mechanism

Figure 2:
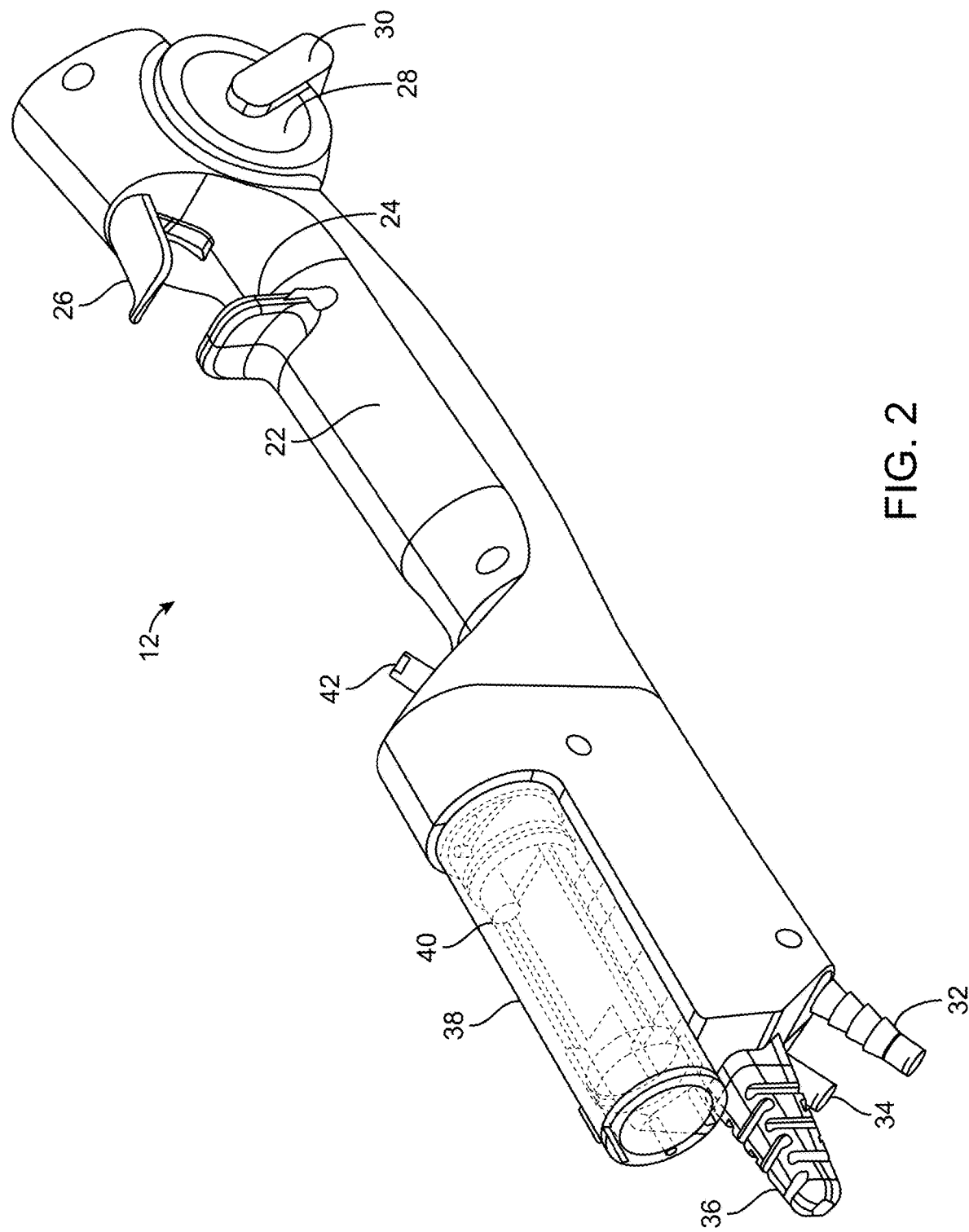
FIG. 2 is a perspective view of a kidney stone removal mechanism according to an embodiment.

FIG. 2 shows the handle mechanism 12 for effecting kidney stone removal according to an embodiment. A finger grip portion 22 runs a portion of a length of the mechanism 12. An optional ledge portion 24 sits over where a user's hand would be while gripping the mechanism 12. Above the optional ledge portion 24 is a trigger 26, which is a part of a trigger mechanism to be described later. The trigger mechanism controls vacuum (or suction) and air flow, as well as irrigation operation of the mechanism 12. A user may operate the trigger 26 with one of their fingers. A distal tip steering control 28 sits at a proximal end portion of the mechanism 12. A user's thumb may control the positioning and/or steering of the distal tip of a catheter by manipulating a lever 30. Various types of catheters may be employed with the mechanism 12, including but not limited to those shown and described in U.S. Pat. No. 11,116,530. U.S. Pat. No. 11,116,530 shows and describes one or more pull wires, which can steer the distal tip of a catheter through manipulation of the lever 30 to which the one or more pull wires may be attached. FIG. 2 also shows a vacuum/suction port 32 and an irrigation port 34, as well as a catheter strain relief 36. A stone catcher receptacle 38 receives extracted kidney stones and/or fragments through a port 40. An access or working channel port 42 permits access to the catheter (not shown) to allow introduction of therapeutic tools such as lasers to the distal end of the catheter.

Figure 5:
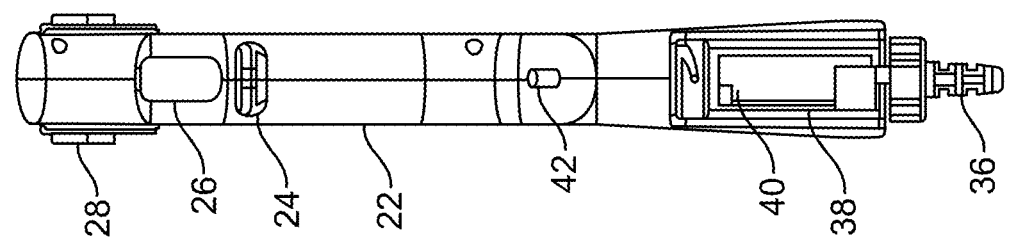
FIG. 5 is a front view of the mechanism shown in FIG. 2.
Figure 4:
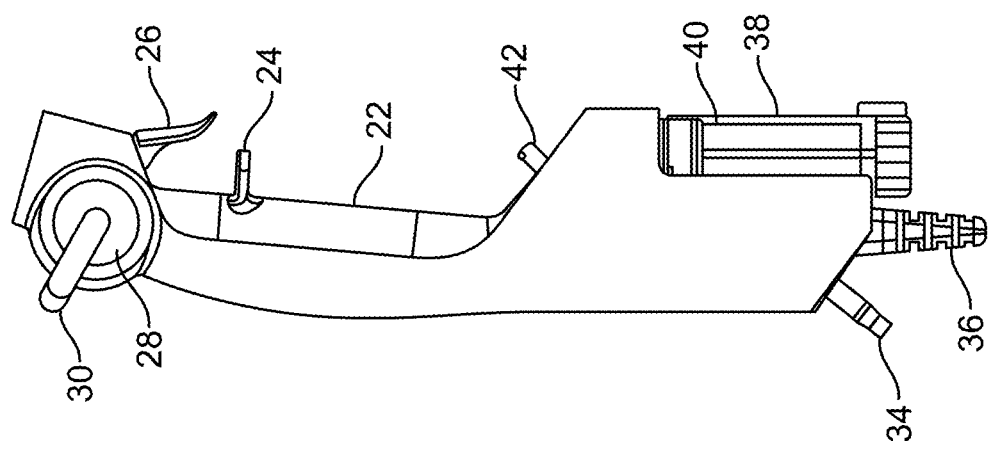
FIG. 4 is a side view of the mechanism shown in FIG. 2.
Figure 3:
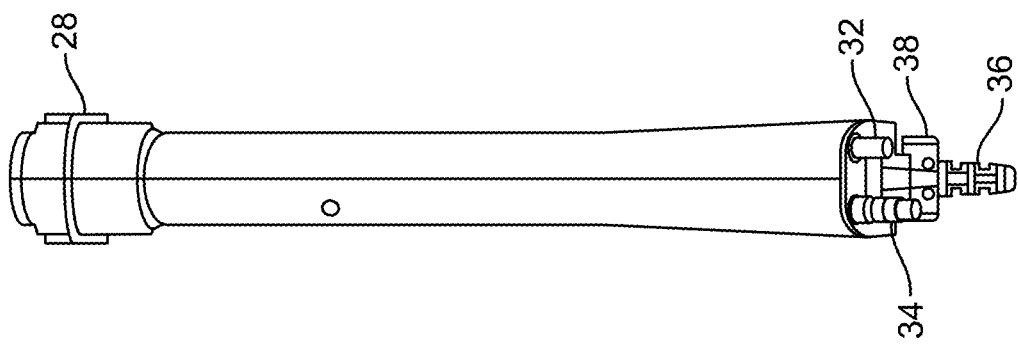
FIG. 3 is a rear view of the mechanism shown in FIG. 2.

FIG. 3 shows a rear view of the handle mechanism 12. In FIG. 3, the vacuum port 32, irrigation port 34, and catheter strain relief 36 are visible, as are the stone catcher receptacle 38 and distal tip steering control 28. FIG. 4 shows a side view of the mechanism 12. In FIG. 4, many of the same elements are visible as in FIG. 2. The finger grip portion 22, with the ledge portion 24 sitting above, fits a user's hand above the access or working channel port 42. The vacuum port 32, irrigation port 34, and catheter strain relief 36 sit at the bottom of the mechanism 12, behind the stone catcher receptacle 38. The port 40, which deposits kidney stones, or fragments or portions of kidney stones, into the stone catcher receptacle 38, also is visible. In FIG. 5, which is a front view of the mechanism 12, many of the same elements are visible as in FIG. 2. The finger grip portion 22, with the ledge portion 24 sitting above, fits a user's hand above the access or working channel port 42. The catheter strain relief 36 sits at the bottom of the mechanism 12, behind the stone catcher receptacle 38. The port 40, which deposits kidney stones or portions of kidney stones into the stone catcher receptacle 38, also is visible.

Figure 6:
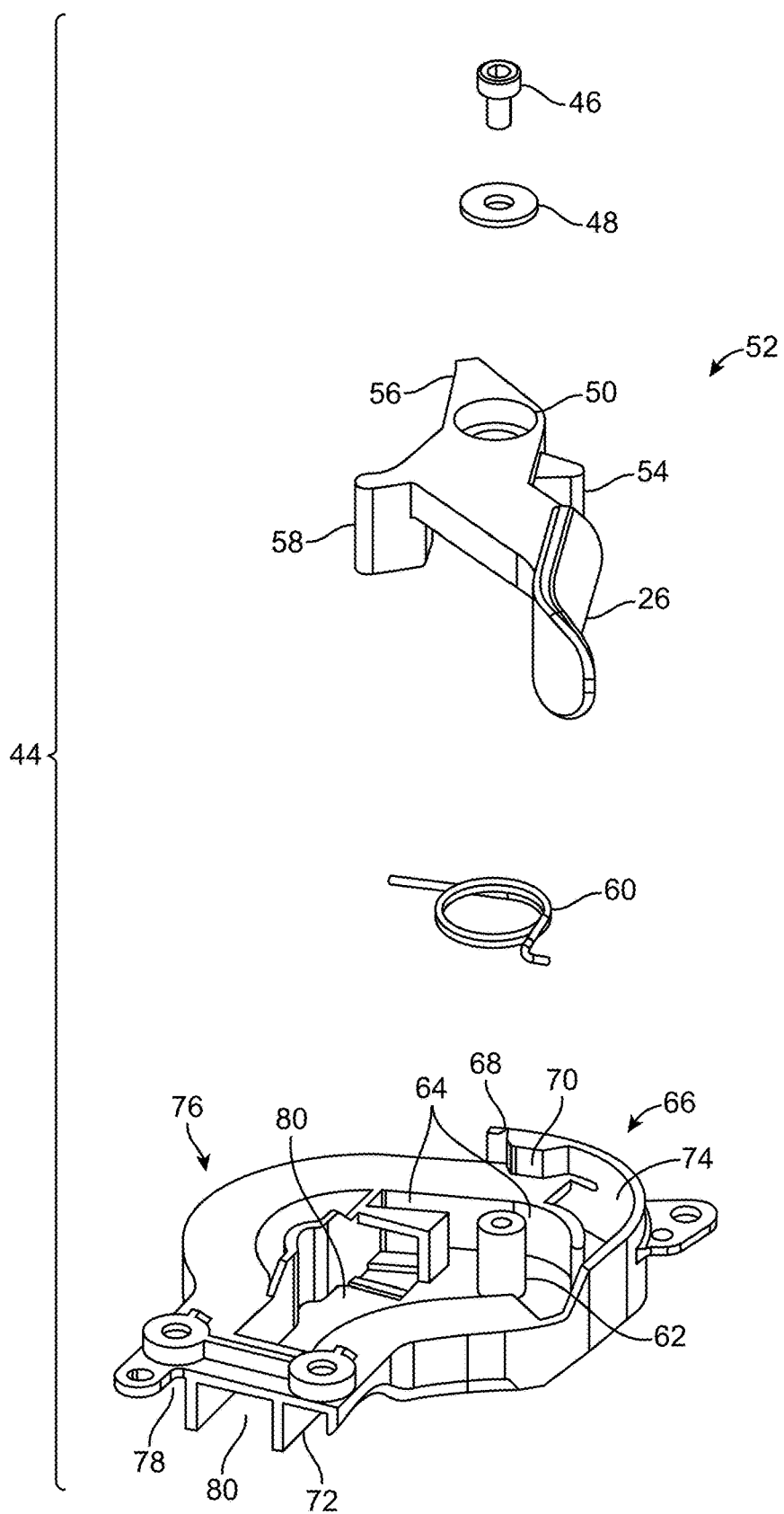
FIG. 6 is an exploded view of a trigger activation mechanism according to an embodiment.

FIG. 6 is an exploded view of a portion at the top of the mechanism 12. Collectively, the parts in FIG. 6 constitute a trigger mechanism assembly 44. Going from top to bottom in FIG. 6, a screw or bolt 46 passes through a washer 48 and opening 50 of a trigger mechanism 52. The trigger mechanism 52 includes protrusions 54, 56, and 58. The function of these protrusions during actuation of the trigger mechanism 52 will be described in more detail below with respect to FIGS. 7-9. The screw or bolt 46 also passes through a spring 60 or other resilient device and is received by a screw/bolt receptacle 62. In some examples, the bolt 46 holds the trigger securely to a base plate boss that captures the spring 60. The spring 60 provides resilience for the trigger mechanism 52, so that the trigger mechanism 52 returns to its original, home position when a user releases or removes pressure from the trigger 26. The spring 60 or other resilient device sits in opening 64 of a mechanism casing or body 66. The mechanism body 66 also includes first and second detents 68 and 70, whose function will be described in more detail below with respect to FIGS. 7-9. In some examples, the mechanism body 66 may contain more or fewer detents. When the handle mechanism 12 is assembled, mechanism casing 66 is not visible. In FIG. 6 and in subsequent figures, the mechanism casing 66 is exposed for ease of description of the function of the trigger mechanism 52. An irrigation tube (not shown) enters through opening 72, proceeds through opening 74, under a covering portion 76, and exits through an opening 78. A vacuum activation tube (not shown) sits inside the mechanism casing 66, and exits through opening 80.

Figure 35:
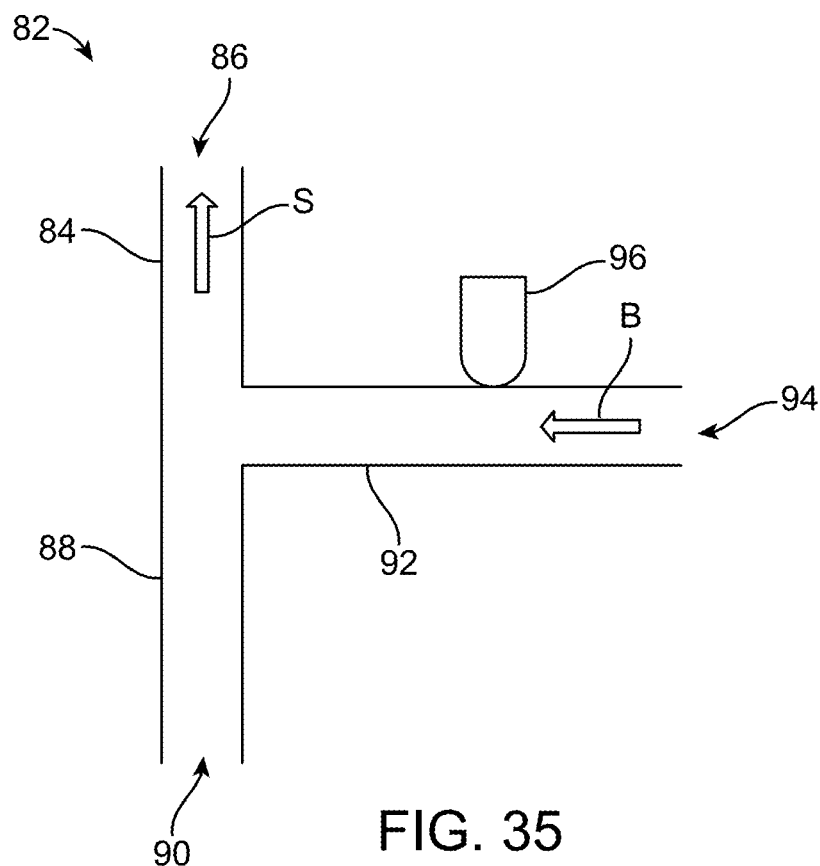
FIGS. 35 and 36 show schematic diagrams of a vacuum/suction control system and method according to an embodiment.
Figure 36:
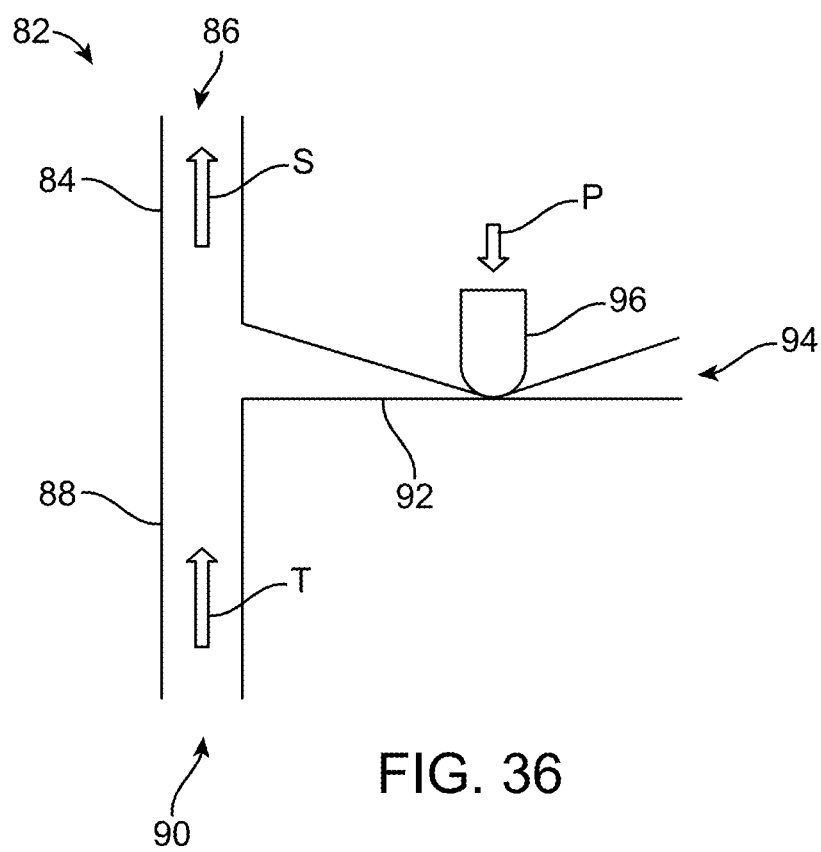

Advancing to FIGS. 35 and 36, they show schematic diagrams of a vacuum/suction control system and method 82. A suction outlet tube 84 includes a suction opening 86, which is connected to a vacuum/suction source (not pictured). Flow through the suction outlet tube 84 is in the direction of arrow S. A suction target tube 88 includes a target opening 90, which is connected to a portion of the device that is in proximity of an area targeted for suction/vacuum. FIG. 36 shows a configuration in which flow through suction target tube 88 is in the direction of arrow T. An activation tube 92 includes an activation opening 94, which is open to ambient air. An activation pinch mechanism 96 is positioned adjacent to the activation tube 92 and is movable in the direction of arrow P from first position that allows flow in the direction of arrow B through the activation tube 92 (shown in FIG. 35) and a second position that prevents flow from activation opening 94 through activation tube 92 (shown in FIG. 36). The system and method 82 shows that the activation pinch mechanism 96 allows for control over the vacuum/suction flow. The vacuum source (not pictured) can be set to a provide a constant amount of suction (e.g., 200 mmHg) and the activation pinch mechanism 96 provides for on/off control over the vacuum/suction by opening or closing the activation tube 92. In the configuration shown in FIG. 35, the activation pinch mechanism 96 is positioned such that air flows through the activation tube 92 in the direction of arrow B, through the suction outlet tube 84 in the direction of arrow S, and out to the vacuum/suction source. In the configuration shown in FIG. 35, little or no flow is through the suction target tube 88 from the targeted area to the suction outlet tube 84. In the configuration shown in FIG. 35, there is no (or comparatively little) suction applied to the target area and vacuum is off at the target area. In the configuration shown in FIG. 36, the activation pinch mechanism 96 is positioned such that no air flows through the activation tube 92. In the configuration shown in FIG. 36, all the flow is through the suction target tube 88 from the targeted area in the direction of arrow T to the suction outlet tube 84 and out the suction opening 86 in the direction of arrow S. In the configuration shown in FIG. 36 vacuum is on at the target area.

Figure 7:
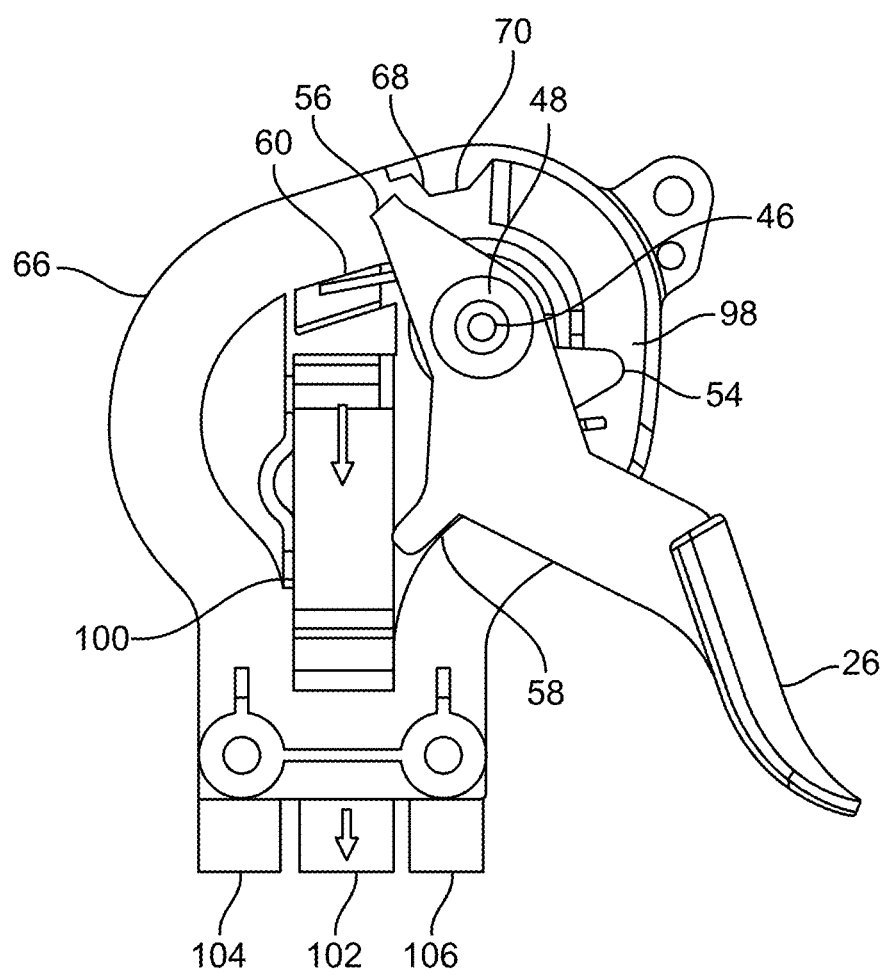
FIGS. 7 to 9 show successive positions of a trigger according to an embodiment.
Figure 8:
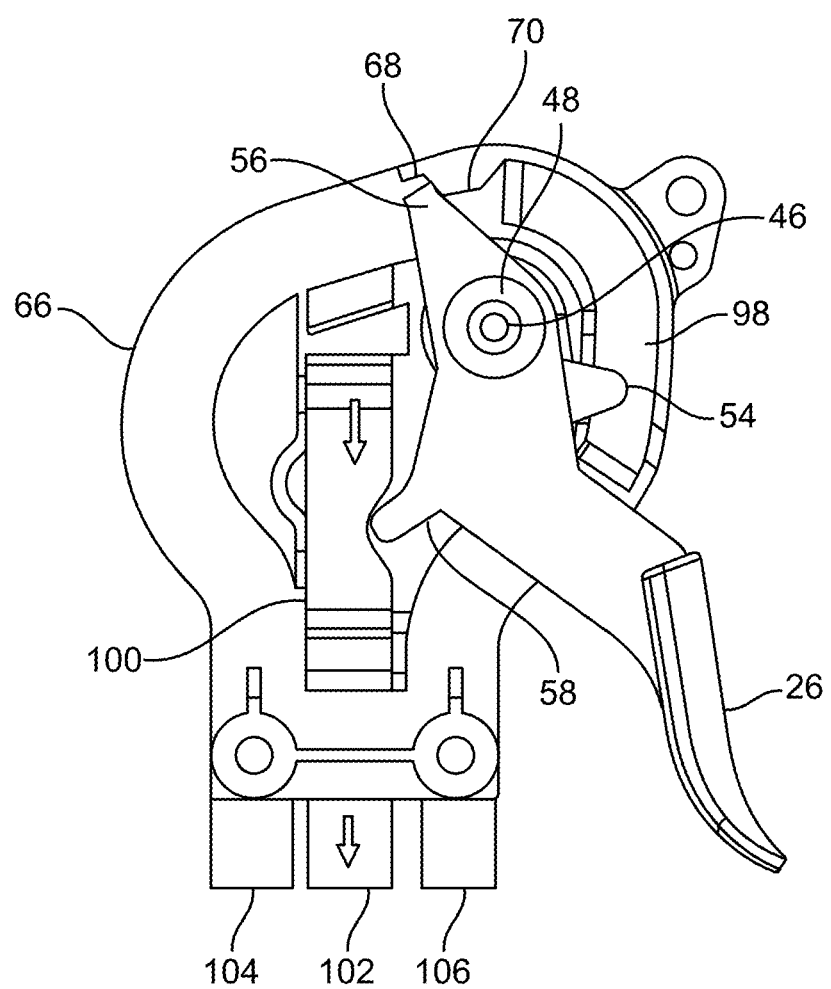
Figure 9:
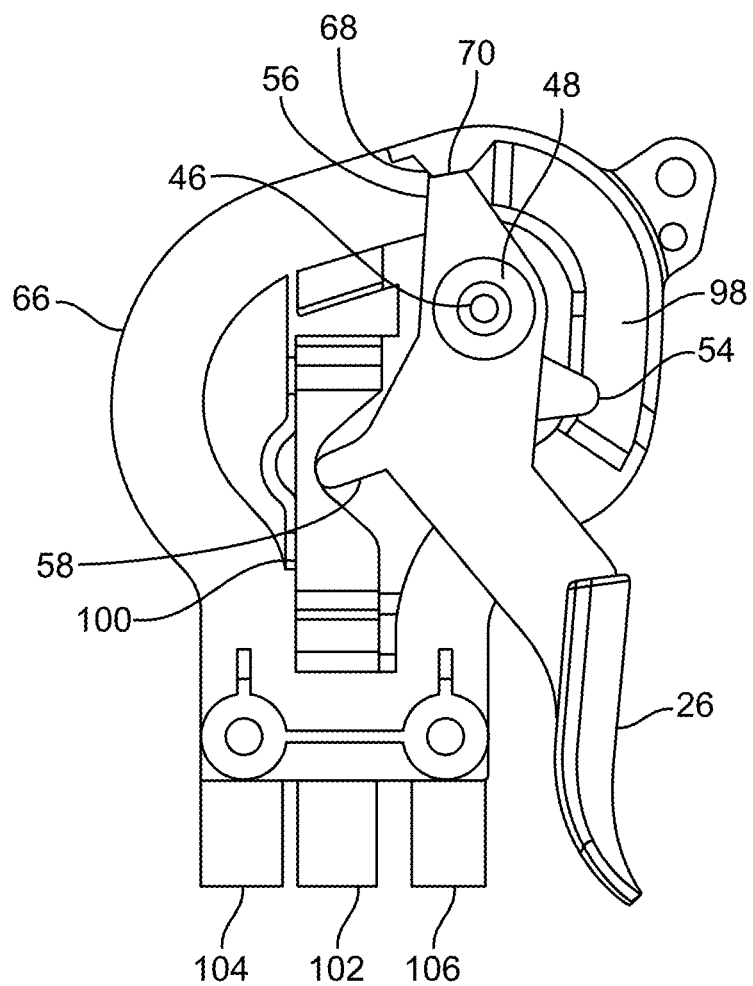
Figure 10:
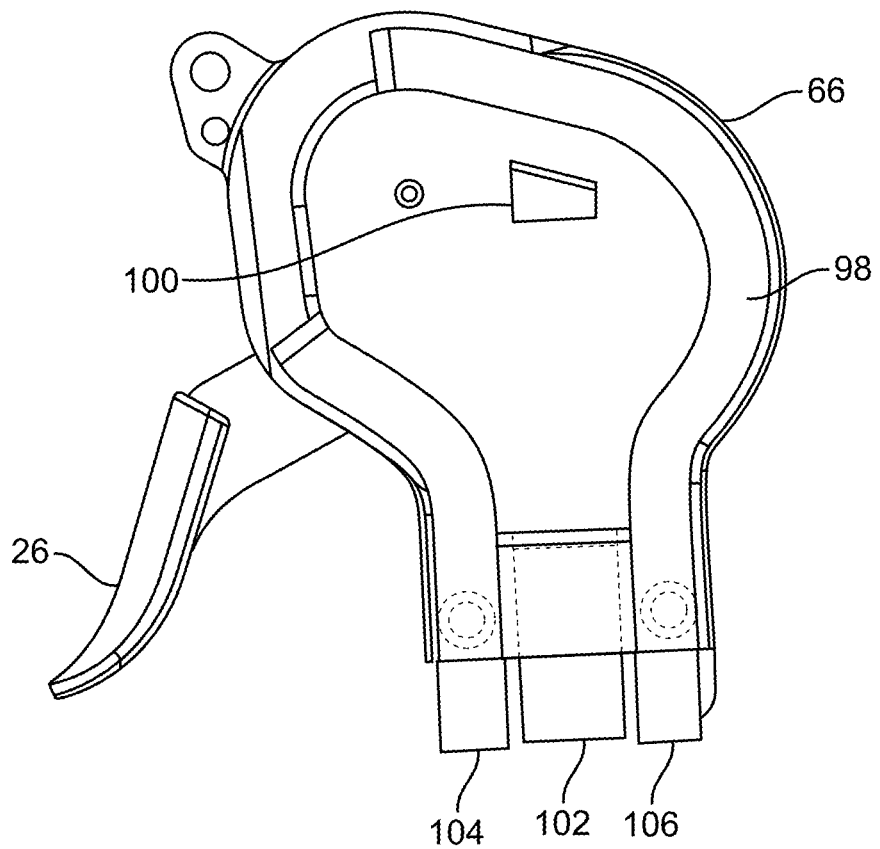
FIG. 10 is a reverse view of a trigger activation mechanism according to an embodiment.

FIGS. 7-9 show successive positions of the trigger 26. In FIG. 6, the trigger 26 is in the undepressed position. With the trigger 26 in that position, the vacuum and irrigation in the handle mechanism 12 are turned off. In some examples, an irrigation bypass structure may allow for a minimum amount of irrigation to flow even when trigger 26 is in the undepressed position. The protrusion 54 pinches off an irrigation tube 98. The protrusion 56 is not in contact with the detent 68. The protrusion 58 may contact, but does not compress, a vacuum activation tube 100 (see also, for example, the activation tube 92 of FIGS. 35 and 35). The vacuum activation tube 100 is open to ambient air at one end and connected at an end 102 with vacuum tubing running from a vacuum source to a vacuum lumen running to the vacuum target area. The spring 60 or other resilient device engages the trigger mechanism 52 resiliently so that, when the user releases the trigger 26, the trigger 26 returns to its initial position, so that irrigation and vacuum are turned off. In some embodiments, irrigation is partially on at a minimum level and vacuum is off when the trigger 26 returns to its initial position. In FIG. 8, the trigger 26 is partly depressed, up to the point that the protrusion 56 contacts detent 68 in the mechanism body 66, indicating to the user that a first stopping point in operation has been reached. With the trigger 26 in this position, the protrusion 54 partly disengages with the irrigation tube 98, opening the irrigation tube 98 slightly, and allowing for some irrigation (or, in some embodiments, full irrigation flow). The protrusion 58 partly closes off the vacuum activation tube 100, but air still can flow through the vacuum activation tube 100, so vacuum at the target area still is off. In FIG. 9, the trigger 26 is fully depressed. The protrusion 56 proceeds past the detent 68 and seats up against the detent 70. In this position, the protrusion 58 pinches off the vacuum activation tube 100, thereby turning the vacuum on at the target area. The protrusion 54 opens the irrigation tube 98 further, so that irrigation continues, and kidney stones and/or pieces of kidney stones can be removed and deposited in the stone catcher receptacle 38 (FIGS. 2-5). FIG. 10 shows a view of the mechanism body 66 from an opposite side to those shown in FIGS. 7-9. The irrigation tube 98 has an inlet 104 and an outlet 106. The activation tube 100 runs through the mechanism body 66. The trigger 26 has protrusions (not shown) which interact with the irrigation tube 98 and the activation tube 100 according to a degree of depression of the trigger 26. In the foregoing descriptions of kidney stone removal mechanism, the function of the inlet 104 and the outlet 106 can be reversed, so that element 104 operates as an irrigation outlet, and element 106 operates as an irrigation inlet.

Figure 11:
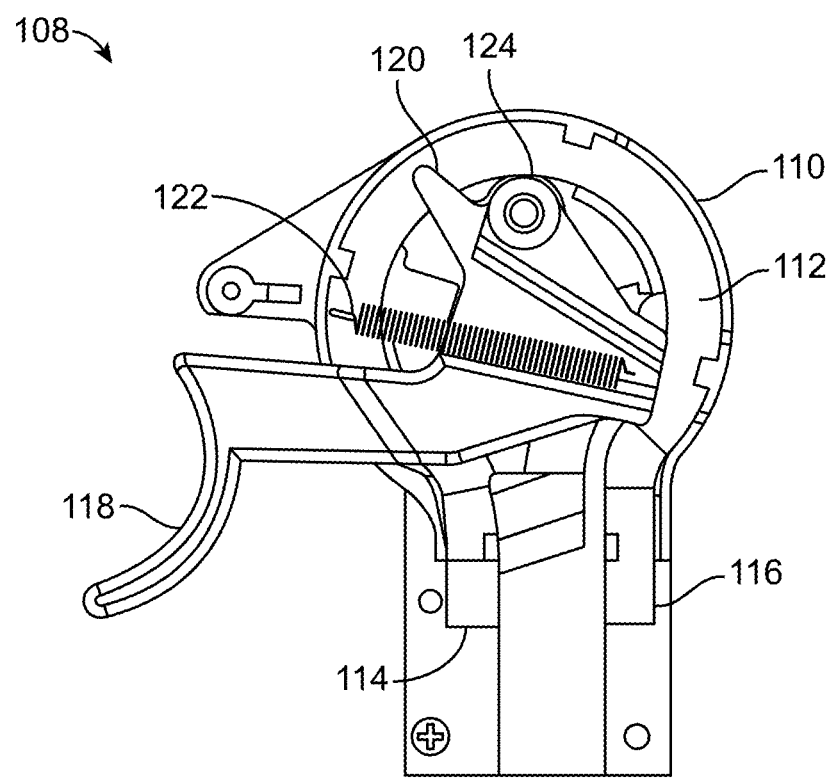
FIGS. 11 and 12 show successive positions of a trigger in a trigger activation mechanism according to an embodiment.
Figure 12:
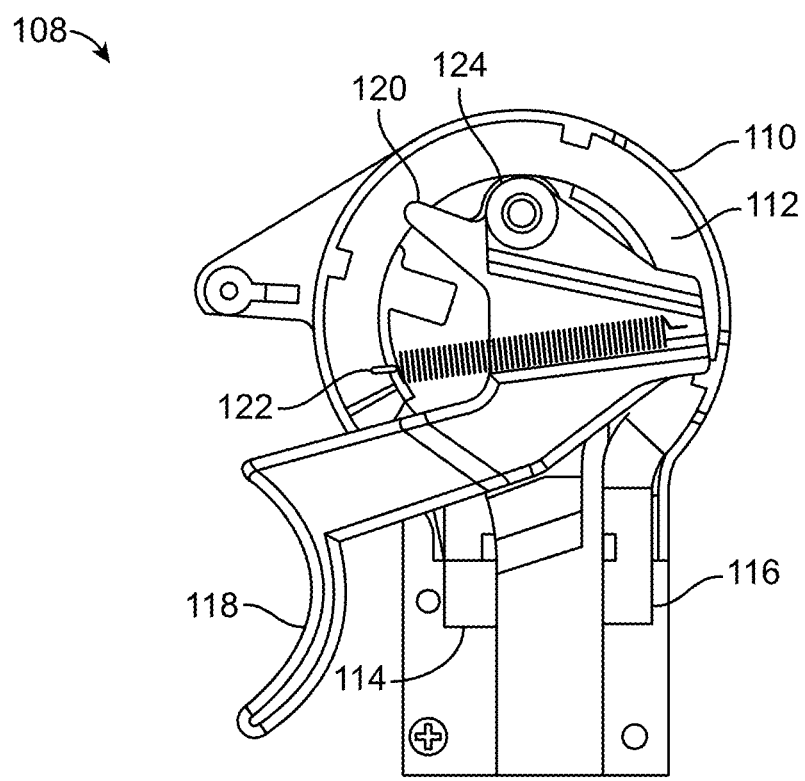
Figure 13:
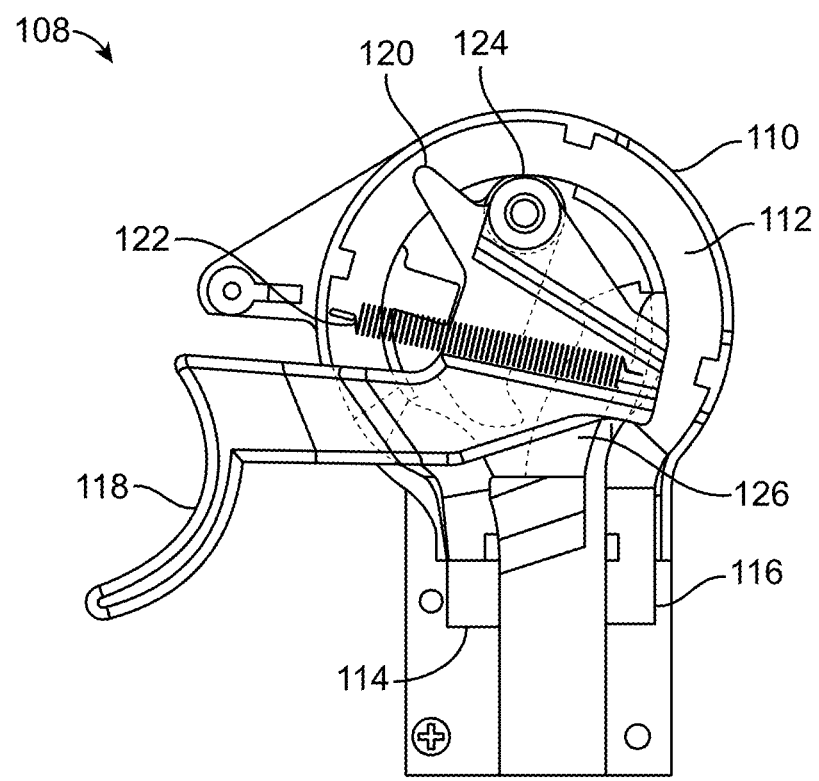
FIGS. 13 and 14 show successive positions of a trigger in a trigger activation mechanism according to an embodiment.
Figure 14:
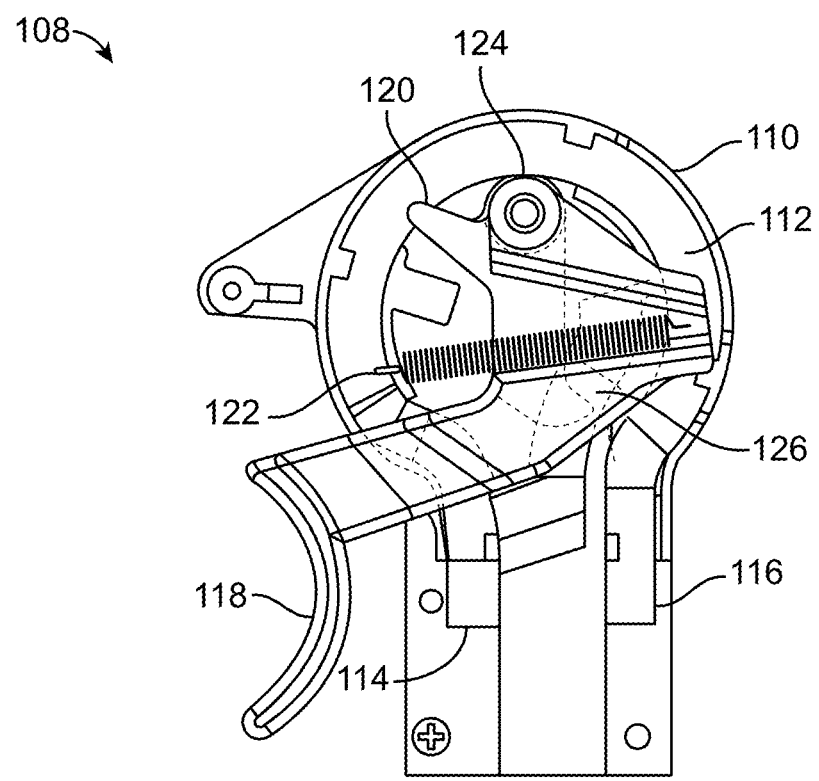

FIG. 11 shows a portion of a kidney stone removal mechanism 108 according to an embodiment. A mechanism casing or body 110 contains an irrigation tube 112 with an irrigation inlet 114 and an irrigation outlet 116. A trigger 118 has a protrusion 120 which interacts with the irrigation tube 112. When the trigger 118 is undepressed, as shown in FIG. 11, the protrusion 120 closes off, or at least constricts, the irrigation tube 112. A spring 122 or other resilient device moves against the force of a user depression of trigger 118 to return the trigger 118 to its undepressed state when the user releases the trigger 118. When depressed, the trigger 118 rotates around a pivot point 124, causing the protrusion 120 to move away from the irrigation tube 112 to open the tube and enable irrigation. FIG. 12 shows structure similar to that in FIG. 11, except that in FIG. 12, the trigger 118 is depressed, so that the protrusion 120 moves away from the irrigation tube 112 to open it up. FIG. 13 shows structure similar to that in FIG. 11, but from an opposite side of the mechanism body 110. The trigger 118 is in the same position in FIG. 13 as in FIG. 11. When the trigger 118 is in this position, a vacuum tube (not shown) in position 126 will not be pinched, so that vacuum or suction will be off. Comparing FIG. 13 with FIG. 11, when vacuum or suction is off, so is irrigation. FIG. 14 shows structure similar to that in FIG. 13, except that in FIG. 14, the trigger 118 is depressed, so that the vacuum tube (not shown) in position 126 will be pinched, so that vacuum or suction will be on. Comparing FIG. 14 with FIG. 12, when vacuum or suction is on, so is irrigation, similarly to other described embodiments.

Unlike the embodiment of FIGS. 7 to 9, FIGS. 11 to 14 do not show an intermediate depression position for the trigger 118. However, ordinarily skilled artisans will appreciate that kidney stone removal mechanism 108 enables a range of depression positions for trigger 118. Accordingly, similarly to the embodiment of FIGS. 7 to 9, there is an intermediate depression for the trigger 118, whereby the irrigation tube 112 will be slightly un-pinched, allowing irrigation to flow, while the vacuum tube (not shown) will be slightly pinched, so that vacuum or suction still will be off.

Figure 15:
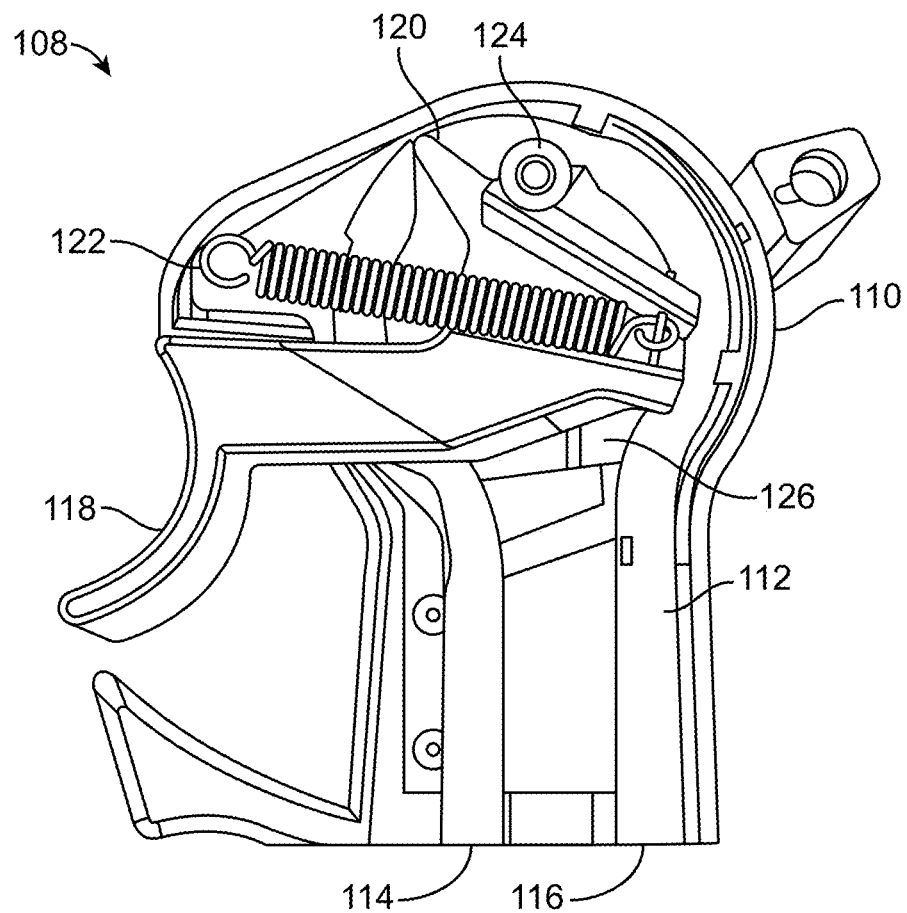
FIG. 15 is a picture of a trigger activation mechanism according to an embodiment.

FIG. 15 is a photograph of a portion of the kidney stone removal mechanism 108, similar to the structure in FIG. 11, according to an embodiment. The mechanism body 110 contains the irrigation tube 112 with the irrigation inlet 114 and the irrigation outlet 116. The trigger 118 has the protrusion 120 which interacts with the irrigation tube 112. When the trigger 118 is undepressed, as shown in FIG. 15, the protrusion 120 closes off, or at least constricts, the irrigation tube 112. The spring 122 or other resilient device moves against the force of a user depression of the trigger 118 to return the trigger 118 to its undepressed state when the user releases the trigger 118. When depressed, the trigger 118 rotates around the pivot point 124, causing the protrusion 120 to move away from the irrigation tube 112 to open up the tube and enable irrigation. The trigger 118 is in the same position in FIG. 15 as in FIG. 13. When trigger 118 is in this position, a vacuum tube (not shown) in position 126 will not be pinched, so that vacuum or suction will be off. When vacuum or suction is off, so is irrigation. In the foregoing descriptions, the function of the inlet 114 and the outlet 116 can be reversed, so that element 114 operates as an irrigation outlet, and element 116 operates as an irrigation inlet.

Figure 16:
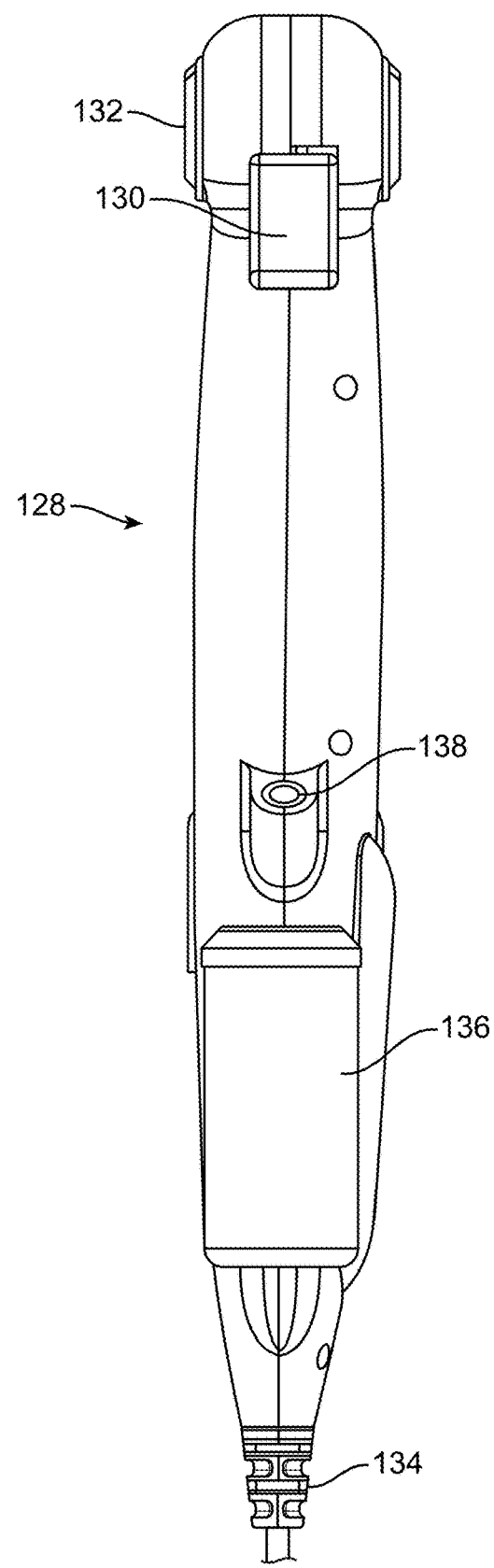
FIG. 16 is a front view of the kidney stone removal mechanism of an embodiment.
Figure 17:
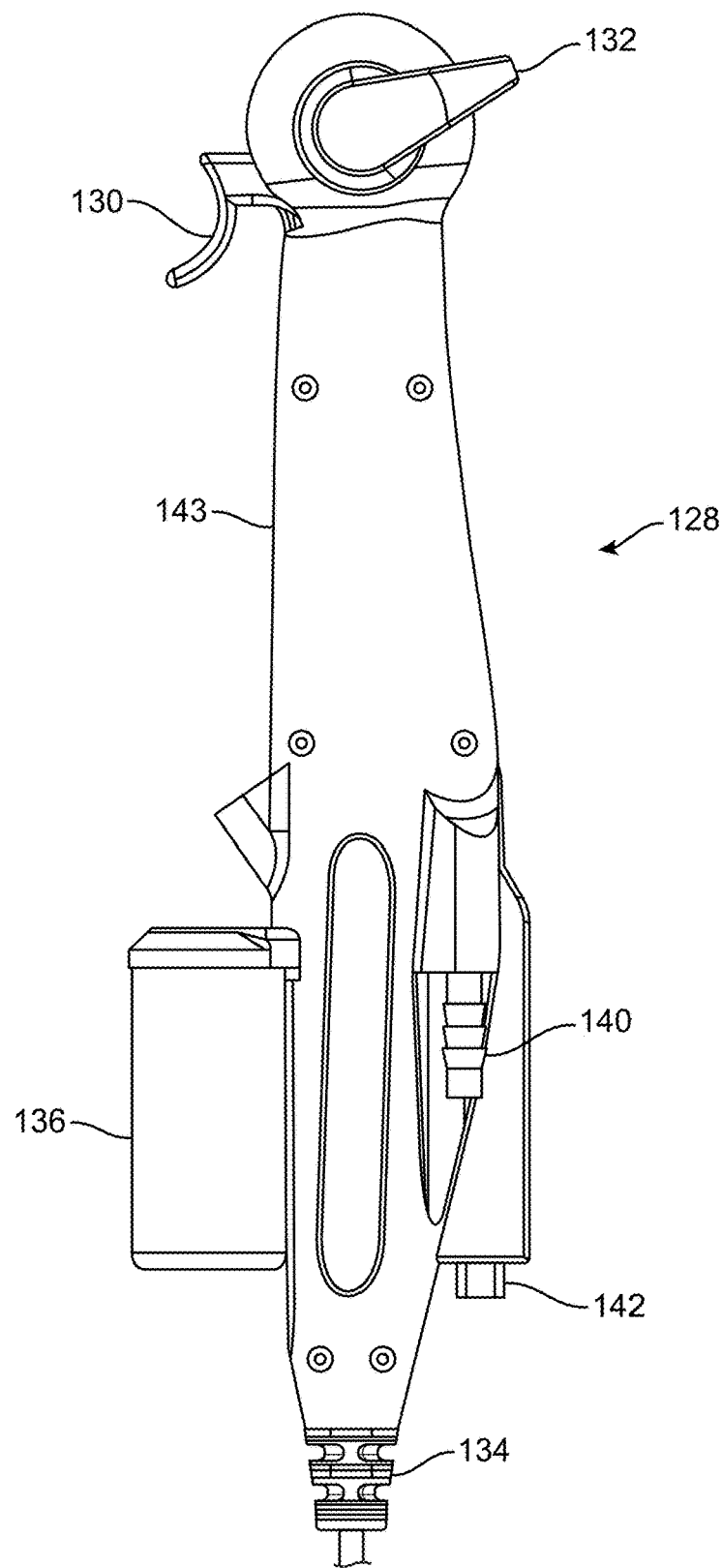
FIG. 17 is a side view of the kidney stone removal mechanism of an embodiment.
Figure 18:
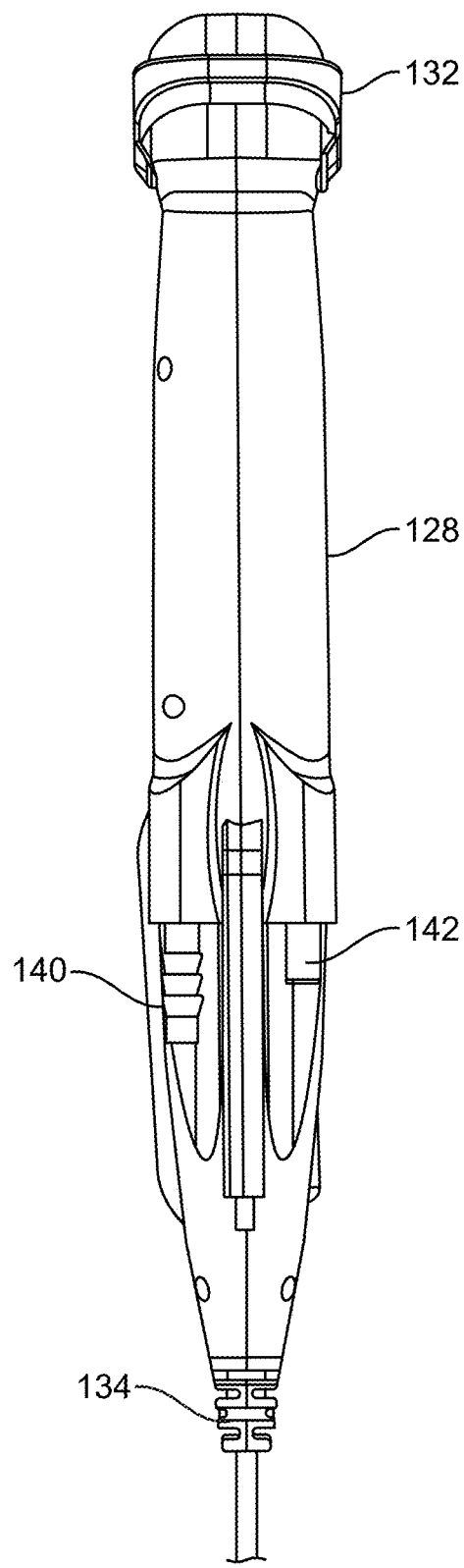
FIG. 18 is a rear view of the kidney stone removal mechanism of an embodiment.
Figure 19:
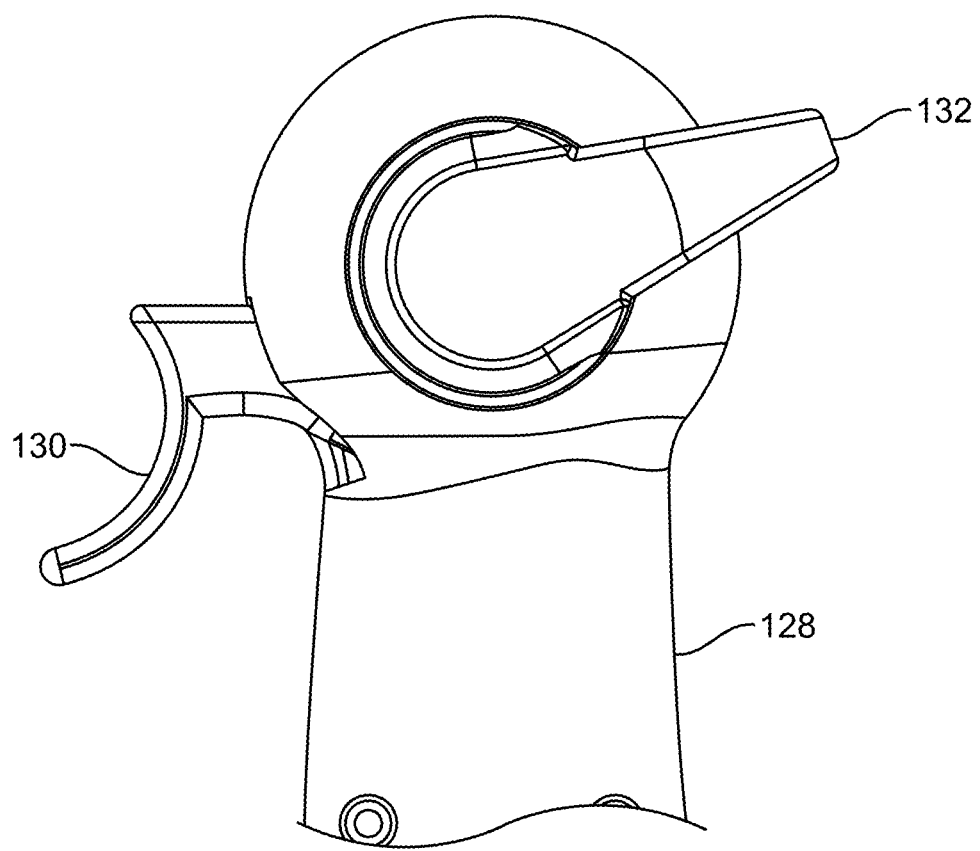
FIGS. 19 to 21 show successive positions of a trigger according to an embodiment.
Figure 20:
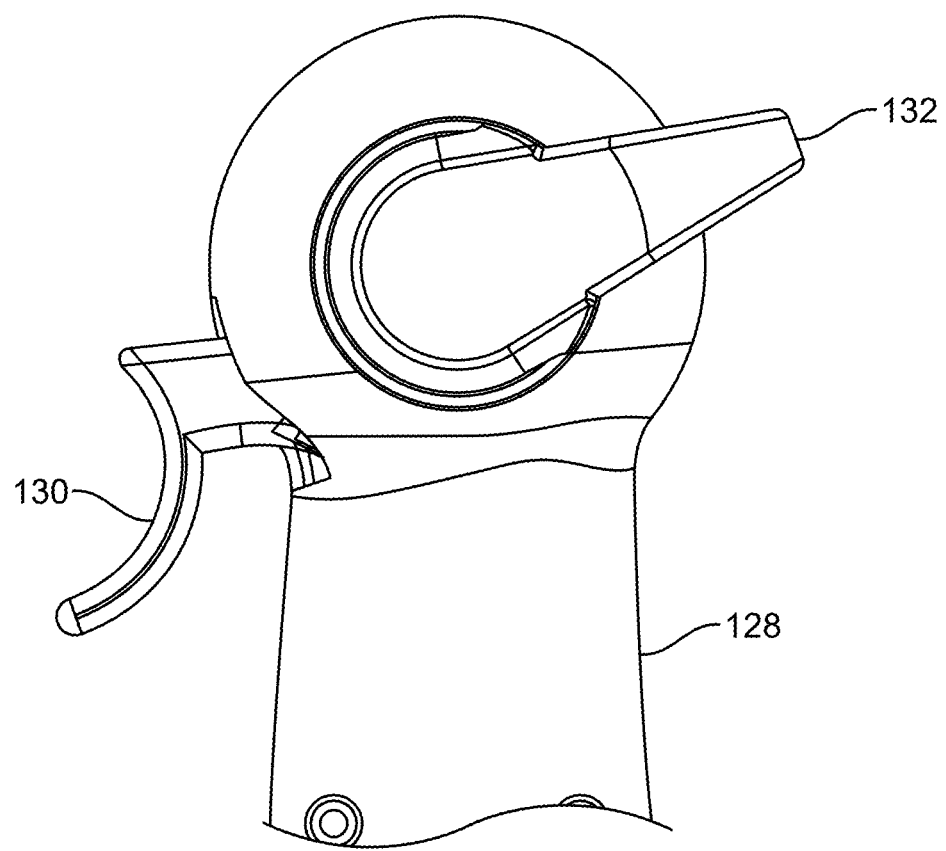
Figure 21:
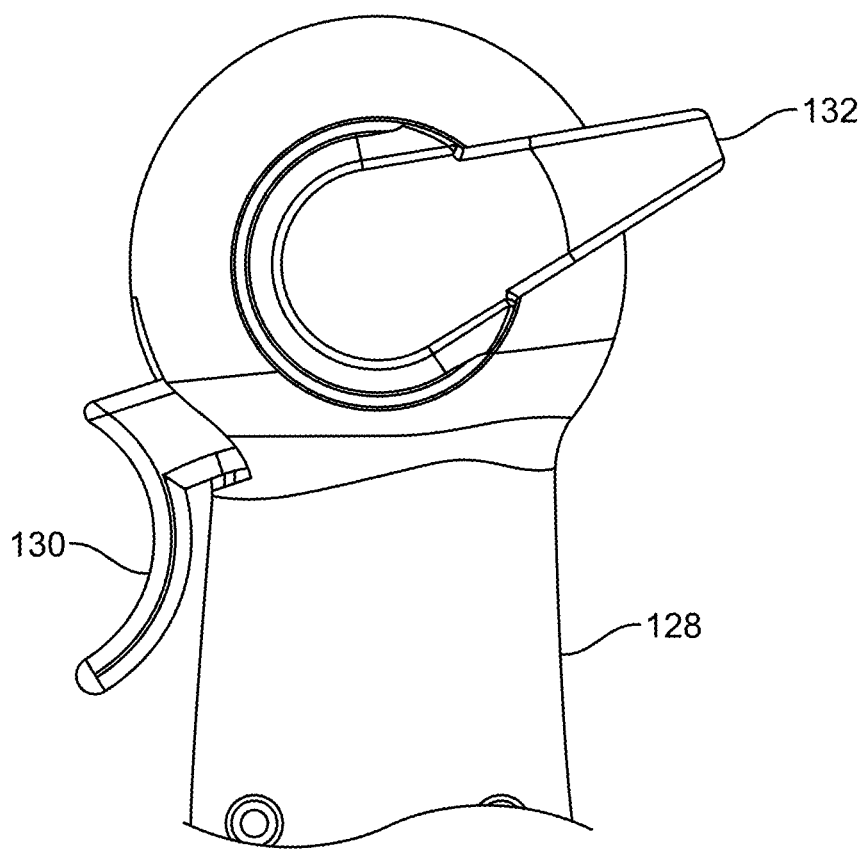
Figure 22:
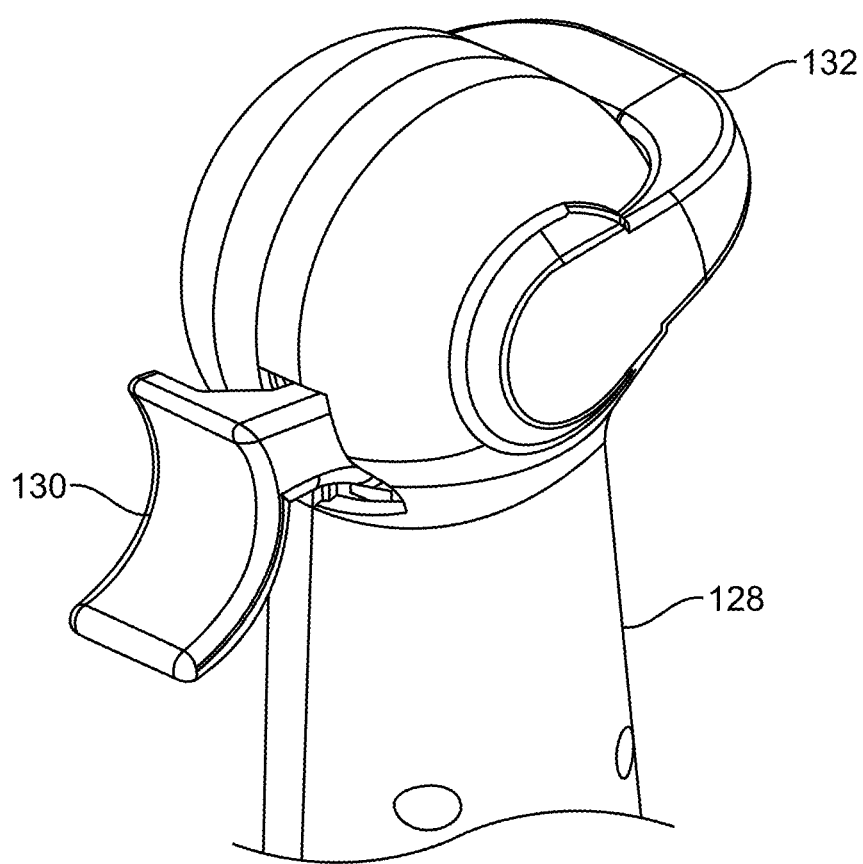
FIG. 22 is a close-up perspective view of the trigger and a distal tip control mechanism in FIGS. 16 to 21.

FIGS. 16-22 show a kidney stone removal mechanism 128 according to an embodiment. A finger grip portion runs a portion of the length of mechanism. A trigger mechanism 130 is located at a proximal end of the kidney stone removal mechanism 128. A distal tip steering mechanism 132, also located at a proximal end of the kidney stone removal mechanism 128, enables manipulation of a catheter, particularly a distal end of a catheter, to position the distal end as desired for kidney stone fracture and/or removal. The catheter is connected to catheter strain relief 134. A stone catcher receptacle 136 receives removed kidney stones and/or pieces thereof. A working channel port 138 permits access to the catheter for insertion of devices and tools. In FIG. 16, showing a front view of the kidney stone removal mechanism 128, there is a more detailed view of the catheter strain relief 134. There also is a front view of the stone catcher receptacle 136. The access or working channel port 138 permits access to a catheter to allow introduction of therapeutic tools such as lasers to the distal end of the catheter. FIG. 16 also shows a front view of the trigger 130, and a side view of the distal tip steering mechanism 132. FIG. 17 shows a side view of the kidney stone removal mechanism 128. A vacuum outlet 140 and irrigation inlet 142 are visible, as well as the catheter strain relief 134, the stone catcher receptacle 136, and a finger grip 143. In FIG. 18, showing a rear view of the kidney stone removal mechanism 128, the vacuum outlet 140 and the irrigation inlet 142 are visible, as is the catheter strain relief 134. The distal tip steering mechanism 132 also is visible. FIGS. 19-21 show close ups of successive positions of the trigger 130 of the kidney stone removal mechanism 132, from undepressed in FIG. 19 to fully depressed in FIG. 21. FIG. 22 shows a perspective side view of FIGS. 19-21.

Figure 23:
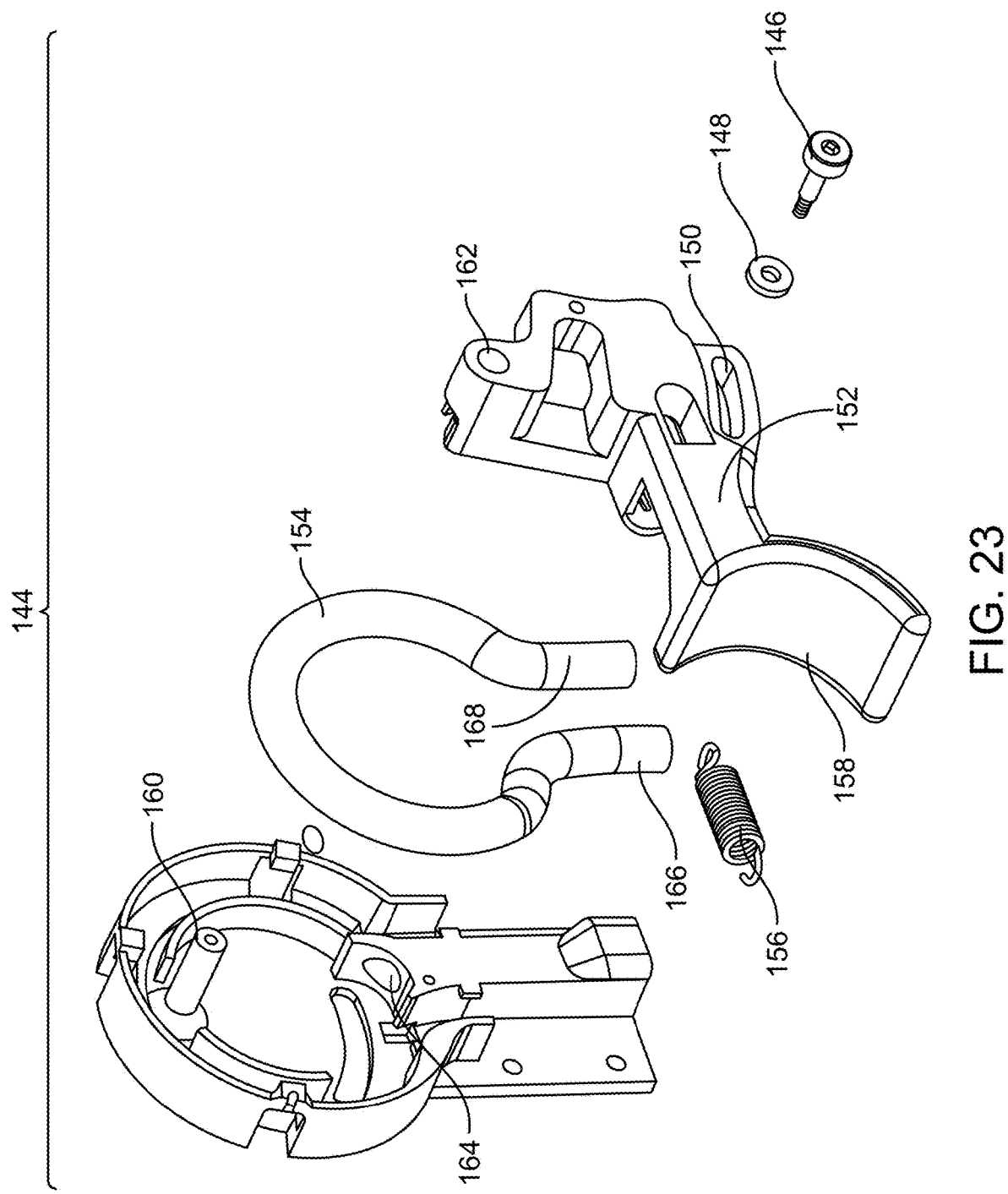
FIG. 23 is an exploded view of a trigger mechanism according to an embodiment.
Figure 24:
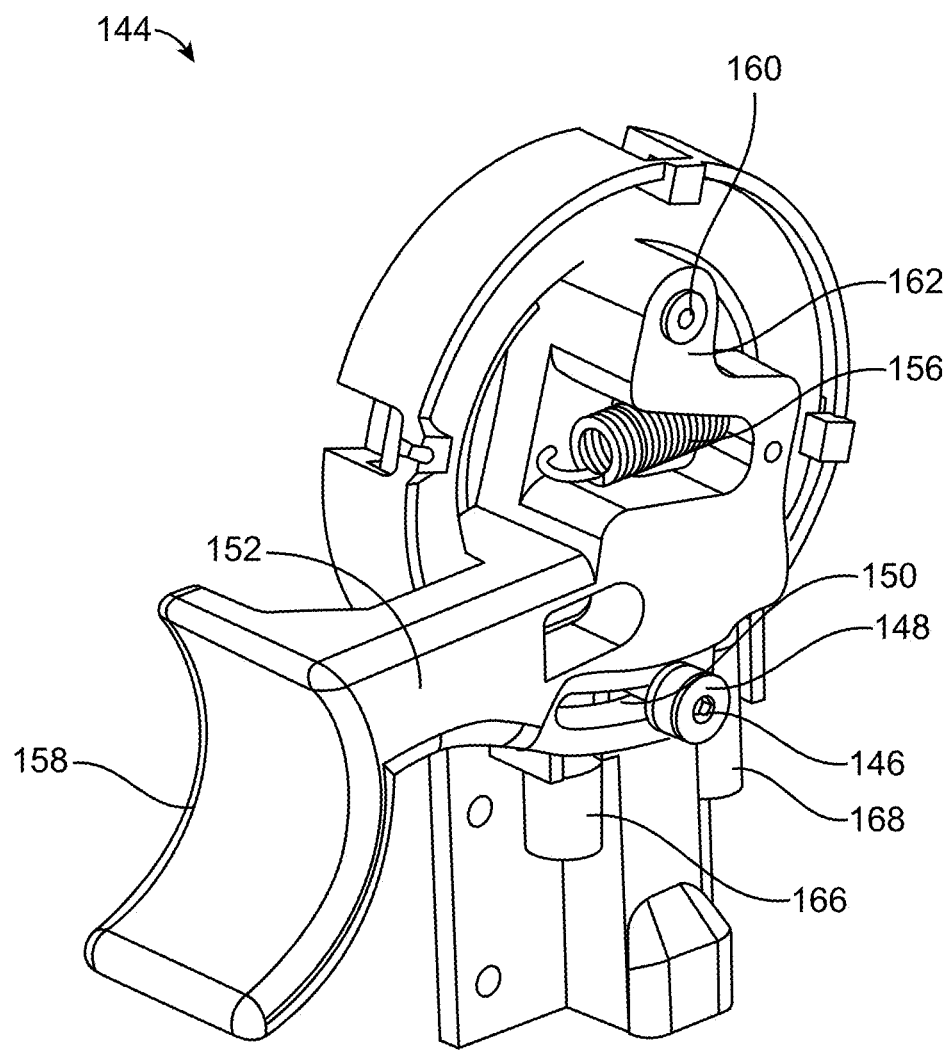
FIG. 24 is an assembled view of the trigger mechanism of FIG. 23.

FIG. 23 shows an exploded view of a trigger mechanism assembly 144 according to an embodiment. A bolt 146 and a washer 148 pass through a slot 150 in a trigger mechanism 152. An irrigation tube 154 has an irrigation inlet and irrigation outlet 166 and 168. A spring 156 biases a trigger 158 toward an undepressed position. A pivot 160 receives the trigger mechanism 152 by fitting through a hole 162 in the trigger mechanism 152. When a user actuates the trigger 158, the trigger mechanism 152 rotates around the pivot 160. An opening 164 leads to a vacuum outlet (not shown). FIG. 24 shows an assembled version of the trigger mechanism of FIG. 23. Elements discussed above with respect to FIG. 23 are depicted with the same reference numerals in FIG. 24.

Figure 25:
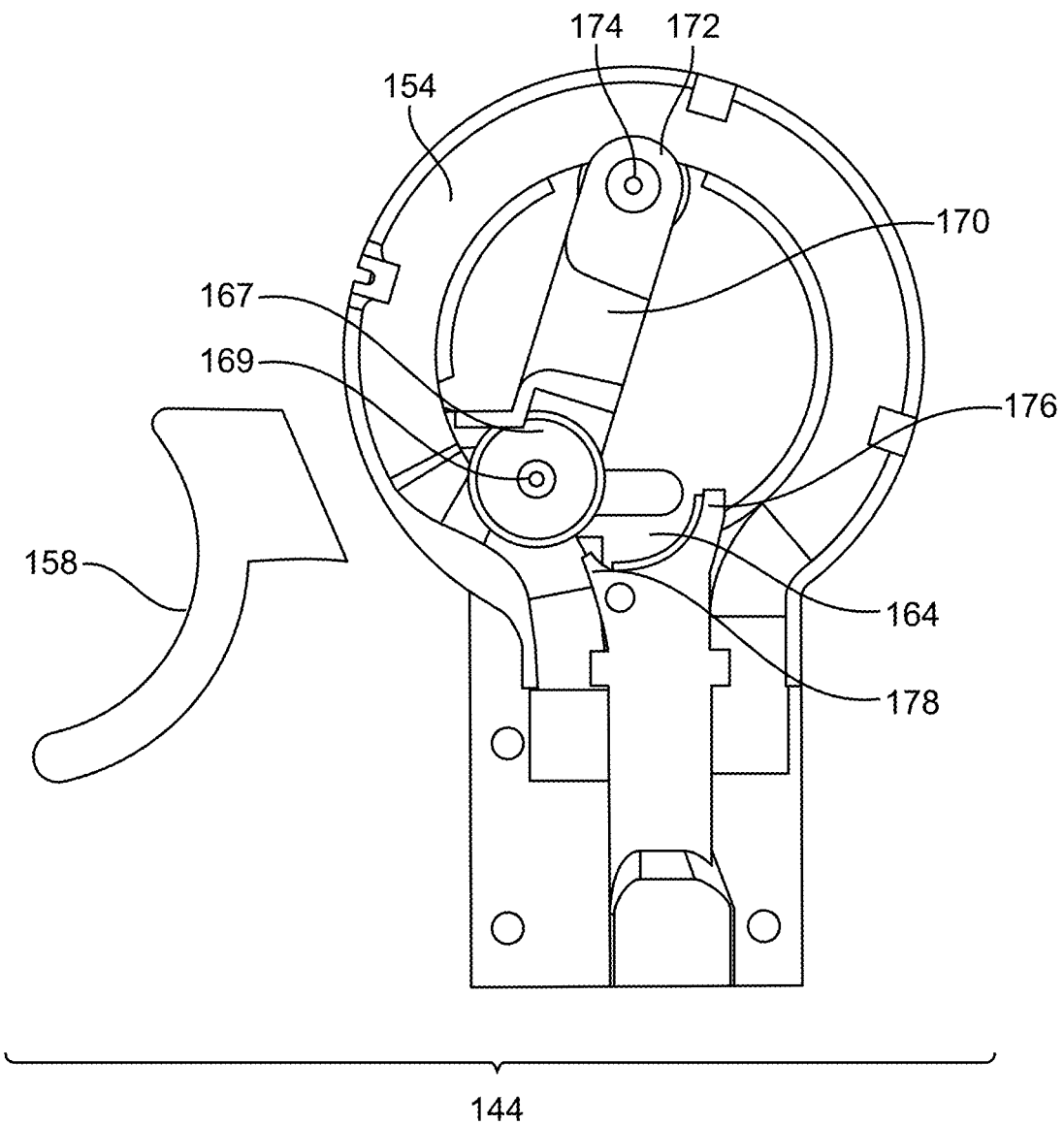
FIGS. 25 to 27 show successive positions of a trigger mechanism according to an embodiment.
Figure 26:
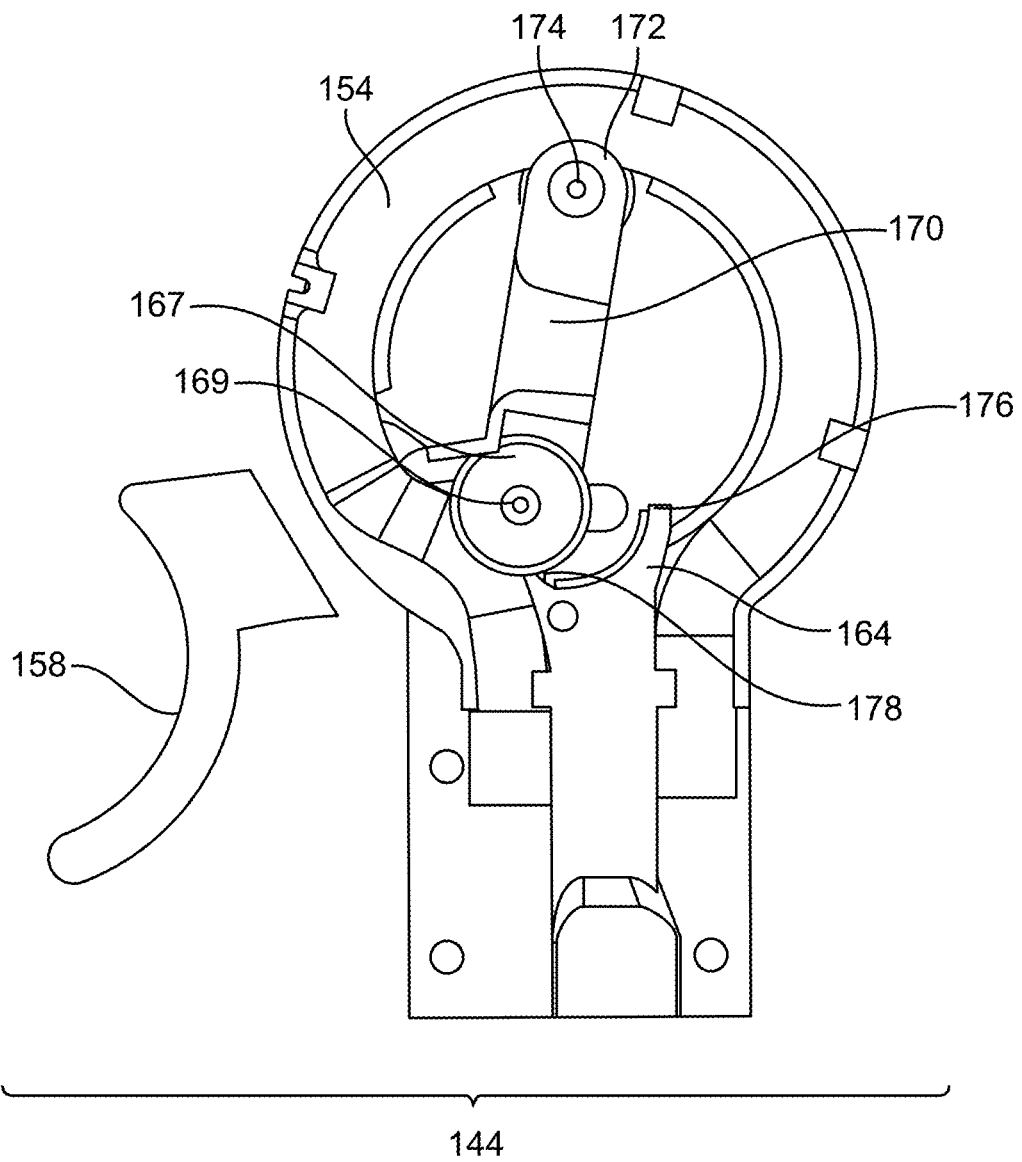
Figure 27:
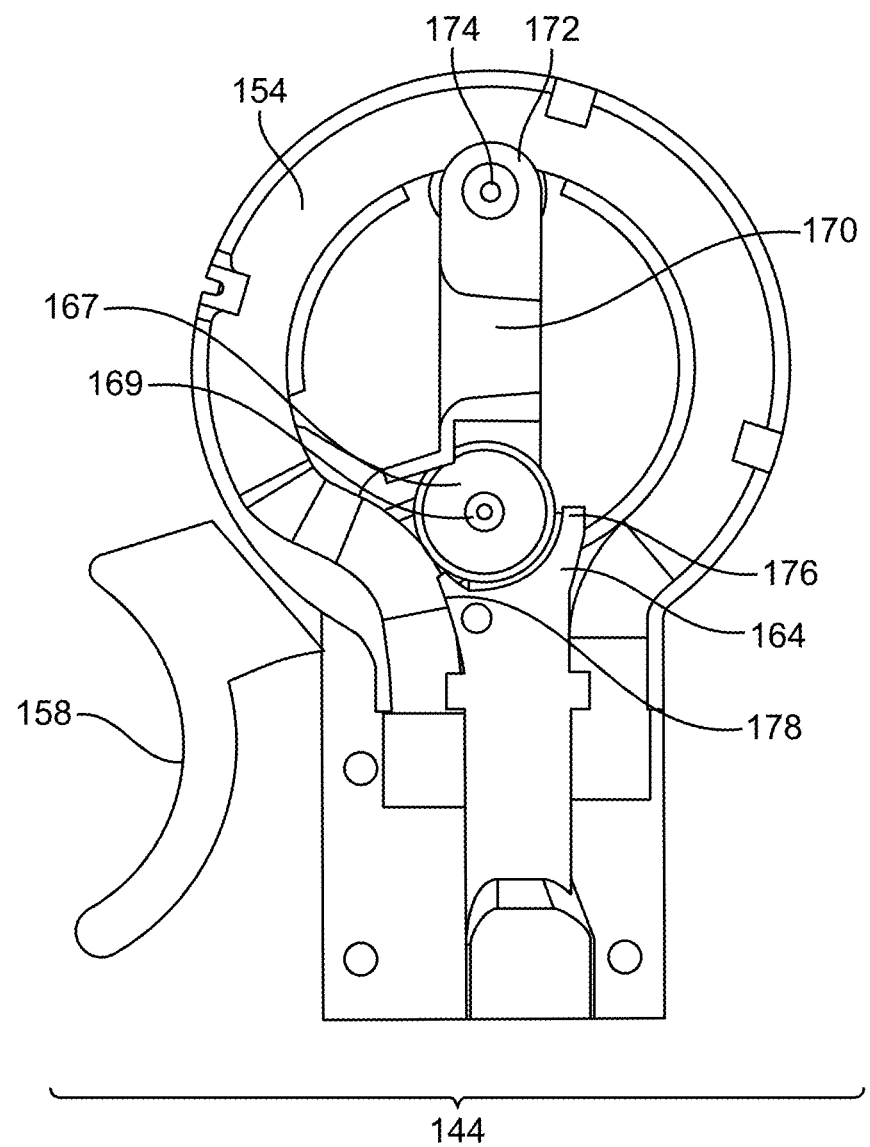

FIGS. 25-27 show successive positions of the trigger 158 for the trigger mechanism 144, from undepressed in FIG. 25 to fully depressed in FIG. 27, with corresponding movement of relevant parts. In FIG. 25, the trigger 158 is in its normal position, resulting from bias that the spring 156 or other resilient device (shown in previous Figures) applies. A roller 167 is mounted on a pin 169, at one end of a bar or lever 170. At the other end 172 of the bar or lever 170 is a mount 174 to which the bar or lever 170 is attached. With this structure, the bar or lever 170 pivots around the mount 174 when trigger 158 is depressed. Also in FIG. 25, the roller 167 is positioned away from the opening 164, which leads to a vacuum outlet (not shown). The roller 167 depresses the irrigation tube 154, closing off irrigation. Accordingly, in the trigger position shown in FIG. 25, both irrigation and vacuum are turned off. FIG. 25 further illustrates protrusions 176 and 178, the function of which is described with reference to FIGS. 26 and 27. FIG. 26 shows an intermediate position of the trigger 158, with a correspondingly intermediate position of the roller 167, closer to the opening 164. Depression of the trigger 158 causes the bar or lever 170 to rotate around the mount 174. Depression of the trigger 158 to the extent shown in FIG. 26 causes the roller 167 to come into contact with the protrusion 178, providing more resistance and signaling to the user that the trigger 158 is in an intermediate position. In this position, the roller 167 exerts less pressure on irrigation tube 154. Accordingly, in the trigger position shown in FIG. 26, vacuum still is turned off, but irrigation begins to be turned on. FIG. 27 shows a fully depressed position of the trigger 158. In this position, the user depressing the trigger 158 has caused the roller 167 to proceed over protrusion 178, to cover the opening 164, and to move farther away from the irrigation tube 154. The roller 167 moves up against the protrusion 176, signifying to the user that the trigger 158 is fully depressed. In this position, both vacuum and irrigation are turned on, so that kidney stones and/or pieces of kidney stones can be removed.

Figure 28:
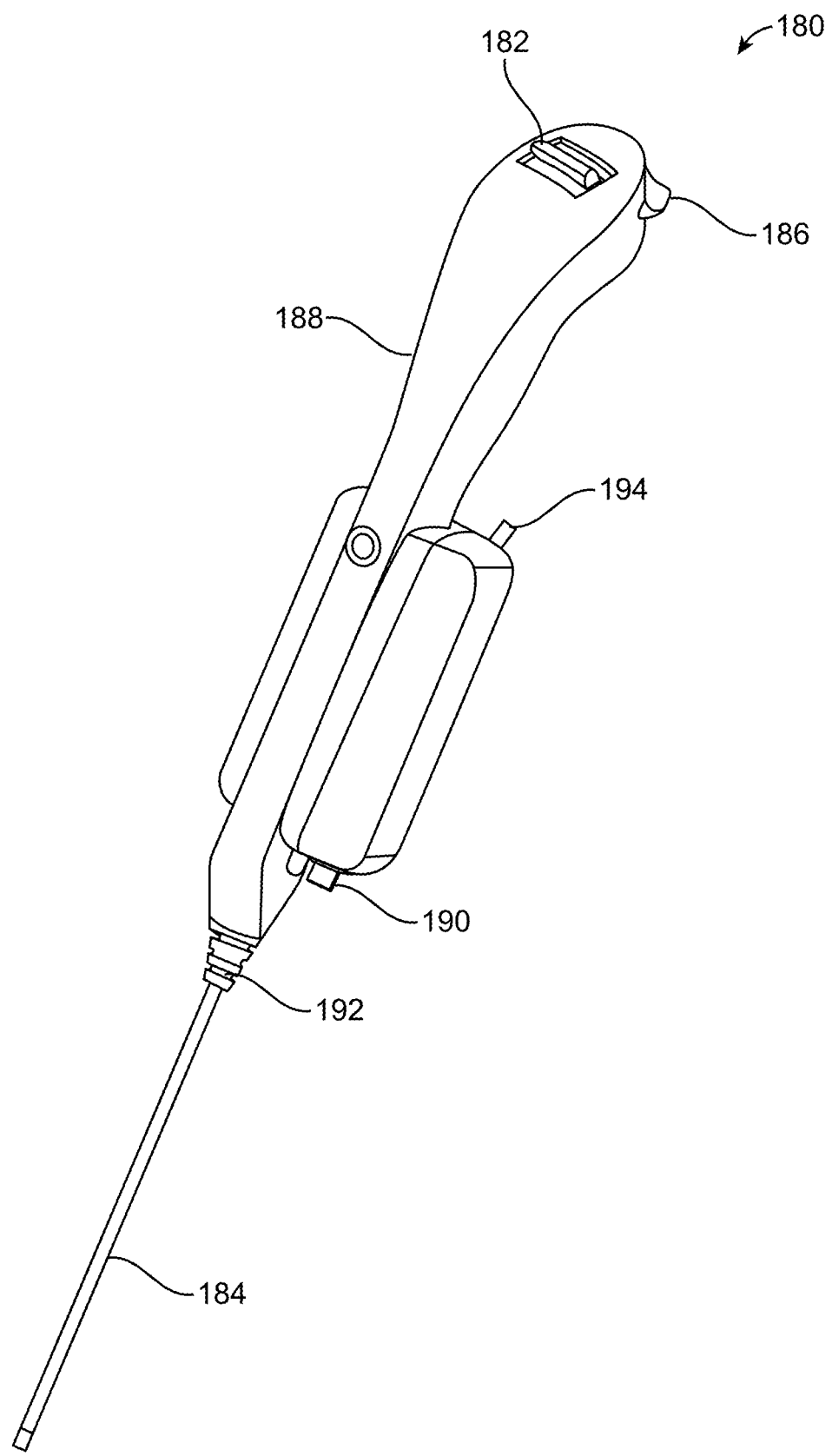
FIG. 28 shows a kidney stone treatment system according to an embodiment.
Figure 29:
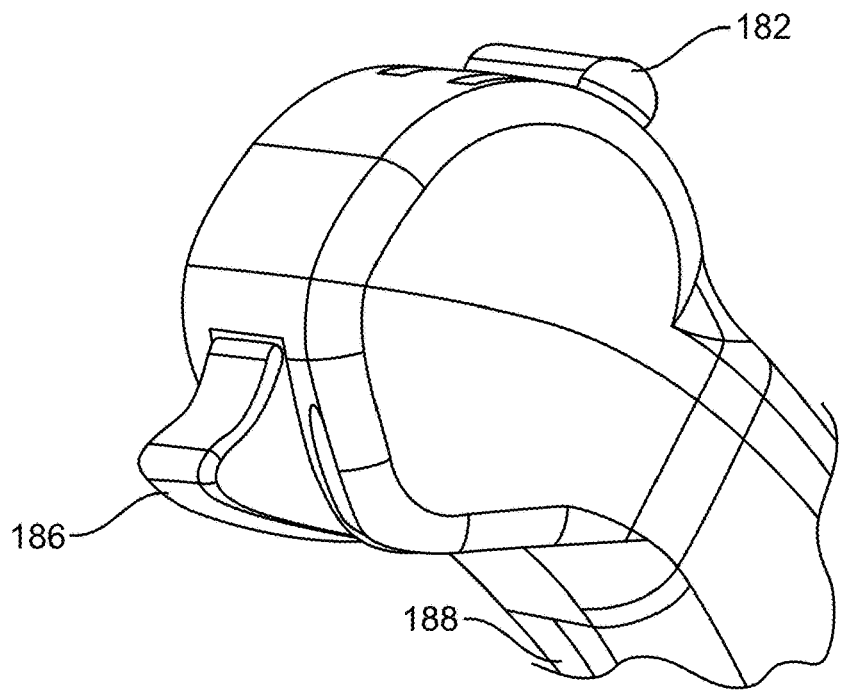
FIG. 29 shows a portion of a kidney stone removal mechanism of FIG. 28.

FIG. 28 shows a mechanism 180 for kidney stone removal according to an embodiment. In FIG. 28, a user may employ a distal tip steering control 182 to position and/or steer a catheter 184 to perform appropriate operations to break up and/or remove kidney stones. One or more pull wires (not shown) can facilitate positioning and/or steering of the catheter 184. User control of the trigger 186 controls operation of the trigger mechanism, described further herein, to control vacuum and irrigation through the catheter 184. A handle portion 188 is sized for a user to hold the mechanism 180, with the user's thumb operating the distal tip steering control 182 and one of the user's fingers operating the trigger 186. Alternatively, a user's thumb may operate the trigger 186, and a user's finger may operate the distal tip steering control 182. Also in FIG. 28, a port 190 connects to a vacuum source (not shown). The catheter 184 is attached to a catheter strain relief 192. In an embodiment, a port 194 provides access to a working channel within the catheter 184 to facilitate introduction of therapeutic tools, such as a laser, to the distal end of the catheter 184. FIG. 29 shows an enlarged view of the distal tip steering control 182 and the trigger 186, and an upper portion of the handle portion 188.

Figure 30:
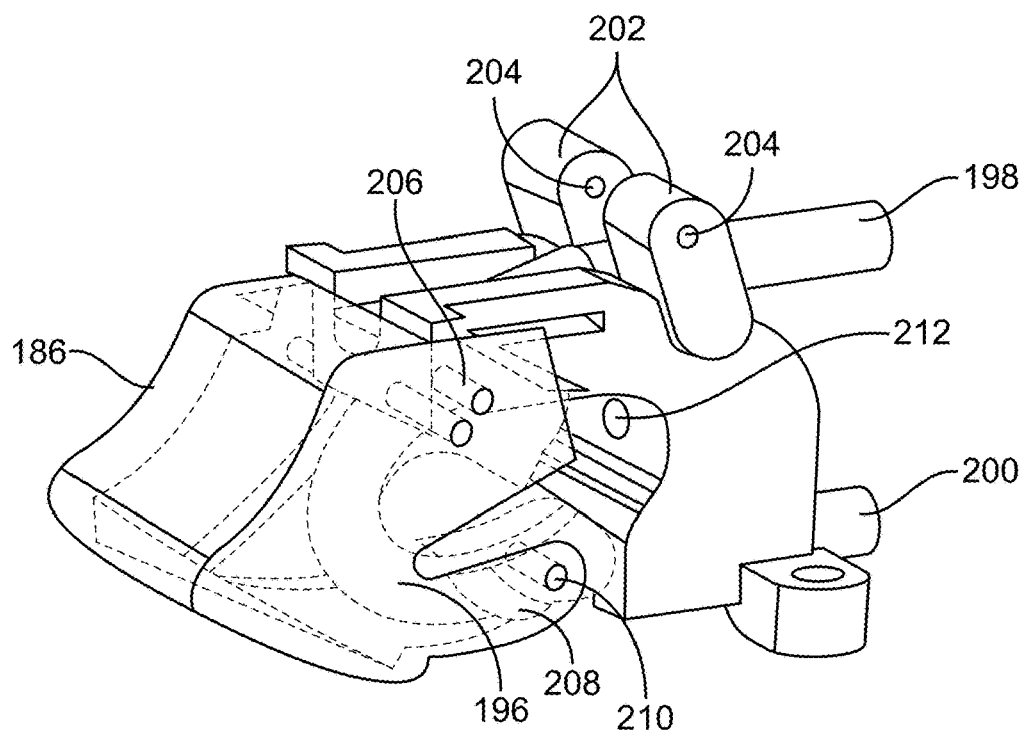
FIG. 30 shows a view of a portion of a kidney stone removal mechanism according to an embodiment.

FIG. 30 shows an example of a trigger mechanism that may be used in the embodiment of FIGS. 28 and 29. An irrigation tube 196 has inlet 198, connected to an irrigation source, and an outlet 200, connected to a distal tip (not shown) to irrigate a desired region. Posts 202 are located and sized to hold the distal tip steering control 182, which may be attached to the posts 202 via one or more pins (also not shown) passing through holes 204 in the posts 202. As part of the distal tip steering control 182, pull wires (not shown) may be provided to guide movement and position of the catheter's distal tip to perform suitable actions to maneuver the tip into proper position for a kidney stone removal procedure. Depression of the trigger 186 causes rotation of the trigger 186 around pivot pin 206, and causes a roller 208, attached via a pin 210, to move from the position shown to a location so as to cover a port 212, which is connected to ambient air via to an activation tube (not shown). That is, covering the port 212 functions in the same way as the activation pinch mechanism 96 of FIGS. 35 and 36 in that when the port 212 is covered there is no longer flow from ambient air to the vacuum source. When the port 212 is uncovered, the vacuum is off at the target area. When the port 212 is covered, the vacuum is on at the target area.

Figure 31:
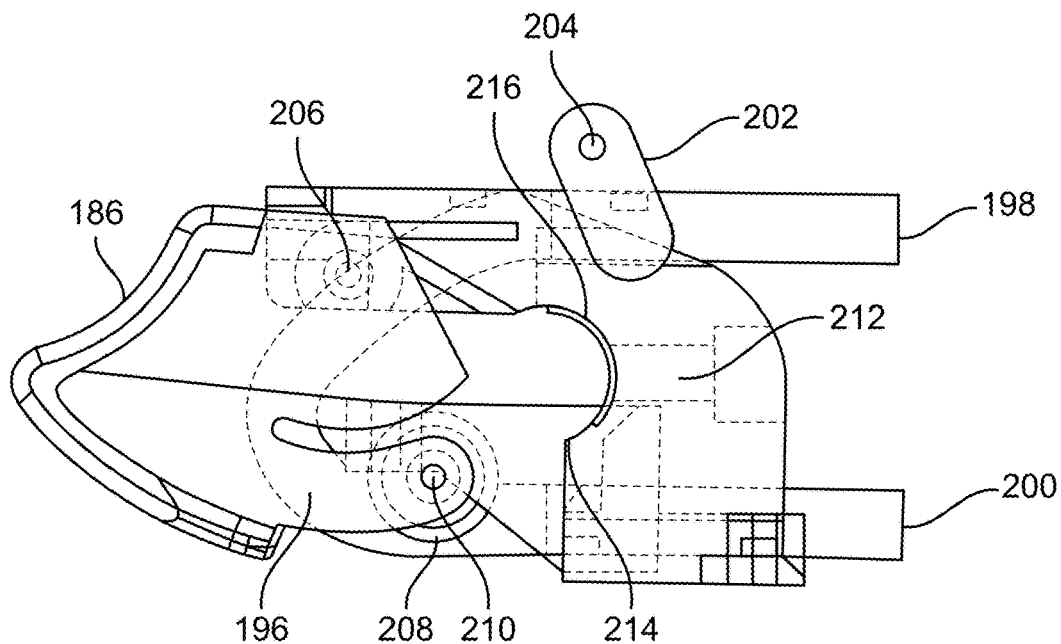
FIGS. 31 to 34 show successive positions of a trigger in the structure of FIG. 30 according to an embodiment.
Figure 32:
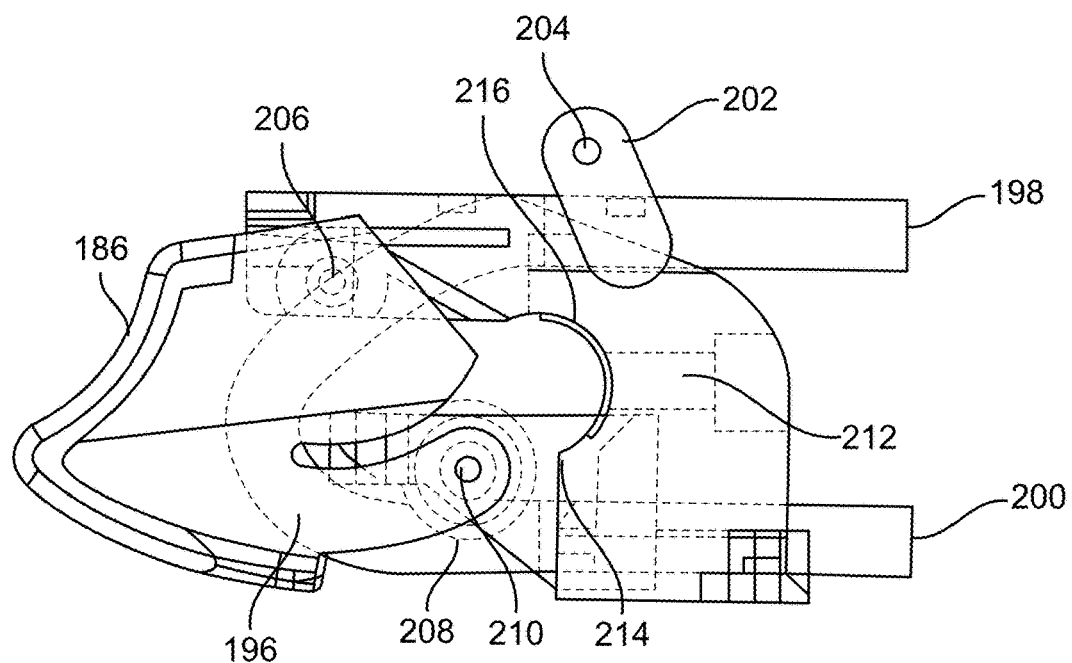
Figure 33:
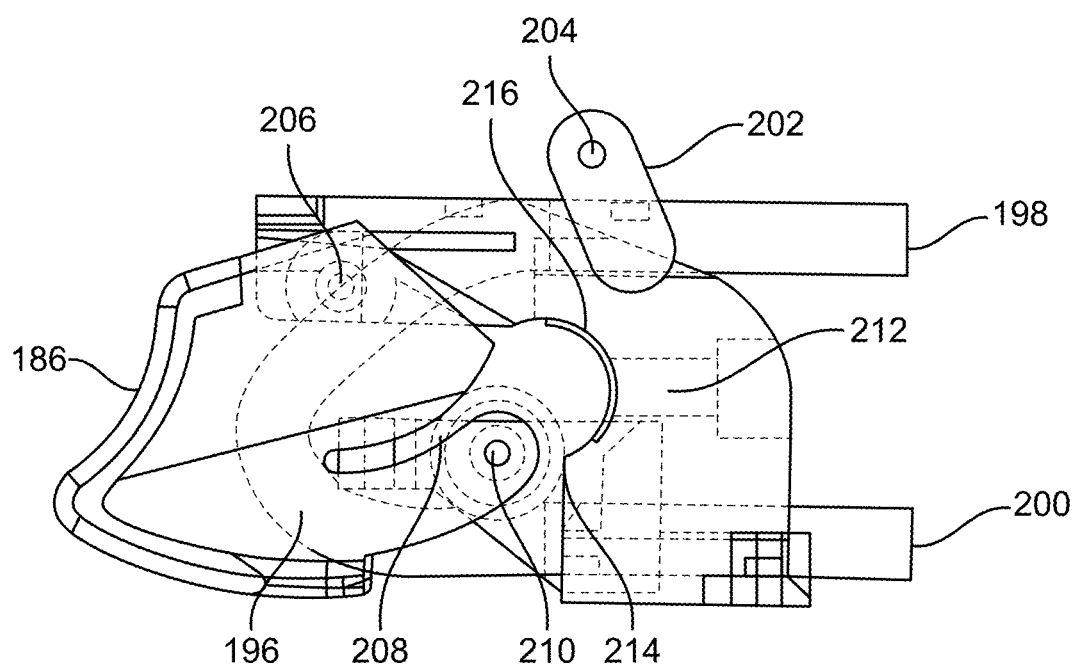
Figure 34:
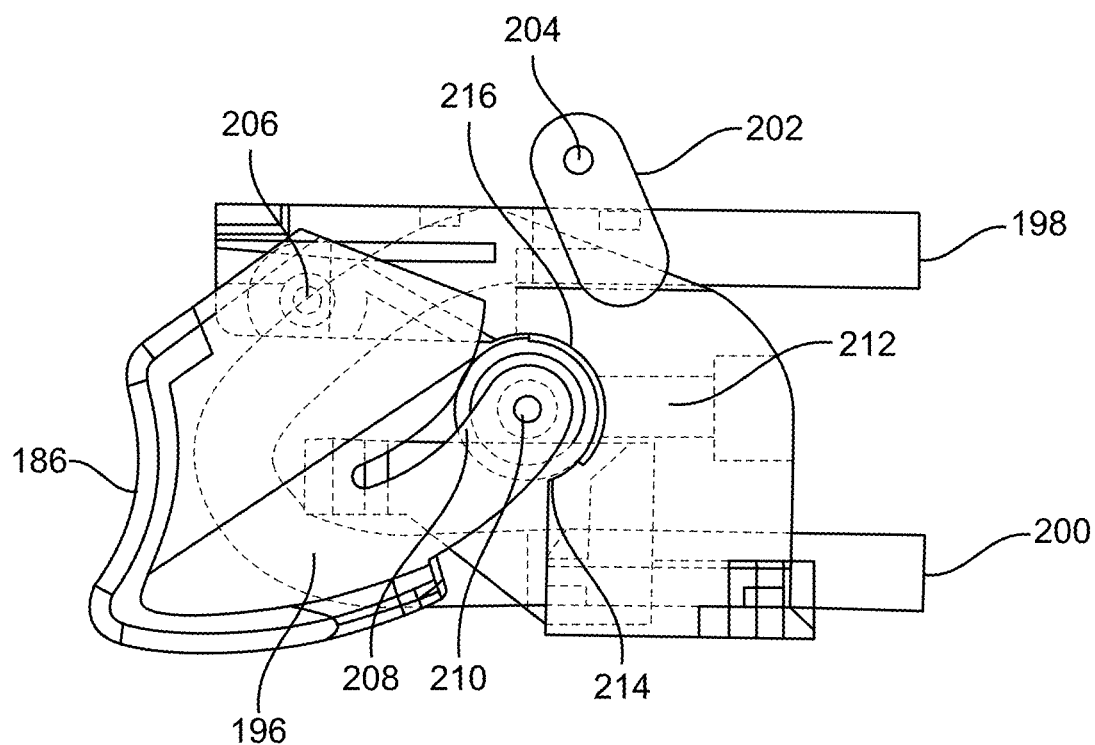

FIGS. 31-34 show progressive depressions of the trigger 186. In these figures, for ease of description, posts 202 remain in the same position, that is, the distal tip steering control 182 is not being operated. FIG. 31 shows the trigger 186 in an undepressed position. In this position, the roller 208 closes off, or at least constricts, irrigation the tube 196, while the port 212 is open. The roller 208 is set apart from a contact edge 214. This position corresponds to the vacuum and the irrigation both being turned off. In FIG. 32, initial depression of the trigger 186 causes the trigger 186 to rotate slightly to the right around the pivot pin 206, causing the roller 208 to move slightly upward and to the right. In this position, the irrigation tube 196 is opened further, allowing irrigation of the area to be treated. This positioning of the trigger 186 corresponds to an irrigation only state, with vacuum still turned off by virtue of the port 212 remaining open. In FIG. 33, further depression of the trigger 186 causes the trigger 186 to rotate slightly more to the right around the pivot pin 206, causing the roller 208 to move slightly more upward and to the right. With the roller 208 in this position, the port 212 remains open, so vacuum still is turned off. The irrigation tube 196 is squeezed less, allowing for more irrigation of the affected area. In this position, the roller 208 contacts an edge 214, which acts as a detent, according to an embodiment. When the roller 208 contacts the edge 214, the user is alerted, by virtue of encountering resistance to depression of the trigger 186. In FIG. 34, when the user overcomes the resistance at the edge 214 and depresses the trigger 186 farther, the trigger 186 rotates farther upward and to the right until the roller 208 covers the port 212. At this point, the roller 208 is seated in indentation 216, and cannot move farther. In this fashion, the user is aware that the trigger depression is at maximum. When the trigger 186 is in this position, irrigation remains on, and vacuum turns on, by virtue of the port 212 being closed (for example, performing as described in FIGS. 35 and 36).

Figure 37:
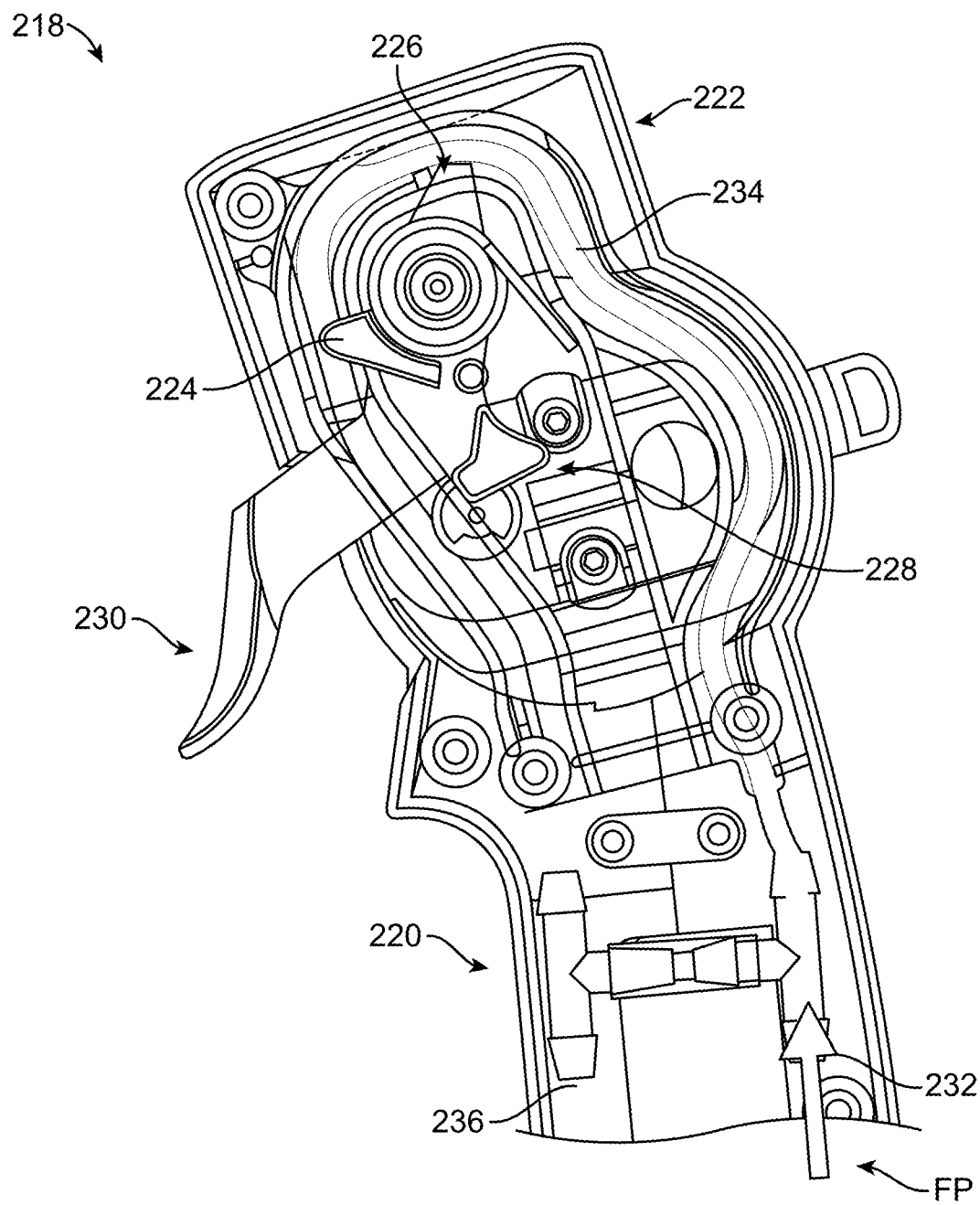
FIGS. 37 and 38 show successive positions of a trigger in a trigger activation mechanism according to an embodiment.
Figure 38:
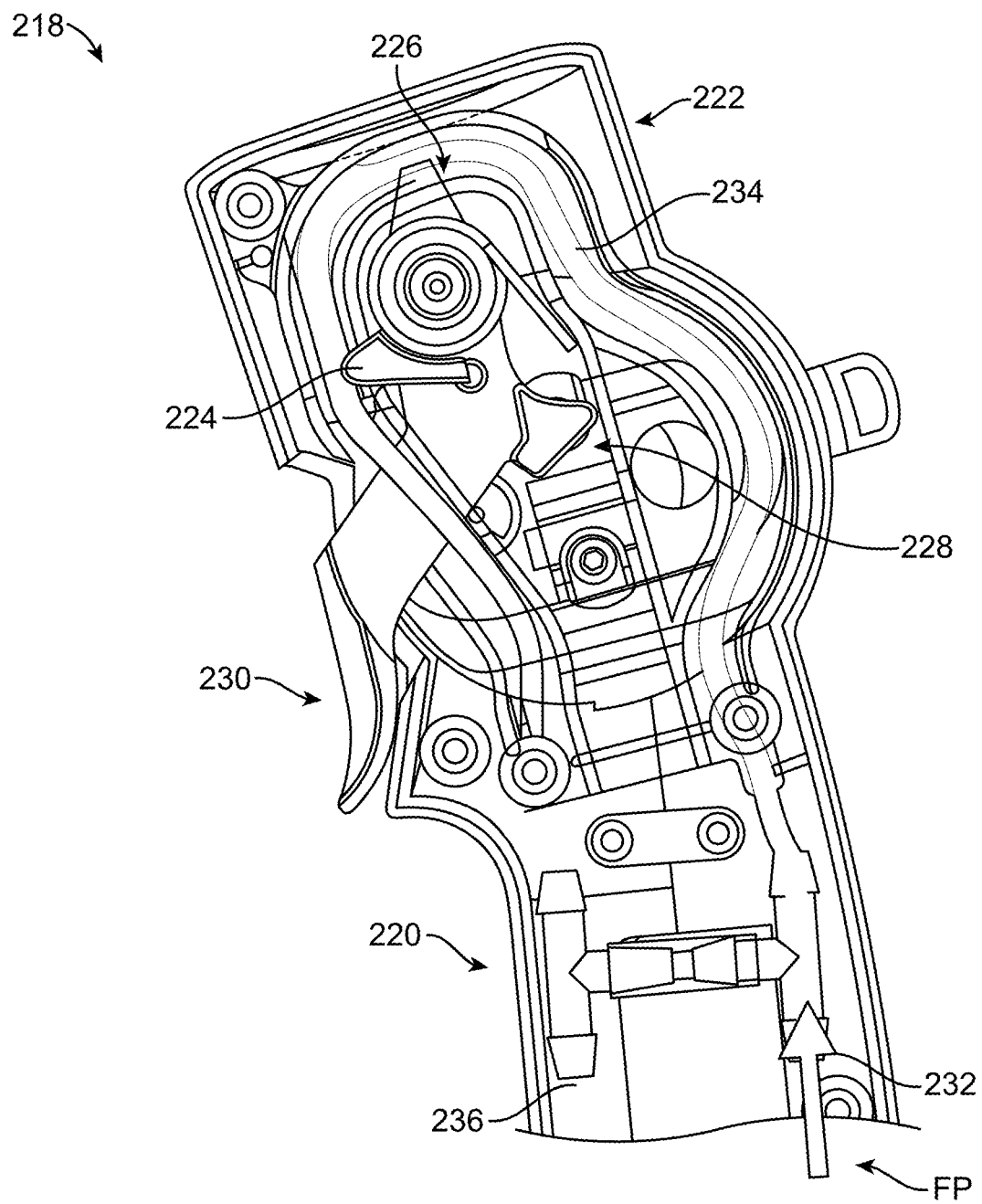

FIGS. 37 and 38 show an embodiment of a mechanism 218 that includes an irrigation bypass structure 220, which functions to always provide a minimum irrigation flow through the mechanism. The irrigation bypass structure 220 can be implemented with any of the embodiment disclosed above and is not limited to mechanism 218. FIGS. 37 and 38 show a mechanism head 222 having protrusions 224, 226, and 228, which function as disclosed in other embodiments herein to control irrigation and vacuum/suction using a single trigger 230. In some cases, the user may wish to maintain a minimum irrigation flow through the mechanism 218 without having to activate the trigger 230. In some embodiments of the mechanism disclosed herein, the protrusion 224 may be implemented such that the protrusion 224 does not completely close off the irrigation tube against which the protrusion 224 is positioned. Such an implementation may be suitable for some cases, but in other cases may not provide a sufficiently well-defined minimum flow rate. That is, the extent of the incomplete closure of the irrigation tube may vary more than is desired. FIGS. 37 and 38 provide an embodiment in which a more well-defined minimum irrigation flow can be provided through irrigation bypass structure 220 than via incomplete closure of the irrigation tube.

FIG. 37 shows a flow path FP in which most of the flow of irrigation fluid flows from an inlet 232 through an irrigation tube 234 until the flow is stopped by the protrusion 224 having closed off the irrigation tube 234 by pinching it closed. A lower amount of the flow of the irrigation fluid passes from the inlet 232 through the irrigation bypass structure 220 and to an outlet 236, which is connected to a distal end of the stone removal device. Thus, in this embodiment at least some irrigation is always flowing to the distal end of the stone removal device. FIG. 38 shows a configuration in which the trigger 230 is depressed, thereby moving the protrusion 224 away from the irrigation tube 234 and opening the irrigation tube 234. With the irrigation tube 234 open, irrigation fluid can flow along flow path FP from the inlet 232 through the mechanism head 222 and to the outlet 236. Some minor amount of irrigation fluid may still flow through the bypass structure 220, but most of the irrigation fluid flows through the mechanism head 22.

Figure 39:
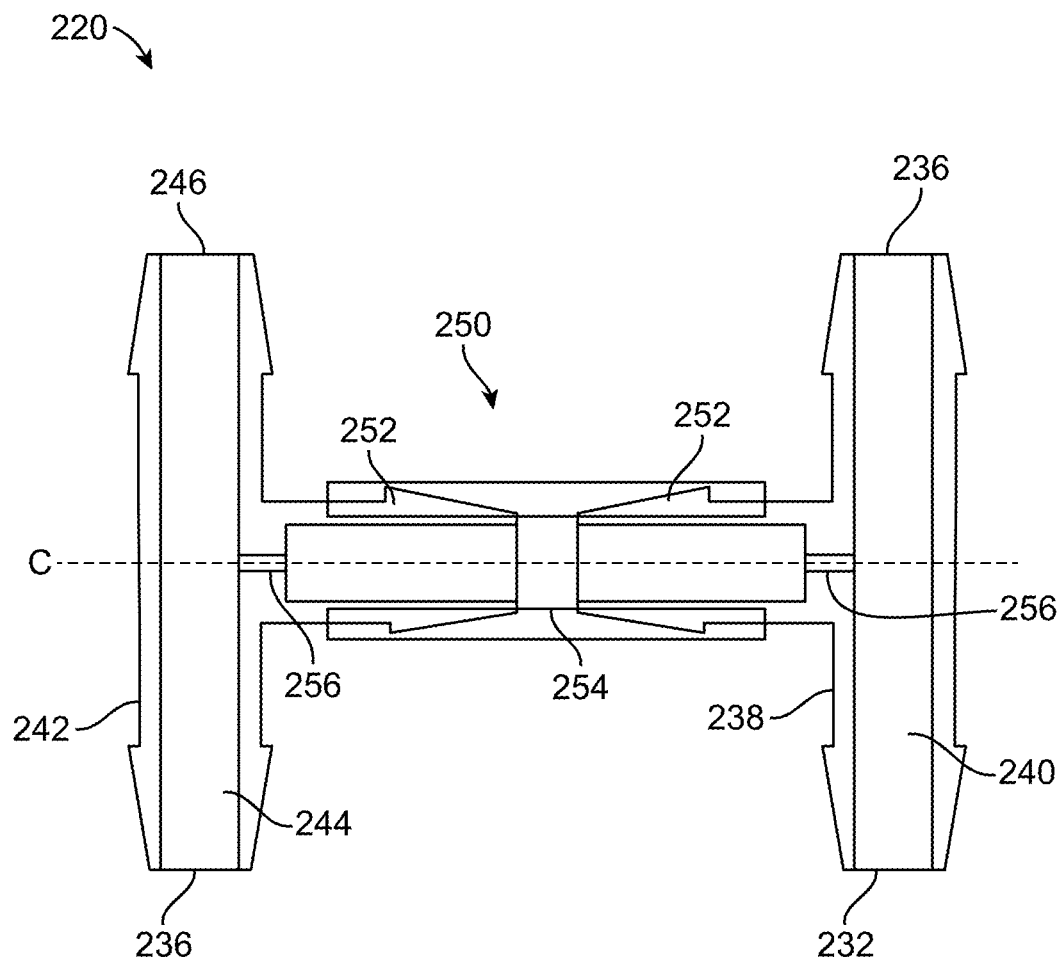
FIG. 39 shows a flow bypass structure of a mechanism according to an embodiment.

FIG. 39 shows the irrigation bypass structure 220 having an inlet tube 238 that defines an inlet lumen 240, which connects the inlet 232 with the supply outlet 236 and having an outlet tube 242 that defines an outlet lumen 244, which connects a return inlet 246 with the outlet 236. An irrigation tube (not pictured) connects the supply outlet 236 with return the inlet 246 and carries irrigation fluid through the mechanism head and trigger activation mechanism of various embodiments disclosed herein. The inlet tube 238 is connected with the outlet tube 242 by a bypass 250, which includes a pair of bypass tubes 252 connected by a bypass connector 254. FIG. 39 shows the bypass tubes 252 as hose barbs and the bypass connector 254 as tubing, but other equivalent configurations of similar structure can be used. The bypass 250 includes flow restrictions 256, which are narrow lumens (narrower than the diameter of the inlet lumen 240) that restrict the amount of irrigation fluid that can flow through the bypass 250. FIG. 39 shows two flow restrictions 256 because it may be desirable for manufacturing efficiency to produce two of the same parts and connect them via the connector 254 to form irrigation bypass structure 220, but a single flow restriction 256 can be sufficient to provide the function of the irrigation bypass structure 220 as disclosed herein. In some embodiments, the inner diameter of the flow restriction 256 can be in the range of about 5% to about 30% of the inner diameter of the inlet lumen 240 and in some embodiments about 20% of the inner diameter of inlet 240. For example, the flow restriction 256 can have an inner diameter of about 0.5 mm when the inlet lumen 240 has an inner diameter of about 2.5 mm. Other specific inner diameters within the percentage ranges disclosed are within the scope of the bypass structure. As flow rate varies to the fourth power of diameter, the ratio of the inner diameters of the flow restriction 256 and the inlet lumen 240 directly influence the ration of the flow rate through the trigger mechanism and through the bypass structure. Other factors, such as surface tension and pressure drop, may influence the extent to which the flow rate is dominated by this power law relationship.

Figure 40:
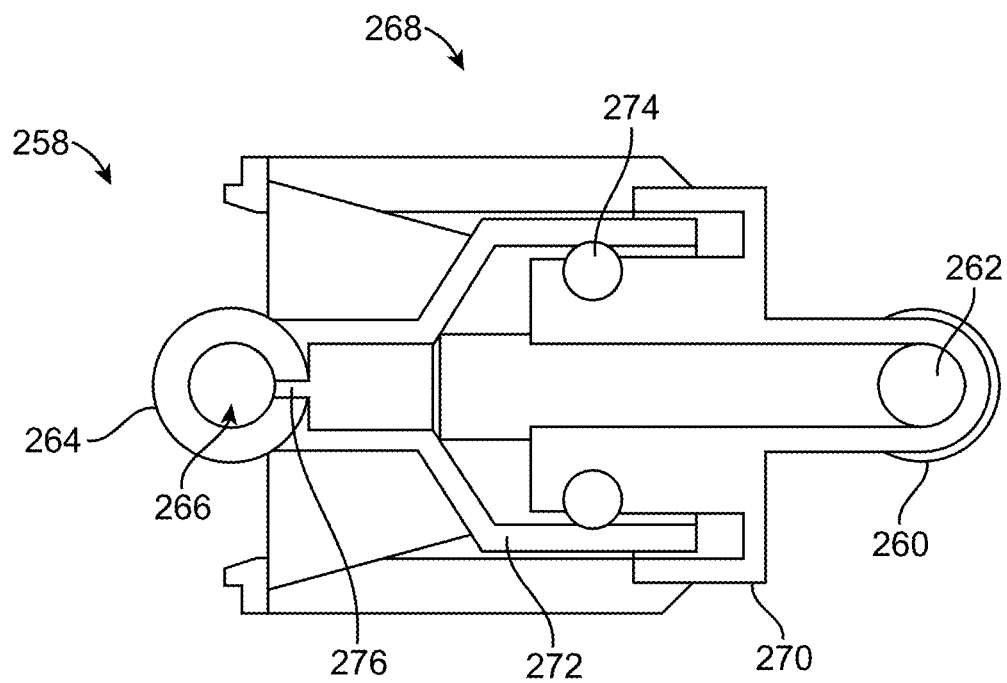
FIG. 40 shows a cross section of a flow bypass structure of a mechanism according to an embodiment.

FIG. 40 shows an irrigation bypass structure 258 of an alternate embodiment viewed in cross section defined by a plane along line C in the embodiment of similar irrigation bypass structure 220. This bypass structure can be implemented with any of the embodiments disclosed above. The irrigation bypass structure 258 includes an inlet tube 260, which defines an inlet lumen 262, and an outlet tube 264, which defines an outlet lumen 266. These lumens are connected by an irrigation tube (not pictured) that carries irrigation fluid through mechanism heads and trigger activation systems disclosed herein. FIG. 40 shows that the inlet lumen 262 and the outlet lumen 266 are also connected by a bypass 268, which is formed by a first bypass fitting 270 and a second bypass fitting 272. The first bypass fitting 270 and the second bypass fitting 272 connect via complementary features and form a fluid tight seal via O-ring 274. When connected, the first bypass fitting 270 and the second bypass fitting 272 form a conduit for fluid bypass, and this conduit include a flow restriction 276 that has a lumen narrower than the inlet lumen 262. Thus, the irrigation bypass structure 258 functions to provide a well-defined minimum irrigation flow rate when the irrigation tube in the mechanism head is closed by the trigger mechanism.

Figure 41:
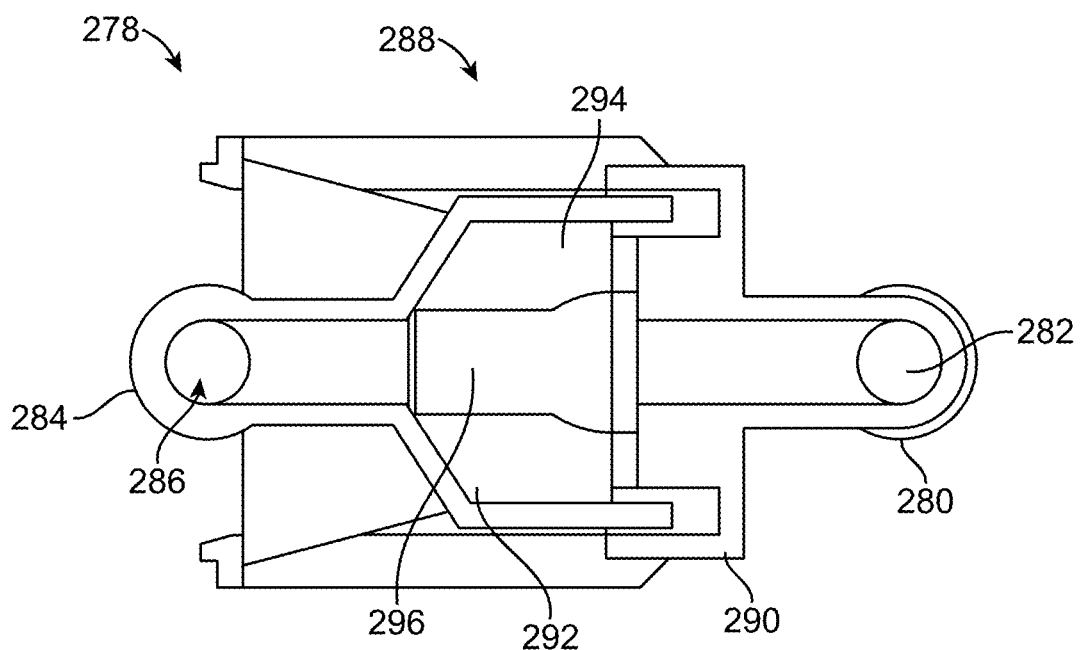
FIG. 41 shows a cross section of a flow bypass structure of a mechanism according to an embodiment.

FIG. 41 shows an irrigation bypass structure 278 of another alternate embodiment viewed in cross section defined by a plane along line C in the embodiment of similar irrigation bypass structures 220 and 258. This bypass structure can be implemented with any of the embodiments disclosed above. The irrigation bypass structure 278 includes an inlet tube 280, which defines an inlet lumen 282, and an outlet tube 284, which defines the outlet lumen 286. These lumens are connected by an irrigation tube (not pictured) that carries irrigation fluid through mechanism heads and trigger activation systems disclosed herein. FIG. 41 shows that the inlet lumen 282 and the outlet lumen 286 are also connected by a bypass 288, which is formed by a first bypass fitting 290 and a second bypass fitting 292. The first bypass fitting 290 and the second bypass fitting 292 connect via complementary features and form a fluid tight seal via compressible member 294, which is formed of a resiliently flexible material and includes an interior flow restriction 296. The compressible member 294 is similar to an O-ring or grommet in shape or function in that it provides a fluid tight seal, but it also provides a lumen in the form of the flow restriction 296, which takes a predefined diameter when the first bypass fitting 290 and the second bypass fitting 292 are connected. This predefined diameter of flow restriction 6664 is narrower than the diameter of the inlet lumen 282. Thus, the irrigation bypass structure 278 functions to provide a well-defined minimum irrigation flow rate when the irrigation tube in the mechanism head is closed by the trigger mechanism.

Figure 42:
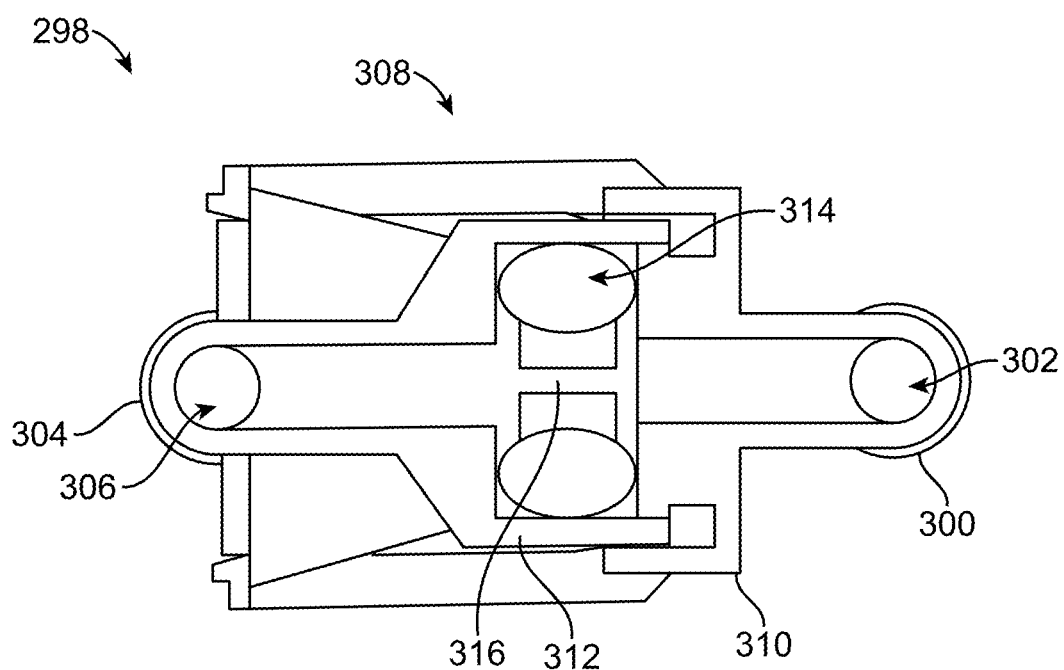
FIG. 42 shows a cross section of a flow bypass structure of a mechanism according to an embodiment.

FIG. 42 shows an irrigation bypass structure 298 of another alternate embodiment viewed in cross section defined by a plane along line C in the embodiment of similar irrigation bypass structures 220, 258, and 278. This bypass structure can be implemented with any of the embodiments disclosed above. The irrigation bypass structure 298 includes an inlet tube 300, which defines inlet lumen 302, and an outlet tube 304, which defines outlet lumen 306. These lumens are connected by an irrigation tube (not pictured) that carries irrigation fluid through mechanism heads and trigger activation systems disclosed herein. FIG. 42 shows that the inlet lumen 302 and the outlet lumen 306 are also connected by a bypass 308, which is formed by a first bypass fitting 310 and a second bypass fitting 312. The first bypass fitting 310 and the second bypass fitting 312 connect via complementary features and form a fluid tight seal via O-ring 314, which is formed of a resiliently flexible material. The second bypass fitting 312 also includes an interior flow restriction 316, which has a diameter narrower than the diameter of the inlet lumen 300. Thus, irrigation bypass structure 298 functions to provide a well-defined minimum irrigation flow rate when the irrigation tube in the mechanism head is closed by the trigger mechanism.

The various flow control mechanisms and bypass structures described herein can alternatively reside in a separate unit from the handle of the device. In this scenario, a flexible irrigation tube and a flexible vacuum line connect the separate unit with the handle. The separate unit can be controlled by the user via foot pedals, a touchscreen, or other similar activation mechanisms. The mechanisms in the separate unit can be controlled mechanically, electro-mechanically, electromagnetically, or by other similar control methods. In one example, the separate unit is a reusable unit, similar to or included with the control unit 18. In this example, control unit 18 provides irrigation fluid and negative pressure to the system in addition to imaging control.

Figure 43:
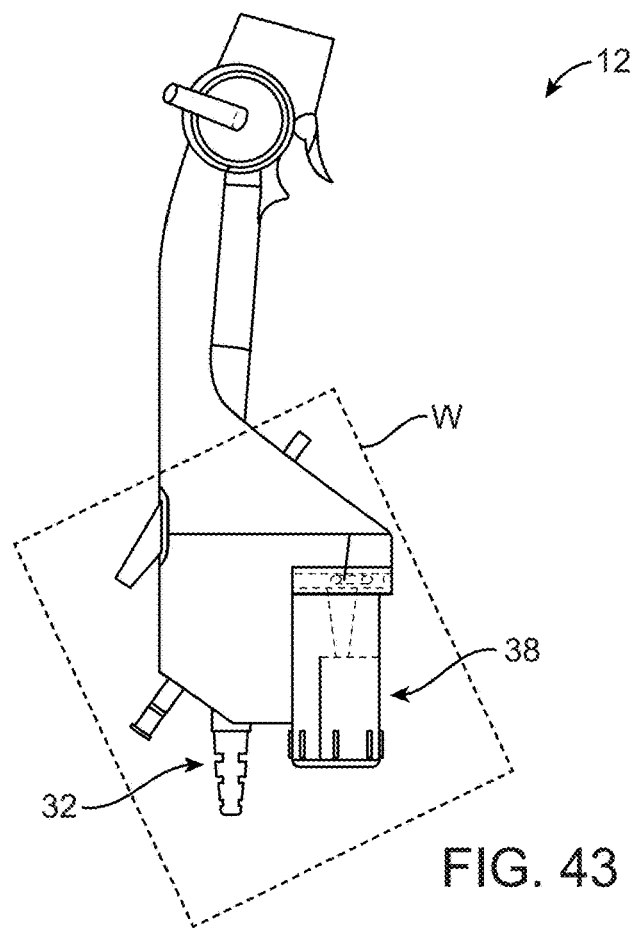
FIG. 43 is a view of a kidney stone removal mechanism according to an embodiment.
Figure 44:
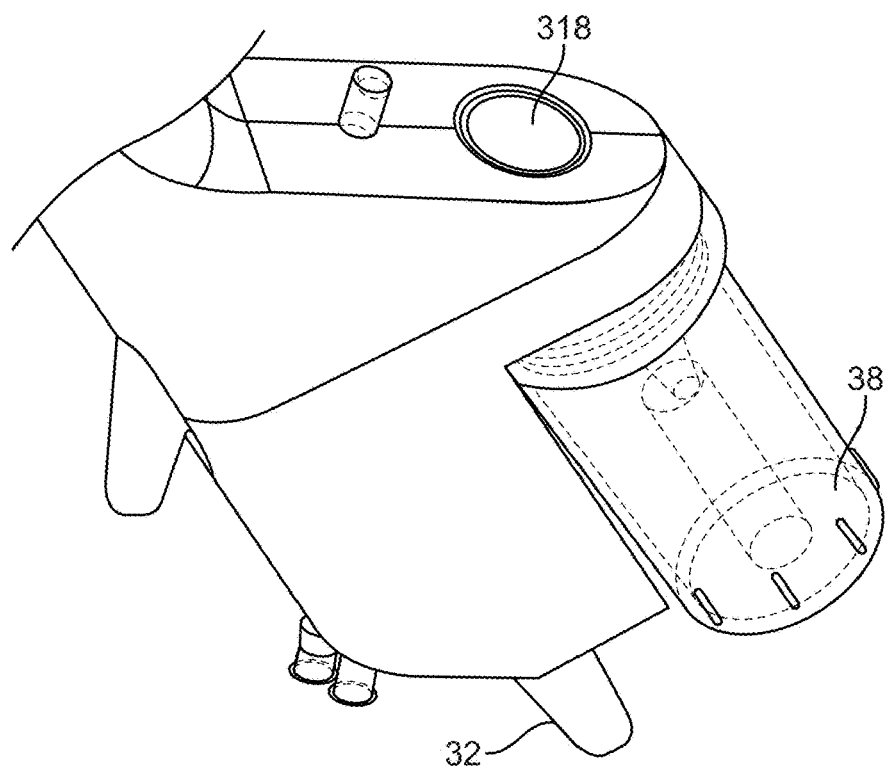
FIG. 44 is a rotated and enlarged view of a portion a kidney stone removal mechanism according to an embodiment.

FIG. 43 shows the mechanism 12 for effecting kidney stone removal according to an embodiment. The lower portion of the mechanism includes the stone catcher receptacle 38 in fluid communication with the vacuum inlet 32. FIG. 44 is a rotated and enlarged view of the mechanism 12 inside box W of FIG. 43 and shows the location on mechanism 12 of a flow indicator 318. The flow indicator 318 provides a visual (and optionally audible) indication of whether air and/or fluid is flowing through mechanism 12 and out to the vacuum inlet 32. The absence of fluid flow through mechanism 12 can indicate that there is a clog somewhere in the fluid path within the stone removal device. The clog could be in the catheter section or in the mechanism 12, and it can be important to address such a clog to prevent overpressure in the kidney caused by continuing to irrigate the kidney in the presence of a clog.

Figure 45:
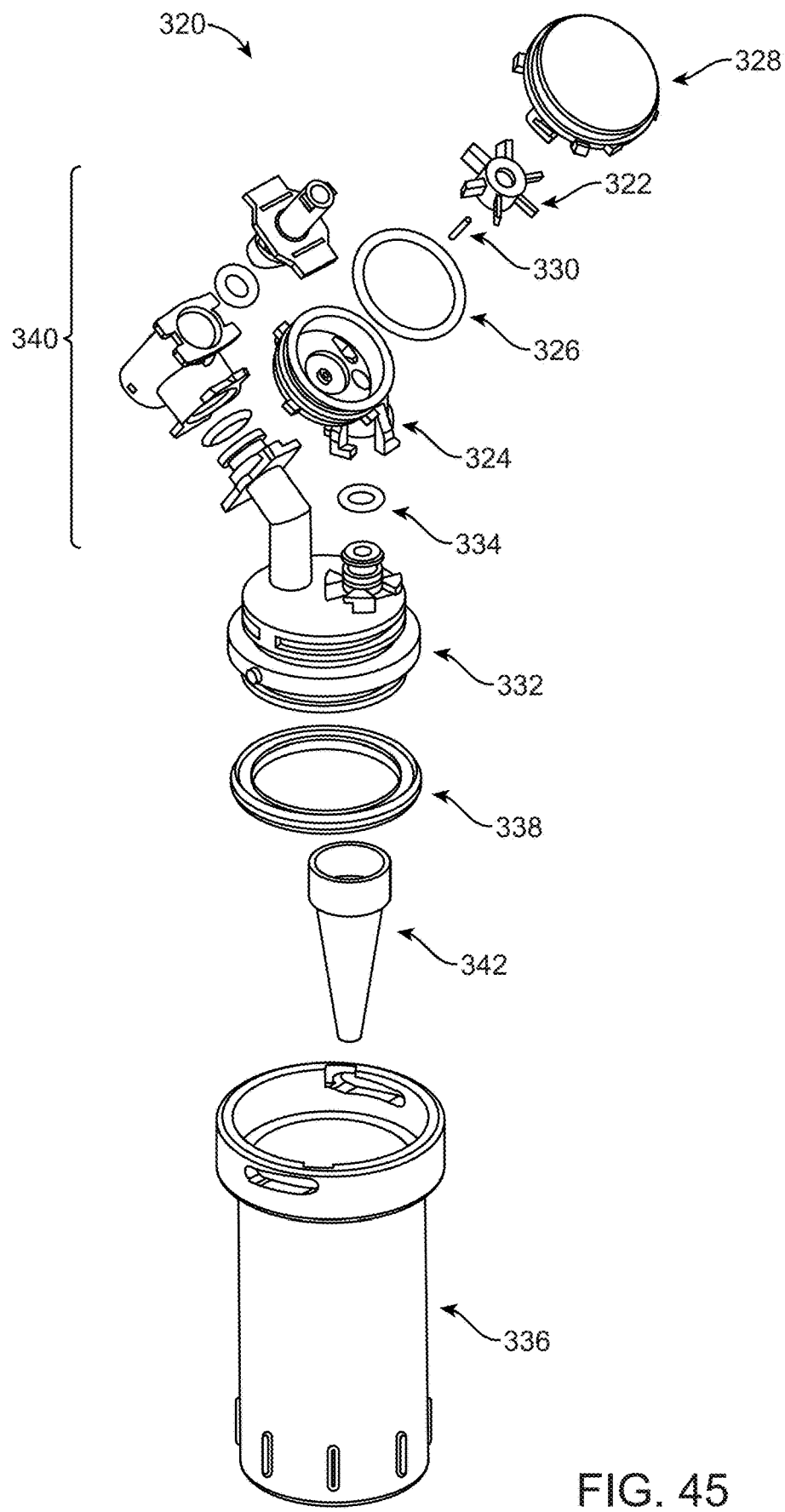
FIG. 45 is an exploded view of a stone catcher assembly according to an embodiment.

FIG. 45 is an exploded view of a stone catcher assembly 320 that is configured to be part of mechanism 12 and can be implemented with any of the above-described embodiments. A flow indicator 322 is contained within a flow indicator housing 324 with an O-ring 326 that seals the flow indicator housing 324 with a flow indicator cover 328, which is transparent or translucent such that a user can observe the movement of the flow indicator 322. An axle 330 allows the flow indicator 322 to rotate in the presence of flow. Alternate configurations of flow indicators are within the scope of this disclosure, such as any configuration that moves visibly in response to flow within a housing. The flow indicator housing 324 is connected to a stone catcher receptacle cap assembly 332 by a fluid tight seal, such as with an O-ring 334. The stone catcher receptacle cap assembly 332 is connected with a stone catcher receptacle 336 via a stone catcher receptacle seal 338. The stone catcher receptacle cap assembly 332 is also connected with an inflow assembly 340. In use, the direction of flow of fluid (including kidney stone debris) in the stone catcher assembly 320 is through inflow assembly 340, which is connected to the catheter section of the stone removal device, and to the stone catcher receptacle 336. Fluid and air are drawn up through stone catcher receptacle filter 342, which keeps debris within the stone catcher receptacle 336, but allows fluid and air to pass through and eventually into the flow indicator housing 324 to interact with the flow indicator 322. Thus, the flow indicator 322 is unlikely to become jammed or stuck with kidney stone debris. In any embodiment of a flow indicator, the flow indicator should be protected from having its movement stopped by debris interacting with the flow indicator itself.

Figure 46:
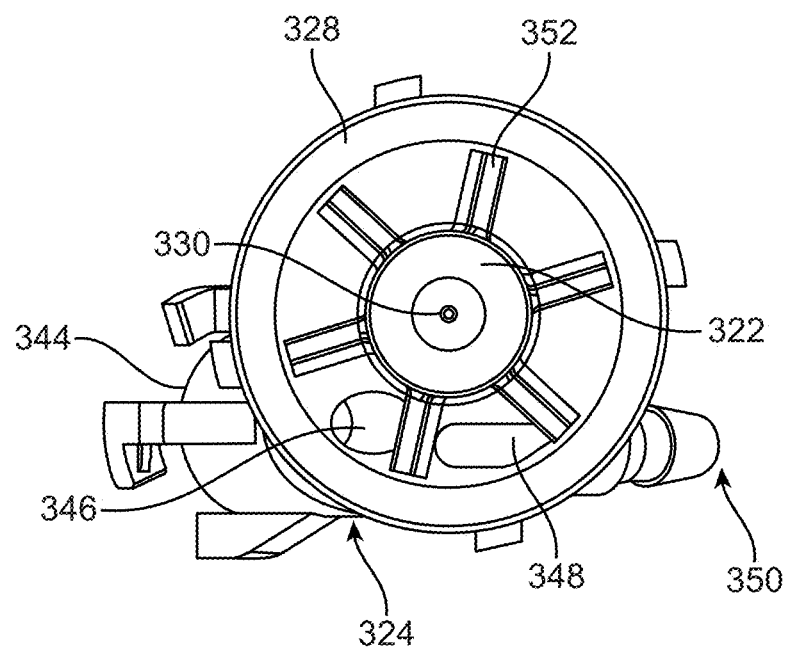
FIGS. 46 and 47 are two views of a flow indicator mechanism according to an embodiment.
Figure 47:
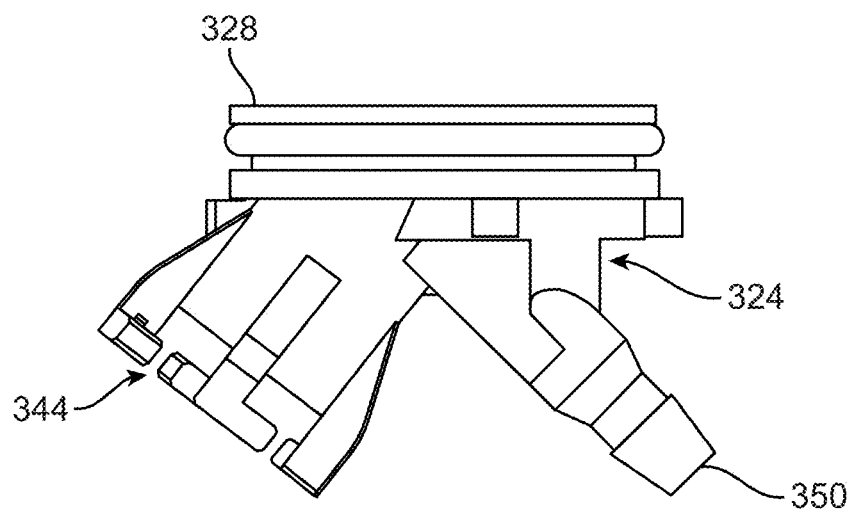

FIGS. 46 and 47 are two views of the flow indicator mechanism that includes the flow indicator 322 positioned in the flow indicator housing 324. Fluid from the stone catcher receptacle 336 enters the flow indicator housing 324 via a flow inlet 344, which is connected with an indicator inlet 346 to introduce fluid into the flow indicator housing 324 to interact with the flow indicator 322. Fluid exits the flow indicator housing 324 via an indicator outlet 348 connected with a flow outlet 350. The flow indicator 322 includes at least two flow indicator vanes 352 that interact with fluid as it moves from the indicator inlet 346 to the indicator outlet 348. The movement of fluid between the indicator inlet 346 to the indicator outlet 348 pushes on the flow indicator vanes 352 and creates movement of the flow indicator 322 by causing it to rotate around the axle 330. The indicator inlet 346 and the indicator outlet 348 can be positioned and various places in the flow indicator housing 324 such that the fluid flow interacts with more than one flow indicator vane 352 on the path between the indicator inlet 346 to the indicator outlet 350.

The flow indicator embodiments disclosed herein are one approach to preventing overpressure in the device and/or in the anatomy during a kidney stone removal procedure. In addition to or in place of a flow indicator, mechanisms and devices disclosed herein may include a pressure relief valve capable of relieving fluid pressure when the fluid pressure exceeds a certain predetermined safety threshold. A pressure relief valve may be included on the mechanism handle, on the catheter, at the junction between the handle and the catheter, on the fluid supply line, and/or at the junction of the fluid supply line and handle.

Distal Assembly and Nozzle

Referring back to FIG. 1, the distal assembly 16 of the insertable treatment system 10 is flexible and steerable, is configured to apply irrigation, is configured to allow drainage of the irrigation fluid, is configured to apply aspiration (which can be referred to as vacuum and/or suction), and includes visualization capabilities, such as at least one image sensor and at least one light emitting diode (LED). The catheter 14 includes one or more lumens and/or other elongate structures within the catheter shaft to facilitate the operation of the distal assembly 16. For example, the catheter 14 can contain portions of a steering assembly, such as one or more pull wires. The catheter 14 can contain one or more vacuum lumens in fluid connection with the handle 12 to facilitate aspiration from the distal assembly 16. The catheter 14 can contain one or more irrigation lumens in fluid connection with the handle 12 to facilitate irrigation from the distal assembly 16. Further, these elongate structures can run along the entire length of the catheter 14 or along a partial length of the catheter 14.

Figure 48A:
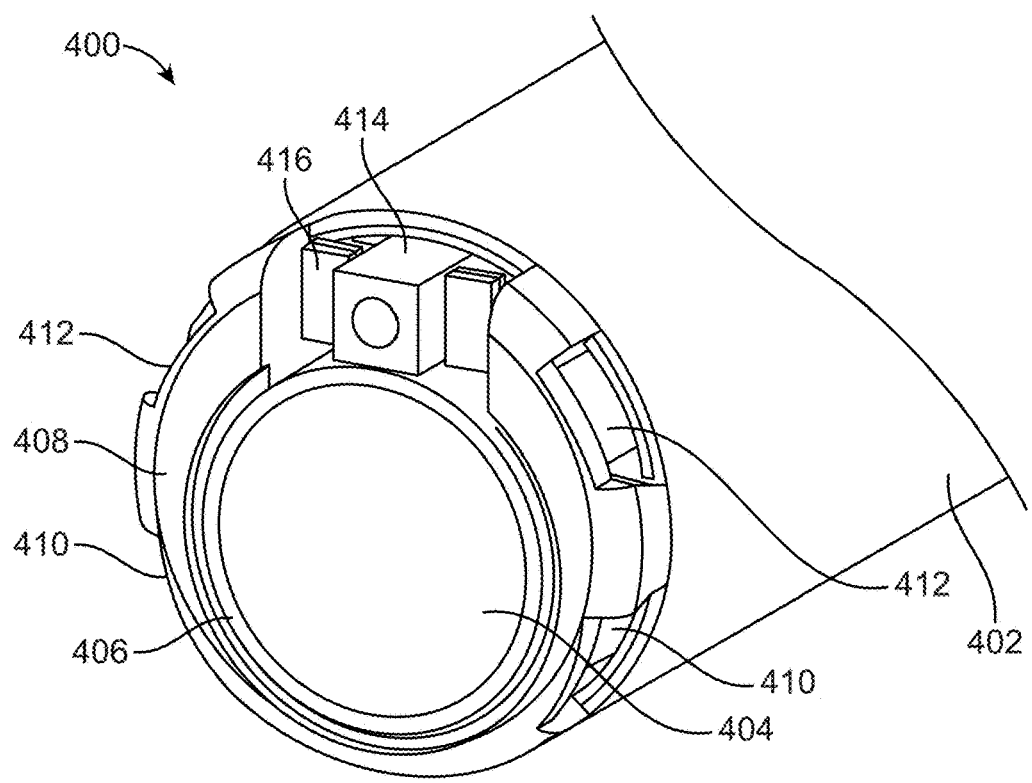
FIGS. 48A and 48B are perspective views of a distal assembly in accordance with an embodiment.
Figure 48B:
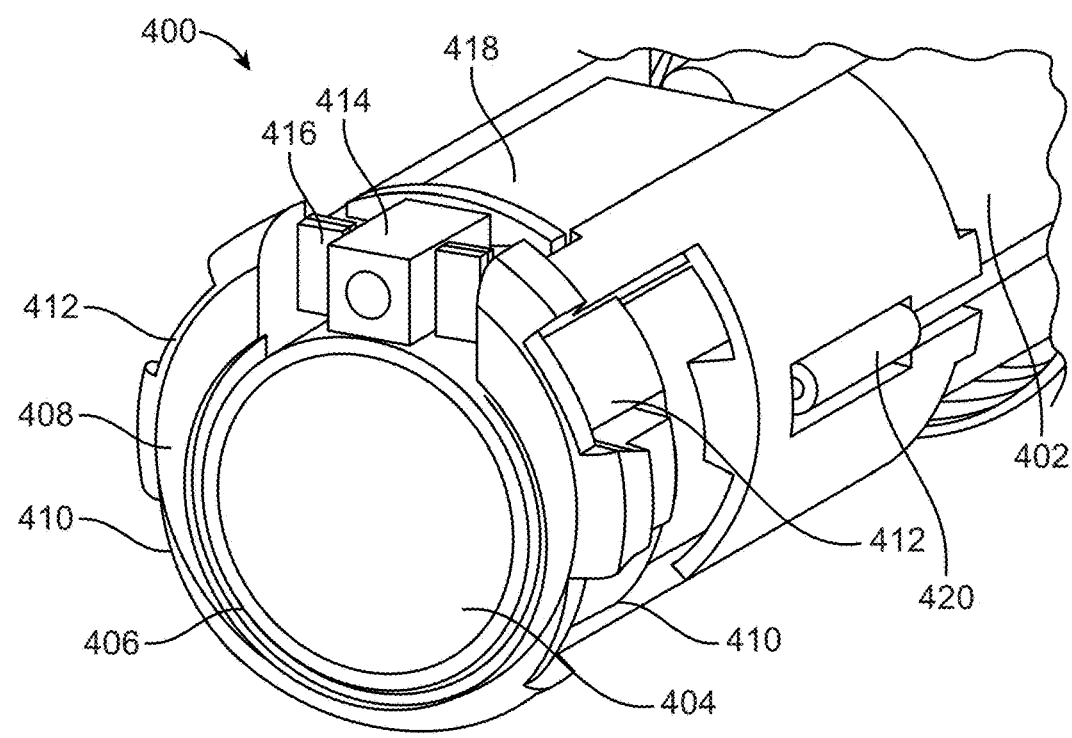

Referring to FIG. 48A and FIG. 48B, each show a perspective view of a distal assembly 400, which is part of the distal section of the insertable treatment system 10. FIG. 48B illustrates a view of the distal assembly 400 with the outer member 402 retracted as compared to FIG. 48A. The outer member 402 can be one or more layers of a tubular structure, and one or more of the layers of the tubular structure can be part of the outer portion of proximal sections of the catheter's shaft. The layers of the outer member 402 can include a comparatively softer and more flexible outer layer over a comparatively stiffer inner layer. The distal assembly 400 comprises a vacuum lumen 404 defined by a vacuum shaft 406. The distal end of the vacuum shaft 406 terminates at or near the distal end of a nozzle tip 408. The nozzle tip 408 includes one or more irrigation ports 410 and 412. The irrigation ports 410 and 412 have a slotted shape and can direct irrigation fluid forward and laterally from the distal end of the nozzle tip 408. The distal assembly further comprises an image sensor 414 and a light source 416 on either side of the image sensor 414. The image sensor 414 can be a semiconductor chip designed for image capture and the light source 416 can be a light emitting diode or similar light source. The region around the image sensor 414 and the light source(s) 416 can be filled with the type of potting material commonly used with electronics, provided that the material is biocompatible or otherwise suitable for use with a medical device. FIG. 48B illustrates a printed circuit board 418 connected with the image sensor 414 and the light source(s) 416. The region around the printed circuit board 418 can also be filled with potting material. FIG. 48B also illustrates the distal end of a pull wire 420 that can be used to steer the distal assembly 16 of the insertable treatment system 10. The nozzle tip 408 includes a recess into which a ferrule or similar fitting on the end of the pull wire 420 can be inserted to provide a distal attachment point for the pull wire 420.

Figure 49A:
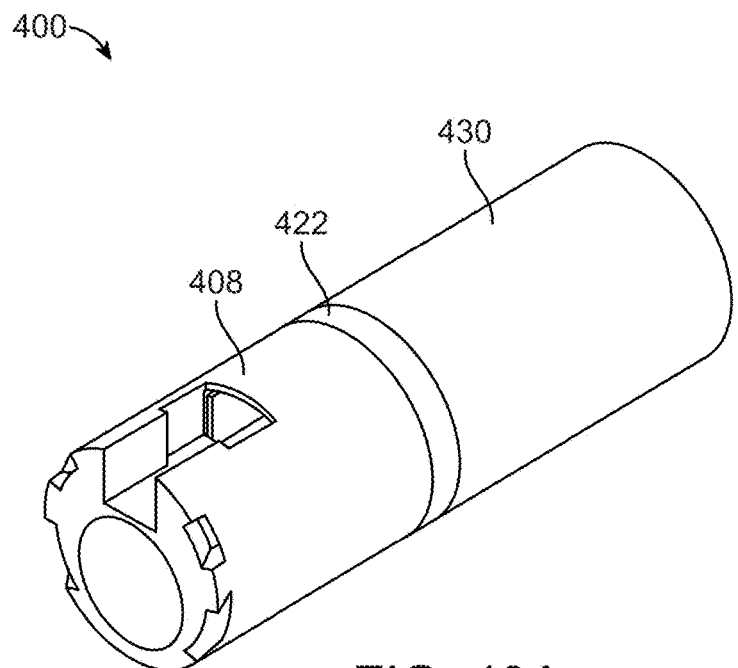
FIGS. 49A and 49B are perspective and perspective exploded views of a distal assembly in accordance with an embodiment.
Figure 49B:
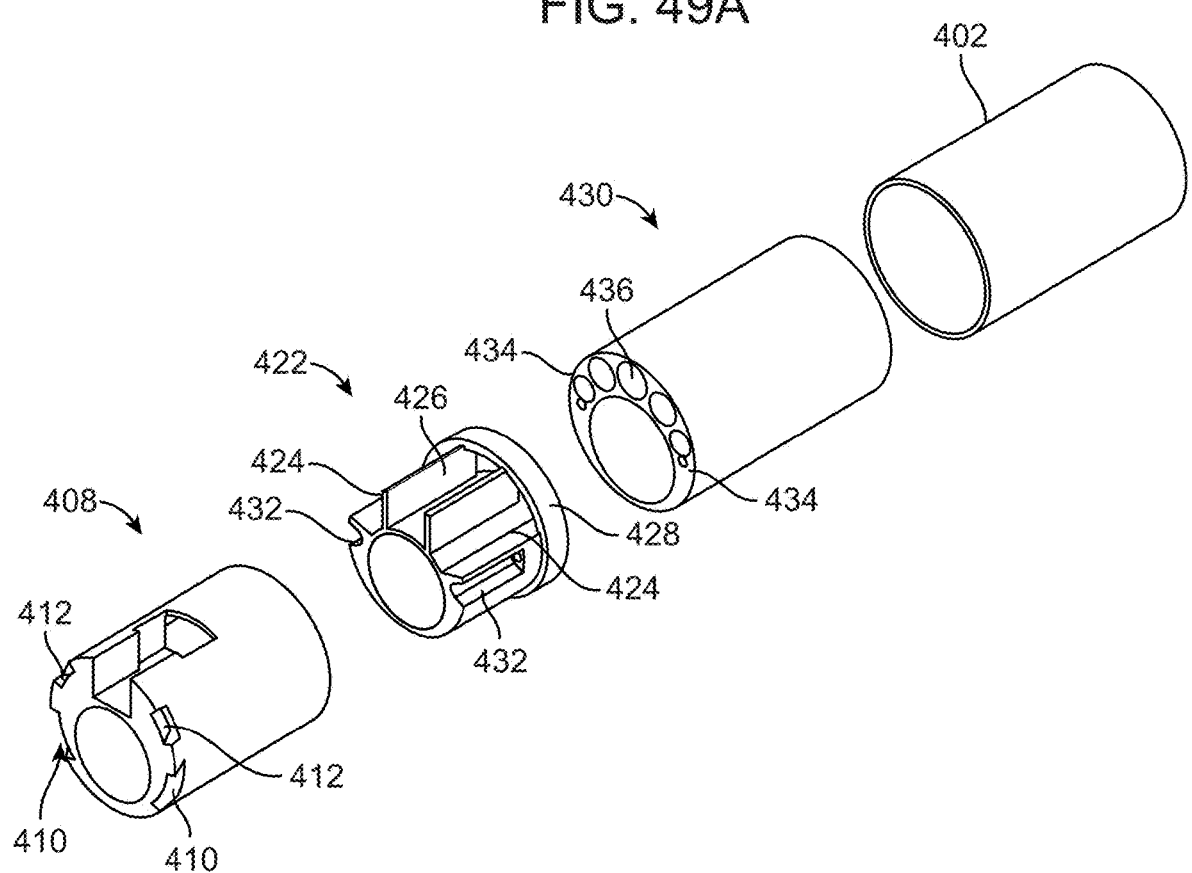

FIG. 49A illustrates a perspective view of multiple parts of the distal assembly 400 and FIG. 49B illustrates a perspective, exploded view of the parts of FIG. 49A. The nozzle tip 408 is configured to accept a distal manifold 422 in the interior of the nozzle tip 408. The distal manifold 422 includes conduits 424, although other examples of the distal manifold 422 can include more or fewer total conduits. The conduits 424 function to direct irrigation fluid to the irrigation ports 410 and 412. The distal manifold 422 also includes an upper recess 426 for accommodating the imaging assembly (or components thereof), including, but not limited to, the at least one printed circuit board 418, the at least one light source 416, and the at least one image sensor 414. The distal manifold 422 also includes a proximal flange 428 that provides a structural member to join and seal against the nozzle tip 408 on one side and a shaft manifold 430 on the other side. The seals on either side of the proximal flange 428 can be fluid tight. The distal manifold 422 also includes pull wire recesses 432 for attaching the steering pull wires to the distal assembly 16 to facilitate steering of the insertable treatment system 10. FIG. 49B illustrates that the shaft manifold 430 includes pull wire lumens 434 and multiple irrigation lumens 436 (only one of the five irrigation lumens 436 illustrated in FIG. 49B is labeled). In some examples of the catheter's 14 shaft, the shaft manifold 430 can extend the entire length of the catheter's 14 shaft or only a portion of length of the catheter's 14 shaft. In some examples of the catheter 14, there is no shaft manifold and the lumen defined by the outer member 402 serves as an irrigation lumen and as a path for steering mechanisms such as pull wires.

Figure 50A:
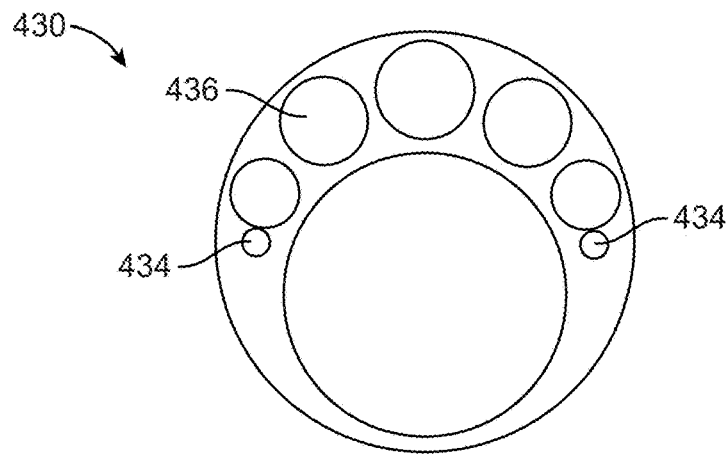
FIGS. 50A, 50B, and 50C are end sectional views of the distal assembly in accordance with an embodiment.
Figure 50B:
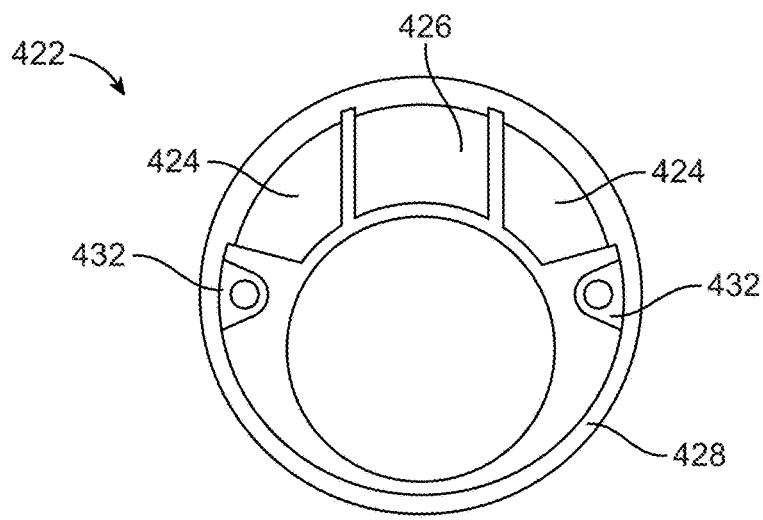
Figure 50C:
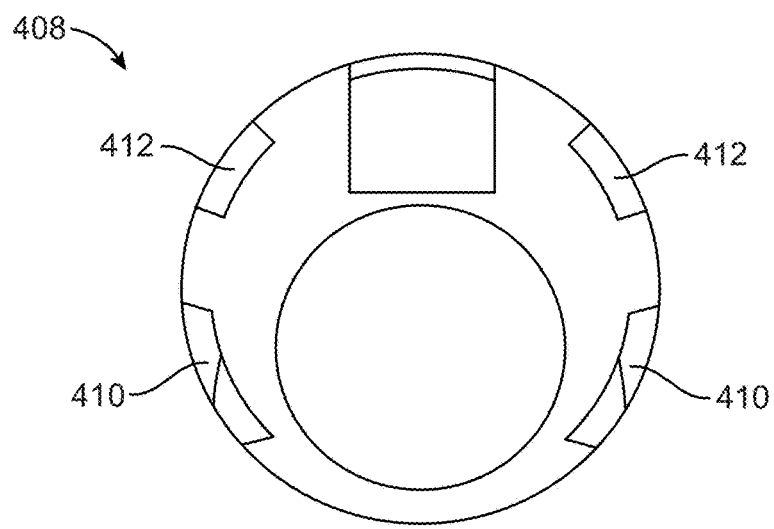

FIG. 50A, FIG. 50B, and FIG. 50C illustrate end views of the parts of the distal assembly 400. FIG. 50A illustrates the shaft manifold 430 with two pull wire lumens 434 and multiple irrigation lumens 436 (only one of the five irrigation lumens 436 illustrated in FIG. 4A is labeled). FIG. 50B illustrates the distal manifold 422 with conduits 424, the upper recess 426, the proximal flange 428, and the pull wire recesses 432. FIG. 50C illustrates the nozzle tip 408 with irrigation ports 410 and 412.

Figure 51A:
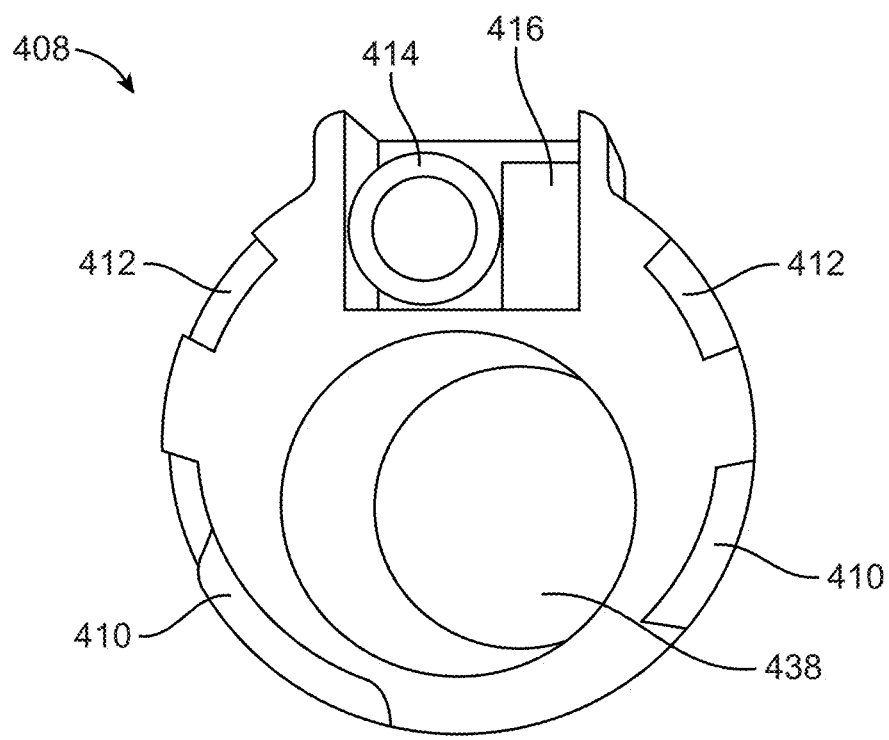
FIGS. 51A, 51B, 52A, 52B, 53A, 53B, 54A, 54B, 55A, 55B, 56, 57, 58A, 58B, 59A, and 59B illustrate nozzle tips in accordance with various embodiments.
Figure 51B:
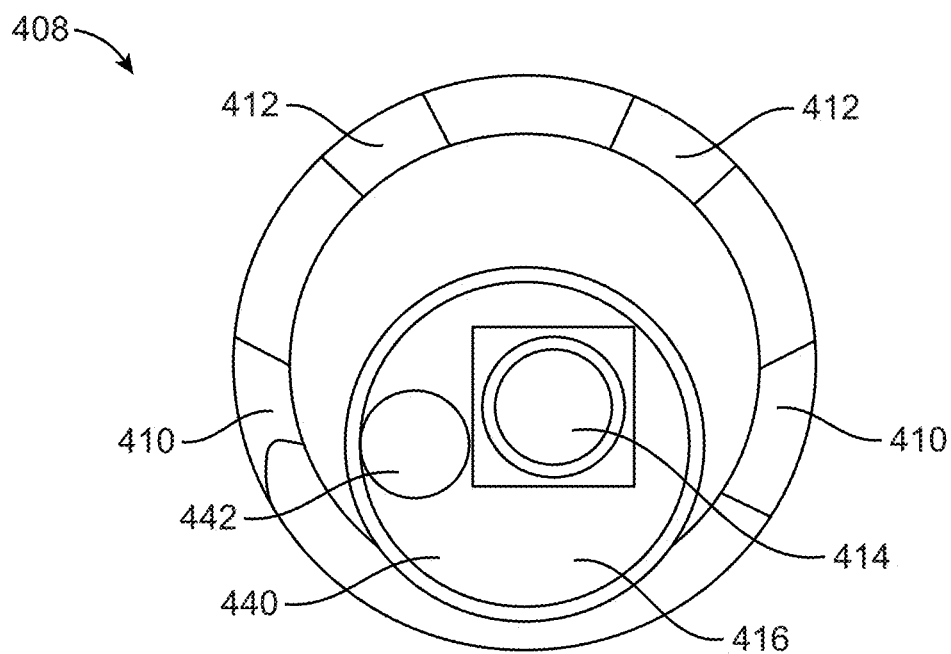

FIG. 51A and FIG. 51B illustrate two different examples of the nozzle tip 408. FIG. 51A illustrates an example of the nozzle tip 408 in which the image sensor 414 and light source 416 are mounted on the nozzle tip 408 and multiple irrigation ports 410 and 412 are present. This example is conceptually similar to the examples illustrated in previous figures. The nozzle tip 408 includes a nozzle lumen 438 that, in some examples, can accommodate the vacuum shaft 406 and, in alternate examples, can define the vacuum lumen 404. FIG. 51B illustrates an alternative example in which the image sensor 414 and the light source 416 are mounted on an elongate insertable member 440 that can be slid with respect to the nozzle tip 408, the distal assembly 400, the catheter's 14 shaft, and/or the insertable system 10. The elongate insertable member 440 includes a working lumen 442 through which therapeutic or diagnostic devices can be slid with respect to the elongate insertable member 440. Example of such devices include, but are not limited to, lasers, sensors, and graspers. Further, the working lumen 442 can allow for the aspiration of fluid and kidney stone fragments while the elongate insertable member 440 is in place. The insertable elongate member 440 can have an outer diameter of from about 1 mm to about 4 mm and the working lumen 442 can have an inner diameter of from about 0.3 mm to about 1.5 mm.

Figure 52A:
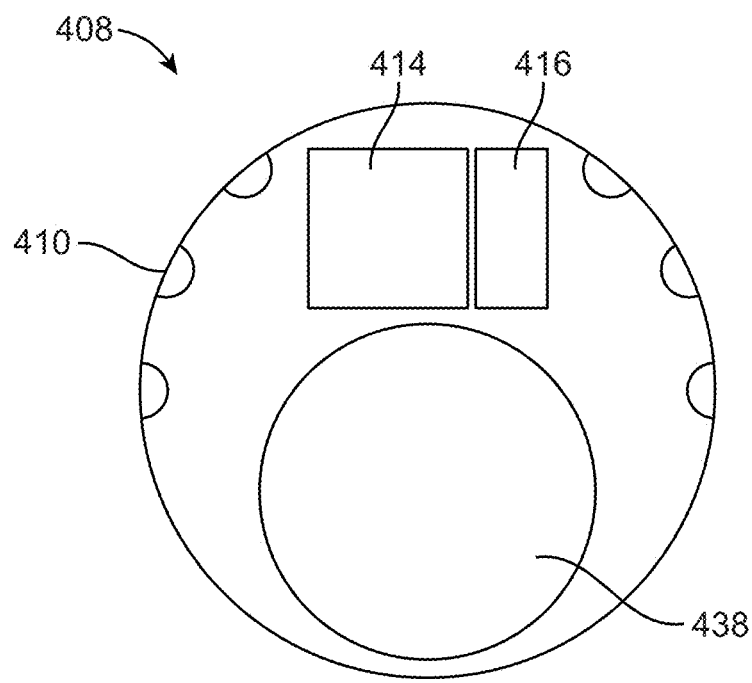
Figure 52B:
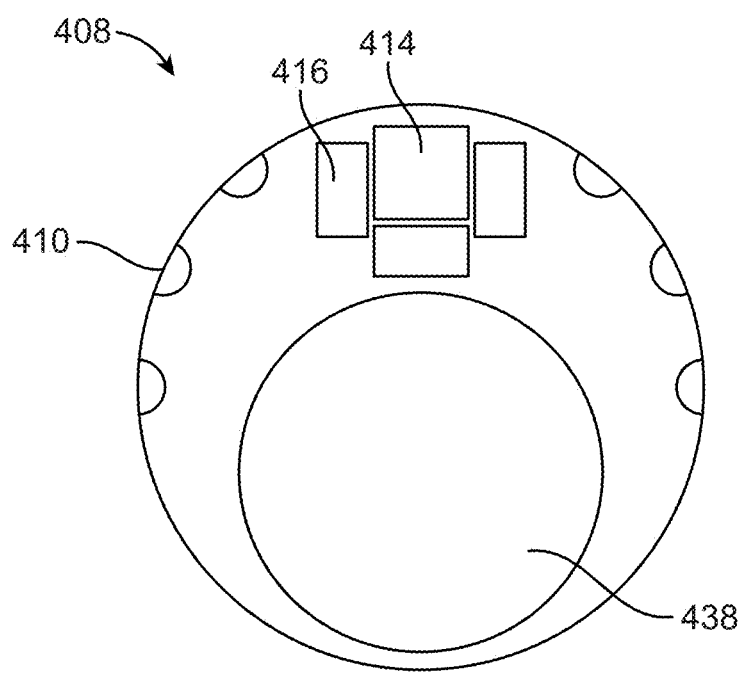

FIG. 52A and FIG. 52B illustrate alternative examples of the nozzle tip 408. In FIG. 52A, the nozzle tip 408 includes a single image sensor 414 and a single light source 416 while in FIG. 52B the nozzle tip 408 includes a single image sensor 414 and three light sources 416 (only one light source 416 is labeled). The arrangement of light sources 416 in FIG. 52B may be preferable in some examples as the arrangement may provide more uniform illumination due to the placement of light sources 416 on either side of the image sensor 414. FIG. 52A and FIG. 52B each illustrate six irrigation ports 410 (only one irrigation port 410 is labeled). These irrigation ports 410 are configured to direct fluid distally and laterally from the nozzle tip 408. In FIG. 52A and FIG. 52B, the nozzle tip 408 includes a nozzle lumen 438 that, in some examples, can accommodate the vacuum shaft 406 and, in alternate examples, can define the vacuum lumen 404.

Figure 53A:
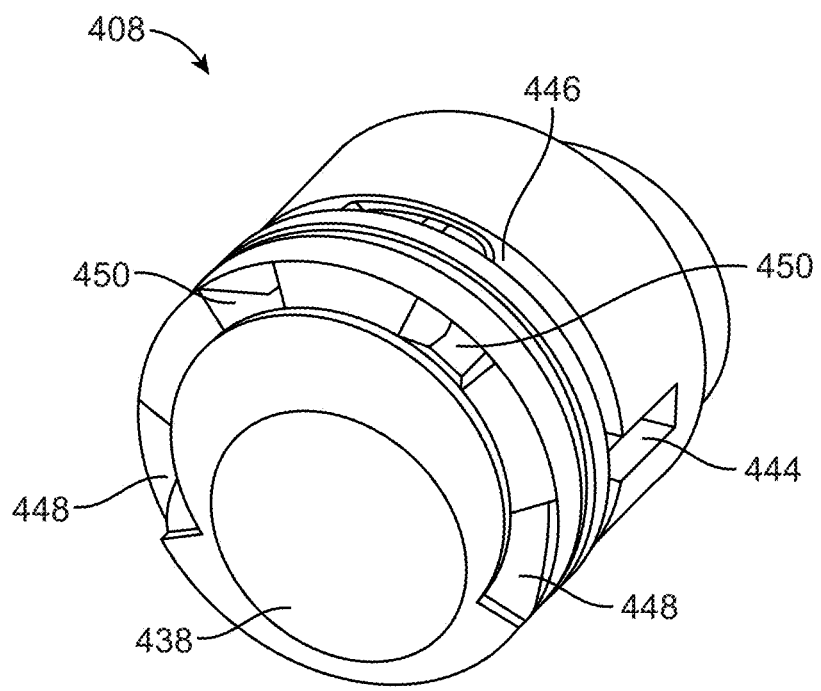
Figure 53B:
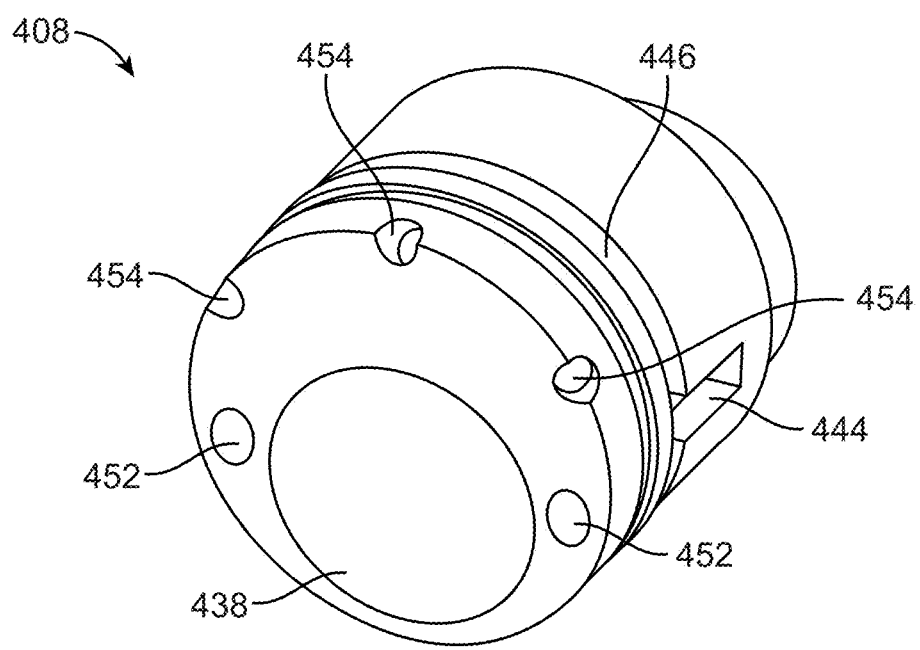

FIG. 53A and FIG. 53B illustrate alternative examples of the nozzle tip 408. In FIG. 53A and FIG. 53B, the nozzle tip 408 includes the nozzle lumen 438 that, in some examples, can accommodate the vacuum shaft 406 and, in alternate examples, can define the vacuum lumen 404. The nozzle tip 408 also includes at least one pull wire recess 444. The nozzle tip 408 includes a tip manifold 446 that is configured to direct fluid to the irrigation ports. The tip manifold 446 is in fluid communication with one or more irrigation lumens that conduct irrigation fluid from the handle 12 and down the catheter 14 and provides a fluid path to each of the irrigation ports. In FIG. 53A and FIG. 53B, the nozzle lumen 438 is offset from the center of the nozzle tip 408. FIG. 53A illustrates slot-shaped irrigation ports 448 and 450. The irrigation ports 448 are larger than the irrigation ports 450. The interior of each of the irrigation ports 448 and 450 is configured to direct fluid radially away from the central axis of the nozzle tip 408. FIG. 53B illustrates circle-shaped irrigation ports 452 and 454 and they are similarly sized. The irrigation ports 452 are on the front face of the nozzle tip 408. The openings of the irrigation ports 454 are on the front face and extend into the side, lateral wall of the nozzle tip 408. The interior of each of the irrigation ports 452 and 454 is configured to direct fluid radially away from the central axis of the nozzle tip 408. The configuration of the irrigation ports 454 allows the irrigation ports 454 to direct fluid more radially outward than the ports 452. In some examples, the direction of fluid may approximate a spiral directed away from the central axis of the nozzle tip 408 in both the slot-shaped and circle-shaped examples.

Figure 54A:
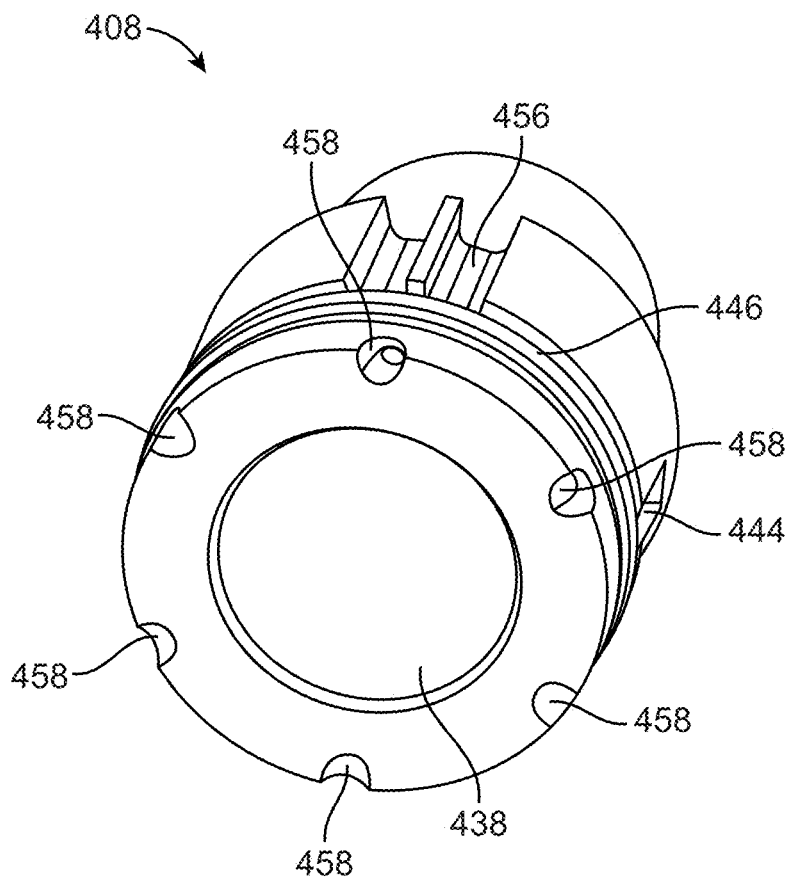
Figure 54B:
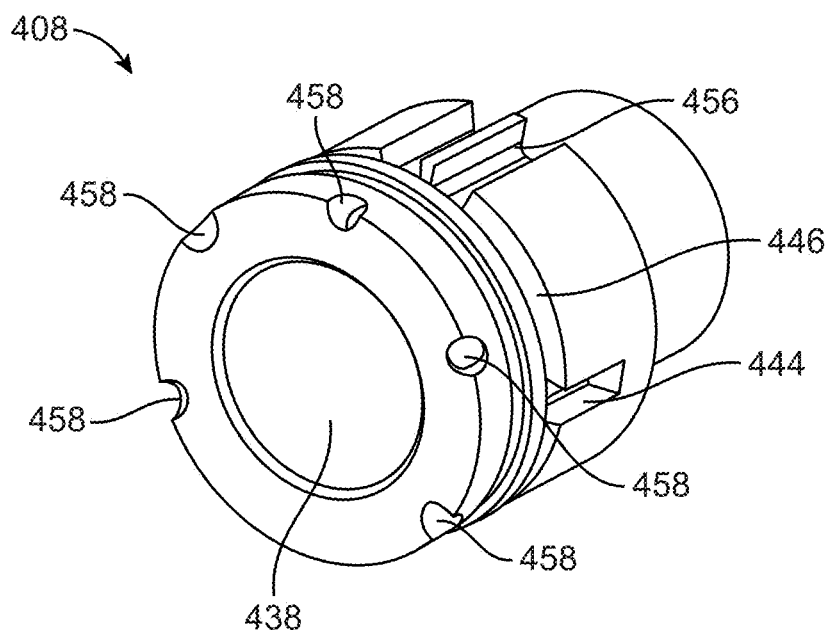

FIG. 54A and FIG. 54B illustrate alternative examples of the nozzle tip 408. In FIG. 54A and FIG. 54B, the nozzle tip 408 includes the nozzle lumen 438 that, in some examples, can accommodate the vacuum shaft 406 and, in alternate examples, can define the vacuum lumen 404. The nozzle tip 408 also includes at least one pull wire recess 444. The nozzle tip 408 includes the tip manifold 446 that is configured to direct fluid to the irrigation ports. The tip manifold 446 is in fluid communication with one or more irrigation conduits 456 to provide a fluid path to each of the irrigation ports. In FIG. 54A and FIG. 54B, the nozzle lumen 438 is concentric with the outer diameter of the nozzle tip 408. FIG. 54A illustrates six circle-shaped irrigation ports 458. The irrigation ports 458 can be elliptical-shaped, slot-shaped, or arc-shaped. The openings of the irrigation ports 458 extend from the front face into the side, lateral wall of the nozzle tip 408. FIG. 54B illustrates five circle-shaped irrigation ports 458 and they are similarly sized. The interior of each of the irrigation ports 458 is configured to direct fluid radially away from the central axis of the nozzle tip 408. The exit angle for the irrigation ports depicted in FIGS. 54A and 54B is approximately 45 degrees with respect to the central axis of the nozzle tip 408 and the direction of the irrigation fluid away from the nozzle tip 408 is radially away from the central axis of the nozzle tip 408.

Figure 55A:
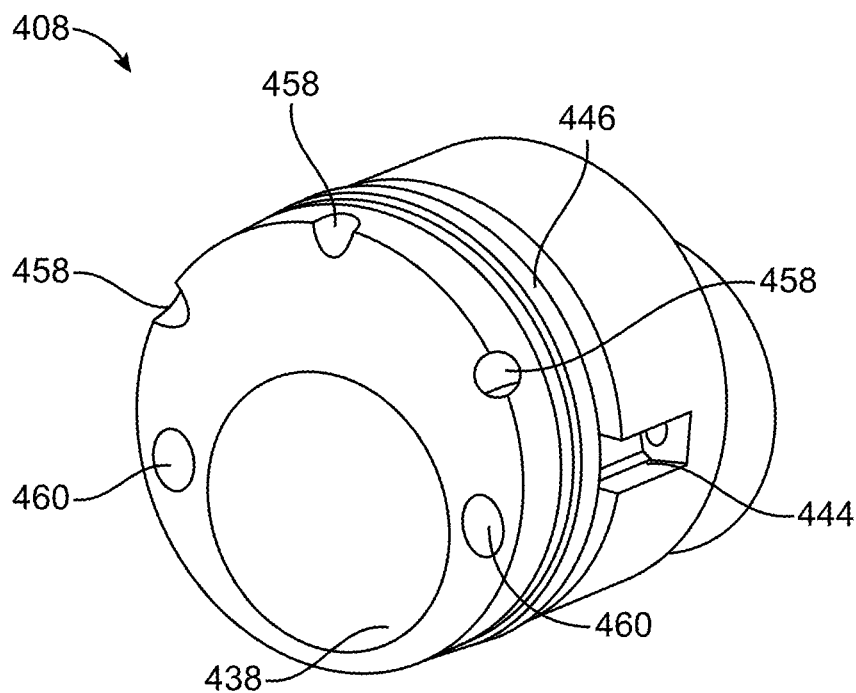
Figure 55B:
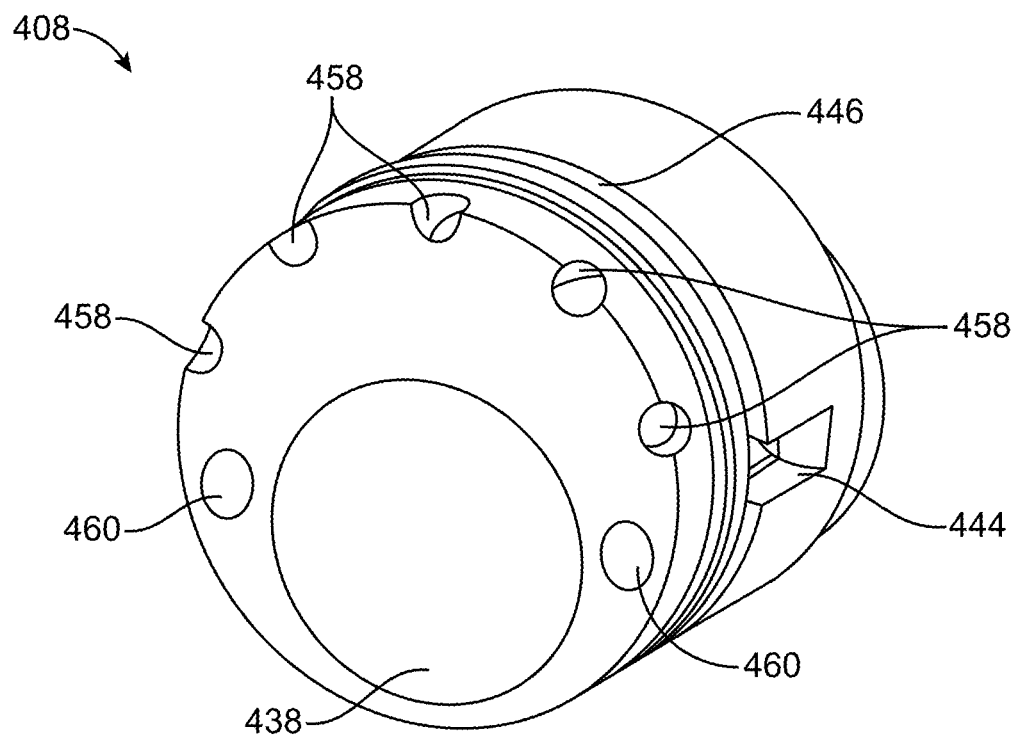

FIG. 55A and FIG. 55B illustrate alternative examples of the nozzle tip 408. In FIG. 55A and FIG. 55B, the nozzle tip 408 includes a nozzle lumen 438 that, in some examples, can accommodate the vacuum shaft 406 and, in alternate examples, can define the vacuum lumen 404. The nozzle lumen 438 is offset from the center of the nozzle tip 408. The nozzle tip 408 also includes at least one pull wire recess 444. The nozzle tip 408 includes the tip manifold 446 that is configured to direct fluid to the irrigation ports. The tip manifold 446 is in fluid communication with one or more irrigation lumens that conduct irrigation fluid from the handle 12 and down the catheter 14 and provides a fluid path to each of the irrigation ports. FIG. 55A illustrates three circle-shaped irrigation ports 458 with an exit angle of about 45 degrees and configured to direct fluid radially away from the central axis of the nozzle tip 408 and two elliptical irrigation ports 460 that direct fluid at a 45-degree angle down from the central axis of the nozzle tip 408 but not in a radially diverging direction. The openings of the elliptical irrigation ports 460 are on the front face of the nozzle tip 408. The openings of the circle-shaped irrigation ports 458 encompass both the front face and side lateral wall. FIG. 55B illustrates five circle-shaped irrigation ports 458 with an exit angle of about 45 degrees and configured to direct fluid radially away from the central axis of the nozzle tip 408 and two elliptical irrigation ports 460 that direct fluid at a 45-degree angle down from the central axis of the nozzle tip 408 but not in a radially diverging direction.

Figure 56:
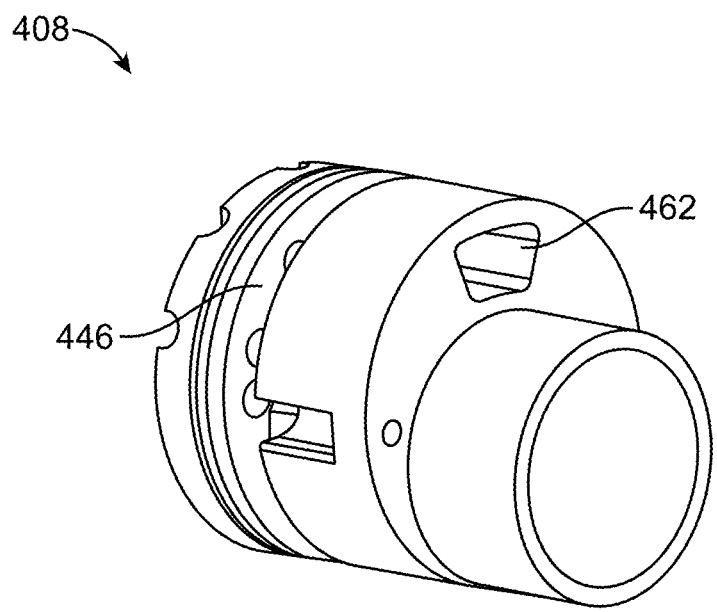

FIG. 56 illustrates a rear, perspective view of the nozzle tip 408 (e.g., can be any of the described nozzle tips) with a tip manifold 446 that provides a fluid path to various irrigation ports on the distal face of the nozzle tip 408. The nozzle tip 408 also includes a nozzle irrigation lumen 462 that provides a path for fluid from the catheter 14 to the tip manifold 446.

Figure 57:
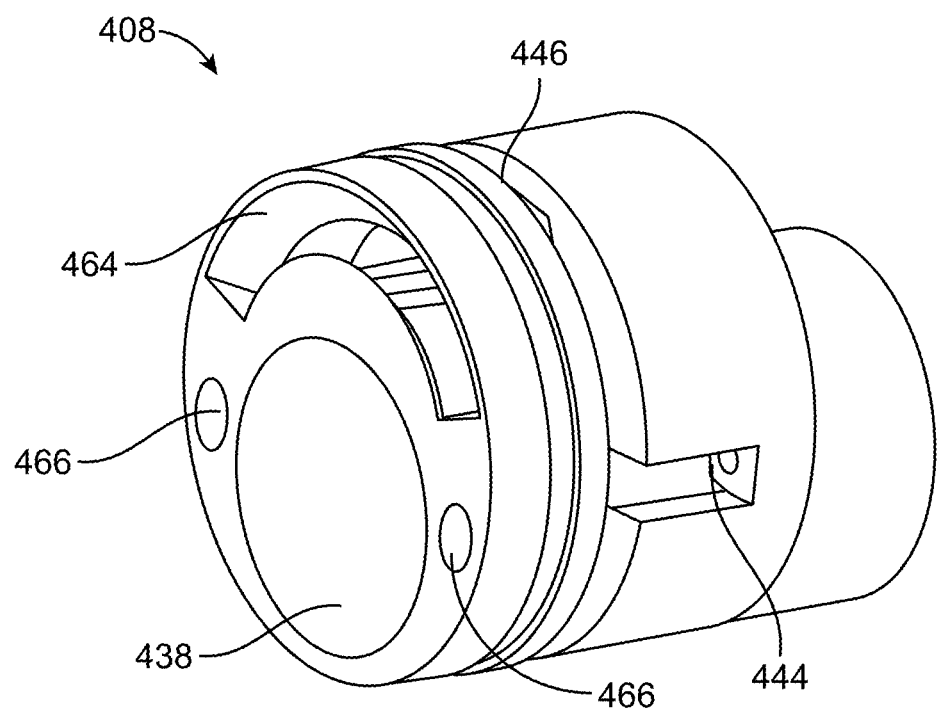

FIG. 57 illustrates an alternative example of the nozzle tip 408. The nozzle tip 408 includes the nozzle lumen 438 that, in some examples, can accommodate the vacuum shaft 406 and, in alternate examples, can define the vacuum lumen 404. The nozzle lumen 438 is offset from the center of the nozzle tip 408. The nozzle tip 408 also includes at least one pull wire recess 444. The nozzle tip 408 includes the tip manifold 446 that is configured to direct fluid to the irrigation ports. The tip manifold 446 is in fluid communication with one or more irrigation lumens that conduct irrigation fluid from the handle 12 and down the catheter 14 and provides a fluid path to each of the irrigation ports. FIG. 57 illustrates a slotted irrigation port 464 with an exit angle of about 45 degrees and configured to direct fluid radially away from the central axis of the nozzle tip 408. The irrigation port 464 has a 140-degree arc that provides a substantial sweep of fluid. The nozzle tip 408 includes two elliptical irrigation ports 466 that direct fluid at a 45-degree angle down from the central axis of the nozzle tip but not in a radially diverging direction.

Figure 58A:
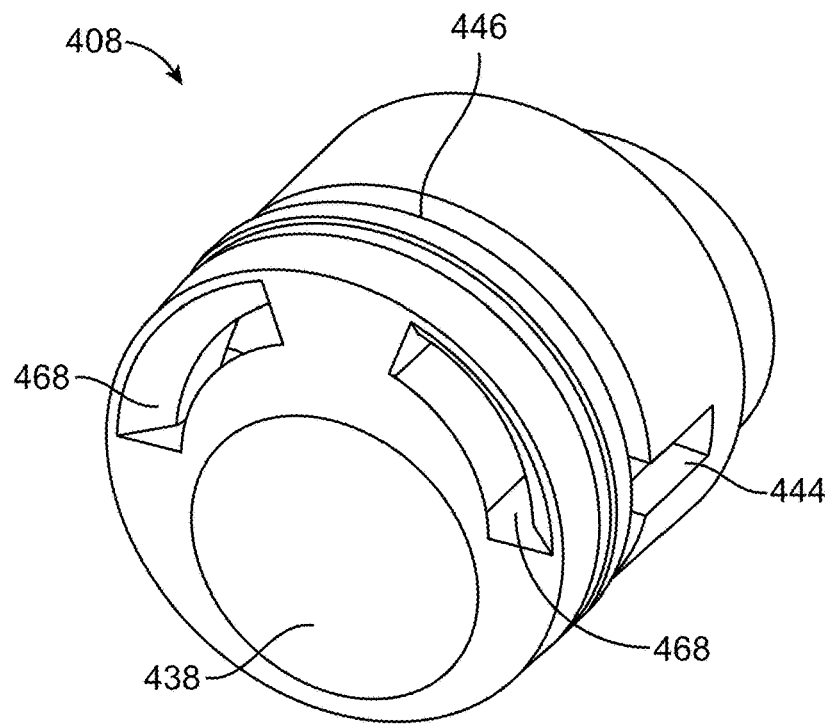
Figure 58B:
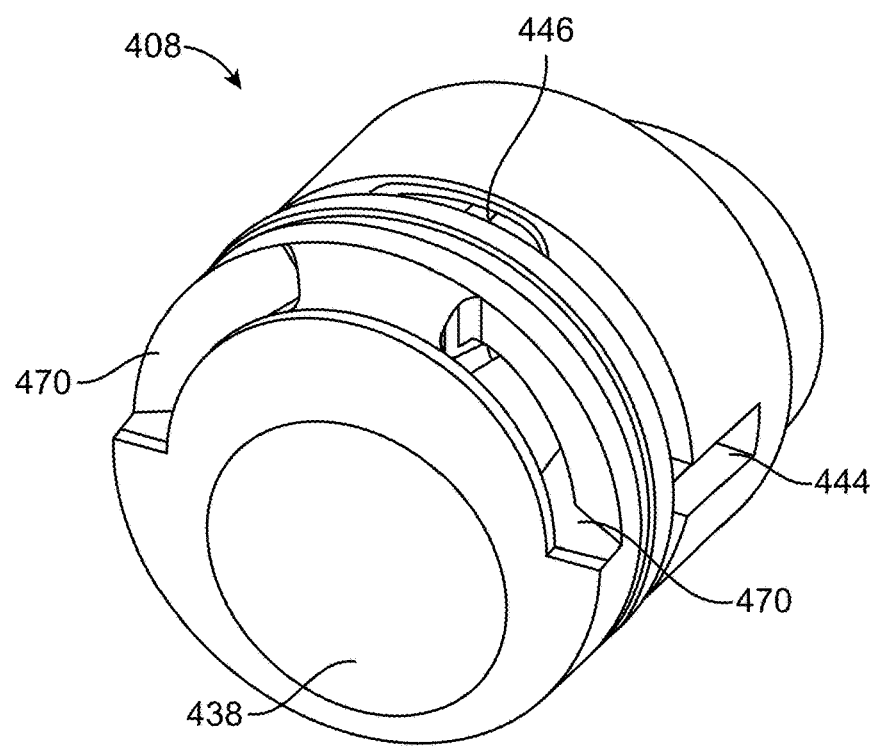

FIG. 58A and FIG. 58B illustrate alternative examples of the nozzle tip 408. In FIG. 58A and FIG. 58B, the nozzle tip 408 includes a nozzle lumen 438 that, in some examples, can accommodate the vacuum shaft 406 and, in alternate examples, can define the vacuum lumen 404. The nozzle lumen 438 is offset from the center of the nozzle tip 408. The nozzle tip 408 also includes at least one pull wire recess 444. The nozzle tip 408 includes the tip manifold 446 that is configured to direct fluid to the irrigation ports. The tip manifold 446 is in fluid communication with one or more irrigation lumens that conduct irrigation fluid from the handle 12 and down the catheter 14 and provides a fluid path to each of the irrigation ports. FIG. 58A illustrates two slotted irrigation ports 468, each with an exit angle of about 45 degrees and configured to direct fluid radially away from the central axis of the nozzle tip 468. Each irrigation port has an arc of about 70 degrees and are separated by a central region with an arc of about 40 degrees. Together, the irrigation ports 468 can provide a sweep of fluid of about 180 degrees. FIG. 58B illustrates two slotted irrigation ports 470, each with an exit angle of about 65 degrees and configured to direct fluid radially away from the central axis of the nozzle tip 408. Each irrigation port 470 has an arc of about 70 degrees and the irrigation ports 470 are separated by a central region with an arc of about 40 degrees. Together, the irrigation ports 470 can provide a sweep of fluid of about 180 degrees. FIGS. 58A and 58B illustrate that the irrigation ports 468 and 470 are configured to direct fluid both distally and laterally from the distal face of the nozzle tip 408.

Figure 59A:
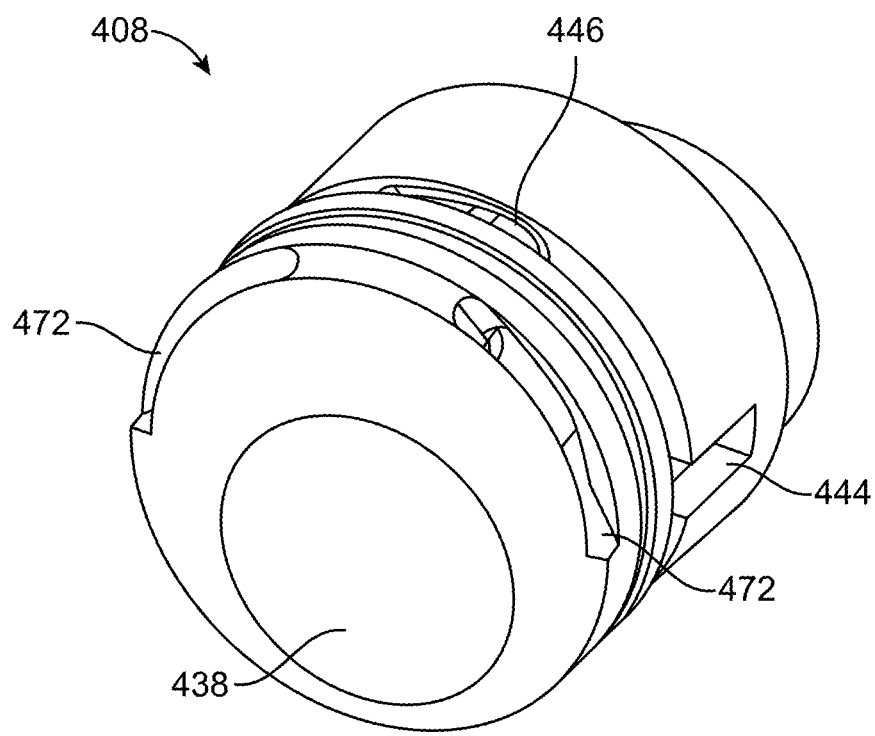
Figure 59B:
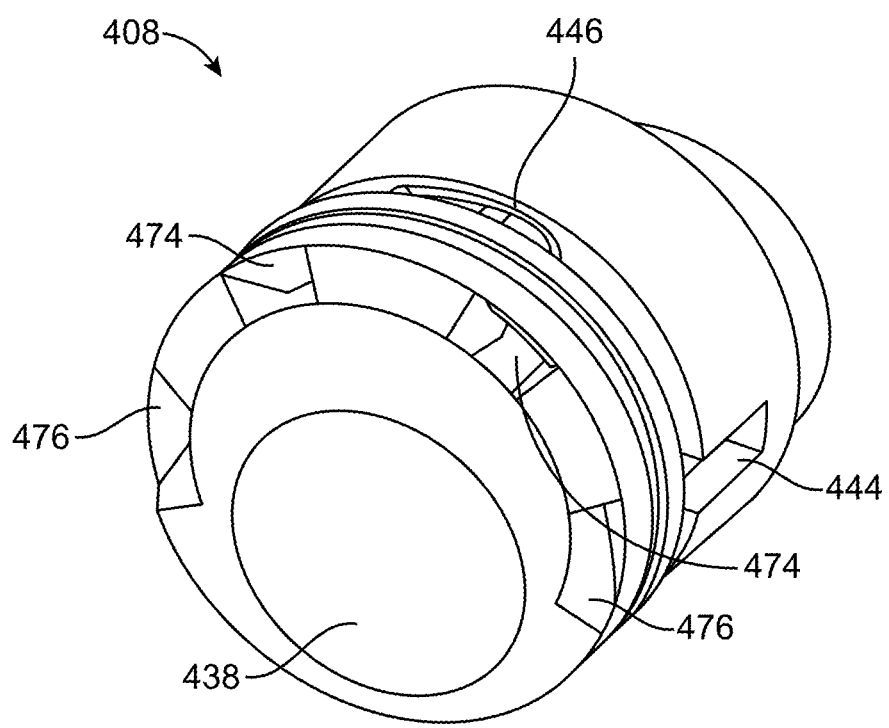

FIG. 59A and FIG. 59B illustrate alternative examples of the nozzle tip 408. In FIG. 59A and FIG. 59B, the nozzle tip 408 includes a nozzle lumen 438 that, in some examples, can accommodate the vacuum shaft 406 and, in alternate examples, can define the vacuum lumen 404. The nozzle lumen 438 is offset from the center of the nozzle tip 408. The nozzle tip 408 also includes at least one pull wire recess 444. The nozzle tip 408 includes the tip manifold 446 that is configured to direct fluid to the irrigation ports. The tip manifold 446 is in fluid communication with one or more irrigation lumens that conduct irrigation fluid from the handle 12 and down the catheter 14 and provides a fluid path to each of the irrigation ports. FIG. 59A illustrates two slotted irrigation ports 472, each with an exit angle of about 45 degrees and configured to direct fluid radially away from the central axis of the nozzle tip 408. Each irrigation port 472 has an arc of about 70 degrees and the irrigation ports 472 are separated by a central region with an arc of about 40 degrees. Together, the irrigation ports 472 can provide a sweep of fluid of about 180 degrees. FIG. 59A illustrates that the irrigation ports 472 are configured to direct fluid both distally and laterally from the distal face of the nozzle tip 408. FIG. 59B illustrates four slotted irrigation ports 474 and 476, each with an exit angle of about 45 degrees and configured to direct fluid radially away from the central axis of the nozzle tip 408. Each irrigation port has an arc of about 20 degrees. Irrigation ports 474 are separated by a central region with an arc of about 50 degrees. Neighboring irrigation ports 474 and 476 are separated by a region with an arc of about 40 degrees. Together, the irrigation ports 474 and 476 can provide a sweep of fluid of about 180 degrees. FIG. 59A and FIG. 59B illustrate that the irrigation ports are configured to direct fluid both distally and laterally from the distal face of the nozzle tip 408.

The various examples of irrigation port configurations presented herein demonstrate that the nozzle tip can achieve various spray patterns by manipulating variables such as the size, shape, and number of irrigation ports, the exit angles of the irrigation ports, the placement of the irrigation ports on the distal face of the nozzle tip (i.e., entirely on the distal face or partially on the distal face and partially on the lateral portions of the nozzle tip as shown by the figures). Further, one or more of the irrigation ports may be configured the same as or different from the configuration of one or more of the irrigation ports on the same nozzle tip.

Figure 60:
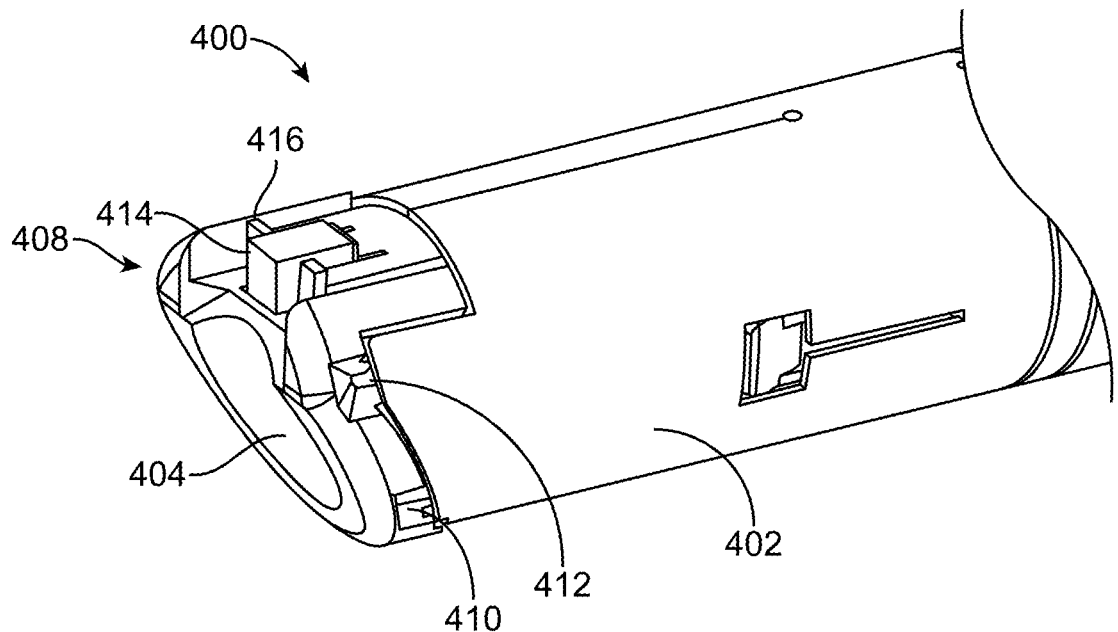
FIG. 60 illustrates a distal assembly according to an embodiment.
Figure 61:
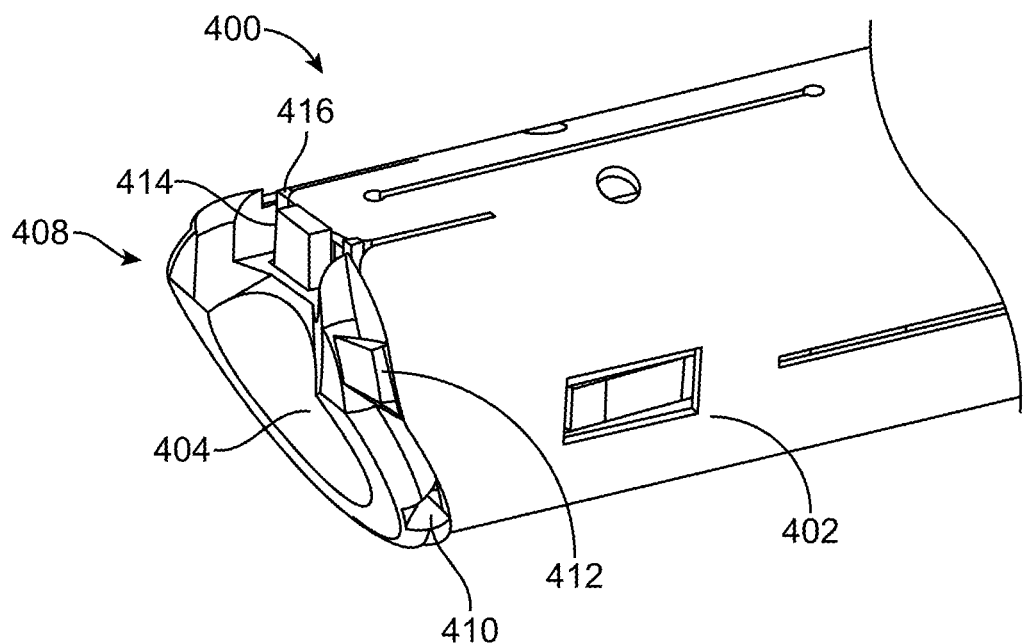
FIG. 61 illustrates a distal assembly according to an embodiment.

FIG. 60 and FIG. 61 each are perspective views of an embodiment of the distal assembly 400, which is in the distal section of the insertable treatment system 10. Both FIG. 60 and FIG. 61 illustrate the outer member or an outer hypotube 402 included in the distal assembly 400. As disclosed herein, the outer member 402 of the distal assembly 400 can include one or more layers of a tubular structure. In FIG. 60 and FIG. 61 the outer hypotube 402 can be at least partially covered by a more flexible outer layer (not pictured). FIG. 60 and FIG. 61 illustrate the vacuum lumen 404 defined by the nozzle tip 408 in the distal assembly 400 and defined by a vacuum shaft (not pictured) in portions of the device proximal of the distal assembly 400. The nozzle tip 408 in FIG. 60 and FIG. 61 includes an angled distal face to reduce the distal-most surface area of the nozzle tip 408, which can reduce the likelihood of trauma to tissue as the device is advanced distally. The edges of the distal face are radiused or smoothed with curvature as compared to a sharply angled corner for the same reason of reducing the likelihood of trauma. This angled distal face or edges being radiused and smoothed can be implemented with any of the nozzle tip 408 configurations disclosed above. The nozzle tip 408 is illustrated to include four irrigation ports arranged in two pairs—a pair of upper irrigation ports 412 and a pair of lower irrigation ports 410—but in the perspective view of FIG. 60 and FIG. 61 only one of each pair is visible. The pairs of irrigation ports 410 and 412 have a slotted shape and can direct irrigation fluid forward and laterally from the distal end of the nozzle tip 150. The image sensor 414 is set on the nozzle tip 408 and the light source 416 can be on either side of the image sensor 414. As with the pervious embodiments, the image sensor 414 can be a semiconductor chip designed for image capture and the light source 416 can be a light emitting diode or similar light source. The region around the image sensor 414 and the light source(s) 416 can be filled with the type of potting material commonly used with electronics, provided that the material is biocompatible or otherwise suitable for use with a medical device.

Figure 62A:
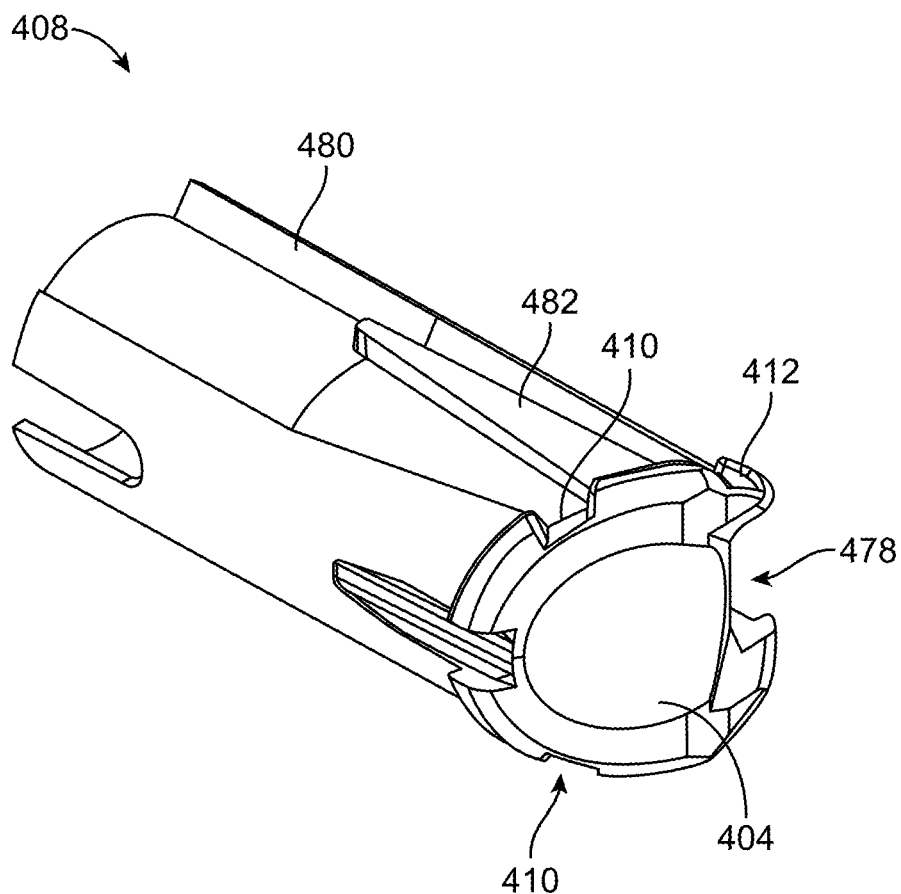
FIGS. 62A, 62B, and 62C illustrate views of an embodiment of a nozzle tip of a distal assembly.
Figure 62B:
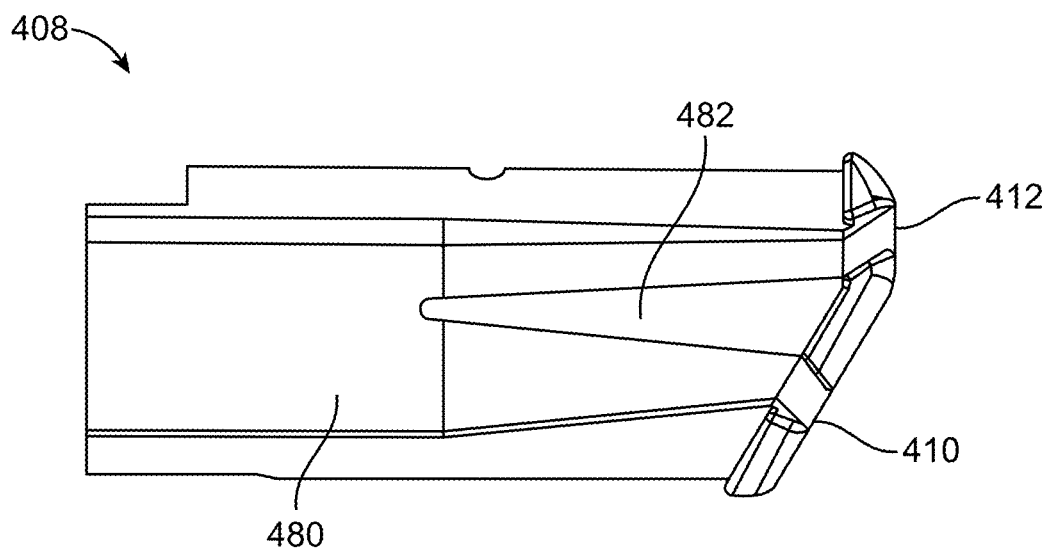

FIG. 62A and FIG. 62B illustrate a perspective view and a side view, respectively, of an embodiment of the nozzle tip 408 of the distal assembly 400. The nozzle tip 408 includes the pair of upper irrigation ports 412 and the pair of lower irrigation ports 410 arranged around a vacuum lumen 404. The nozzle tip 408 includes an upper recess 478 that provides a place to mount an image sensor and light source. FIG. 62B illustrates the angled distal face of the nozzle tip 408. The nozzle tip 408 includes two conduits 480, one on each side of the nozzle tip 408, that provide a fluid path between the irrigation ports 410 and 412 and the irrigation lumen in the shaft section of the catheter. The nozzle tip 408 can include multiple conduits 480. In the example illustrated in FIG. 62A and FIG. 62B, each conduit 480 includes a divider 482 that helps direct fluid to each of the irrigation ports 410 and 412. Depending on the number of irrigation ports in a nozzle tip, there can be multiple dividers in a conduit to distribute fluid to the irrigation ports. The dimensions of the divider influences the flow characteristics of the irrigation fluid at each irrigation port and can be varied to achieve the desired flow characteristics at each port.

Figure 62C:
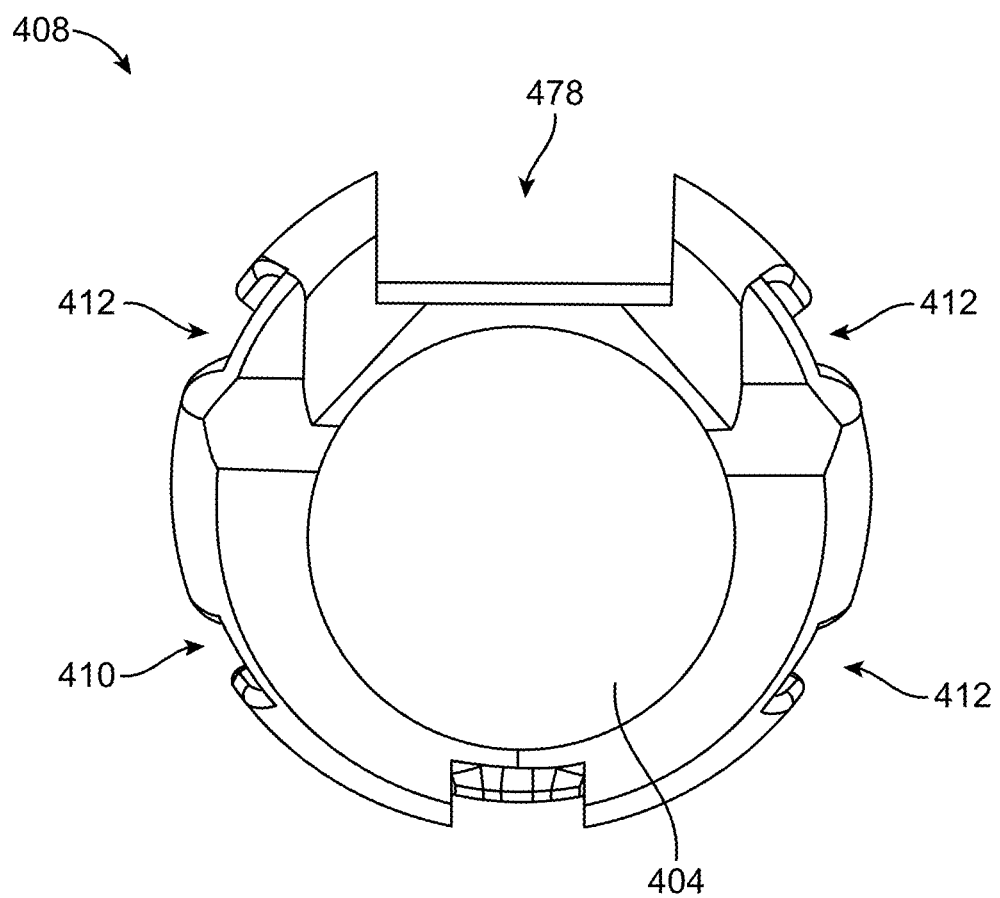

FIG. 62C illustrates an end view of a nozzle tip 408 and shows that the upper irrigation ports 412 and the lower irrigation ports 410 include front-facing openings. As disclosed herein, the interior of the irrigation ports 410 and 412 can be angled such that irrigation fluid exits the nozzle tip at a departure angle with respect to the central axis of the nozzle tip, as described herein. The irrigation ports 410 and 412 can be characterized by their shape, their radial distribution, their departure angle, and their front-facing area, among other parameters.

In some examples of the nozzle (e.g., any of the nozzle tips 408 described above), the radial distribution of irrigation ports is such that the irrigation ports are substantially evenly distributed about the circumference of the nozzle. In some examples (e.g., any of the nozzles 408 described above), in a cross-sectional view of the nozzle tip the largest angle between any two adjacent irrigation ports measured from center to center of each irrigation port is less than about 110 degrees and depends on the number of irrigation ports on the nozzle. With more than three irrigation ports, there can be a pair of adjacent irrigation ports for which the angle measured from center to center of each irrigation port substantially about 110 degrees and the several other irrigation ports have angles measured from center to center of each irrigation port that are substantially less than about 110 degrees.

In some examples of the nozzle (e.g., any of the nozzle tips 408 described above), the irrigation ports have a main axis that is at an angle with respect to the central longitudinal axis of the nozzle. This angle or the nozzle exit angle can be in the range of from about 30 degrees to about 60 degrees and can be referred to as the irrigation port departure angle. Nozzles can be configured with irrigation ports having different departure angles or identical departure angles as other irrigation ports on the same nozzle. Sets of irrigation ports can have the same departure angle, and that angle can be different from another set of irrigation ports on the same nozzle. In some preferred examples, the irrigation port departure angle is about 45 degrees. In other preferred examples, the irrigation departure port angle is 30 degrees, 31 degrees, 32 degrees, 33 degrees, 34 degrees, 35 degrees, 36 degrees, 37 degrees, 38 degrees, 39 degrees, 40 degrees, 41 degrees, 42 degrees, 43 degrees, 44 degrees, 45 degrees, 46 degrees, 47 degrees, 48 degrees, 49 degrees, 50 degrees, 51 degrees, 52 degrees, 53 degrees, 54 degrees, 55 degrees, 56 degrees, 57 degrees, 58 degrees, 59 degrees, or 60 degrees. In one preferred example, on one nozzle there is one set of irrigation ports that has a departure angle of 34 degrees and another set of irrigation ports that has a departure angle of 50 degrees. Table 1 shows the departure angles for pairs of irrigation ports for several different nozzle designs.

TABLE 1

Departure angles of irrigation ports in certain nozzle designs

| Design | Top Port Angle (degrees) | Bottom Port Angle (degrees) |
| --- | --- | --- |
| L1 | 39.15 | 41.75 |
| L2 | 35.05 | 38.45 |
| L3 | 26.8 | 38.35 |
| L4 | 22.4 | 39.9 |
| L5 | 33.25 | 53.45 |
| K1 | 45 | 45 |

TABLE 1-continued

Departure angles of irrigation ports in certain nozzle designs

| Design | Top Port Angle (degrees) | Bottom Port Angle (degrees) |
|---|---|---|
| K2 | 45 | 45 |
| K3 | 45 | 45 |
| K4 | 45 | 45 |
| K5 | 45 | 45 |
| K6 | 45 | 45 |

Hydraulic diameter can be a useful parameter for characterizing various irrigation port configurations. Generally, hydraulic diameter is used when characterizing flow in non-circular channels in fluid calculations that are common for circular channels. If the cross-section is uniform along a channel length, the hydraulic diameter, $D_H$, is defined as: $D_H = 4A/P$, where A is the cross-sectional area of the flow and P is the wetted perimeter of the cross-section.

To characterize preferred examples of nozzle tip designs, several nozzle tips were fabricated. The nozzle tips included two pairs of irrigation ports where the top and bottom (i.e., upper and lower) were symmetrical pairs having the same slotted shape and departure angle. Table 2 shows the relevant dimensions of several different nozzle designs. The area and perimeter of each individual port in a pair is shown in the table.

TABLE 2

Dimensions of irrigation ports in certain nozzle designs

| Design | Top Port Area (mm²) | Top Port Perimeter (mm) | Top Port Hydraulic Diameter | Bottom Port Area (mm²) | Bottom Port Perimeter (mm) | Bottom Port Hydraulic Diameter |
|---|---|---|---|---|---|---|
| L1 | 0.046 | 0.88 | 0.209 | 0.058 | 0.99 | 0.236 |
| L2 | 0.069 | 1.12 | 0.247 | 0.085 | 1.22 | 0.279 |
| L3 | 0.098 | 1.42 | 0.275 | 0.120 | 1.52 | 0.314 |
| L4 | 0.117 | 2.87 | 0.163 | 0.142 | 1.73 | 0.330 |
| L5 | 0.117 | 1.61 | 0.290 | 0.142 | 1.72 | 0.330 |
| K1 | 0.246 | 2.09 | 0.470 | 0.137 | 1.99 | 0.275 |
| K2 | 0.045 | 0.96 | 0.186 | 0.010 | 0.43 | 0.092 |
| K3 | 0.079 | 1.27 | 0.250 | 0.029 | 0.75 | 0.155 |
| K4 | 0.164 | 1.67 | 0.393 | 0.077 | 1.38 | 0.224 |
| K5 | 0.079 | 1.27 | 0.250 | 0.077 | 1.38 | 0.224 |
| K6 | 0.164 | 1.67 | 0.393 | 0.029 | 0.75 | 0.155 |

Test samples were built with a representative vacuum lumen and camera wire to approximate the pressure drop and flow characteristics of a fully built device.

Flow rate can be determined by measuring the mass of water exiting the nozzle as a function of time. The experimental setup included a conventional saline irrigation bag under a certain pressure (for example, 2 psi or 4 psi) connected with the catheter and nozzle sections of the device. Table 3 shows the results of flow rate testing in grams per second for several nozzle arrangements.

TABLE 3

Mass flow rate for certain nozzle designs

| Design | Flow at 2 psi (g/s) | Flow at 4 psi (g/s) |
|---|---|---|
| K1 | 1.022 | 1.745 |
| K2 | 0.605 | 0.861 |
| K3 | 0.663 | 1.018 |

TABLE 3-continued

Mass flow rate for certain nozzle designs

| Design | Flow at 2 psi (g/s) | Flow at 4 psi (g/s) |
|---|---|---|
| K4 | 1.033 | 1.786 |
| K5 | 0.837 | 1.367 |
| K6 | 0.974 | 1.689 |
| L1 | 0.665 | 1.187 |
| L2 | 0.701 | 1.027 |
| L3 | 0.906 | 1.560 |
| L4 | 0.919 | 1.612 |

From empirical analysis of a range of nozzle designs including multiple irrigation ports, the preferred minimum irrigation mass flow rate from a saline bag at 2 psi is about 0.55 g/s and the preferred minimum irrigation mass flow rate from a saline bag at 4 psi is about 0.75 g/s. In a nozzle, each irrigation port contributes 1/N of the total mass flow rate, where N is the number of irrigation ports, and this fraction can be converted to a percentage. From empirical analysis of a range of nozzle designs with four irrigation ports, the various irrigation ports were measured as contributing between 15%-30% of the total irrigation mass flow rate as compared to the calculated amount of 25%. In some examples of the nozzle, the irrigation mass flow rate is substantially similar from each of the irrigation ports. In other examples of the nozzle, the irrigation mass flow can be between two and four times larger from some irrigation ports than from others. This asymmetry can be used advantageously to provide high irrigation mass flow in some directions from the nozzle.

Figure 63A:
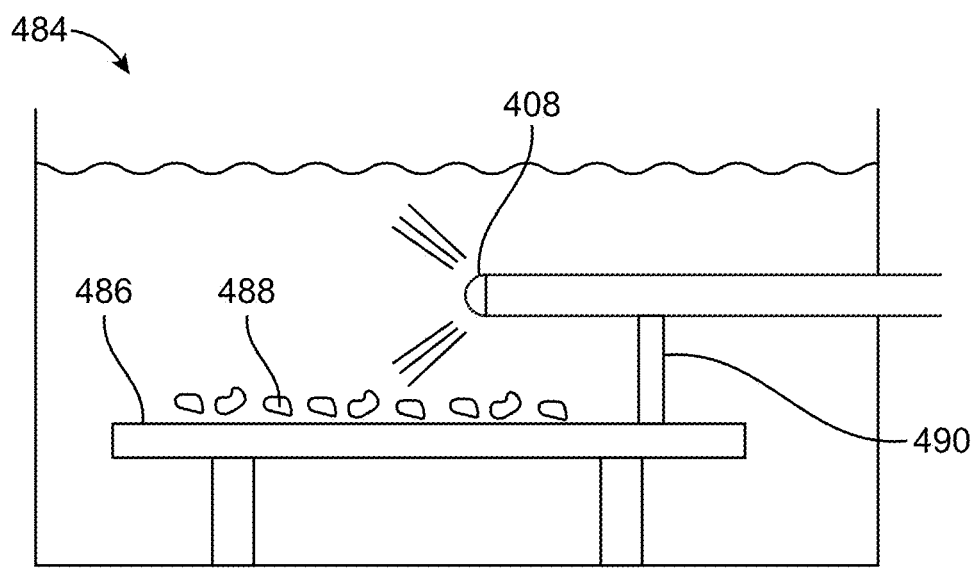
FIG. 63A illustrates a schematic of a test apparatus for measuring affected area of nozzle tip designs.
Figure 63B:
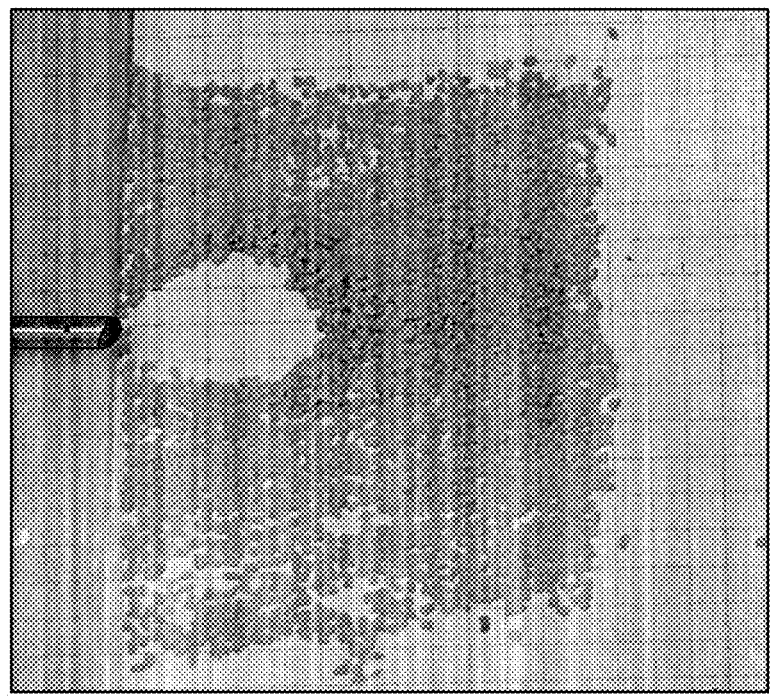
FIG. 63B is a photograph of test results when measuring affected area of nozzle tip designs.

The area affected by a nozzle design can be empirically determined. FIG. 63A illustrates a test apparatus 484 for determining affected area including a flat test surface 486 having a grid pattern onto which is spread a bed of kidney stone fragments 488 or simulated kidney stone fragments having a size range of from about 1.8 mm to 2.0 mm. A preferred test apparatus includes a bed of kidney stone fragments having substantially uniform sizes. The test apparatus includes a mount 490 for aligning the distal end of the device, including the nozzle 408, at a fixed distance above and parallel to the bed of kidney stones on the grid pattern. Using a pressurized saline bag, irrigation fluid is sent through the nozzle for a set time and the area affected by the fluid jetting from the nozzle is calculated using the grid pattern. Pressure on the saline bag can be in the range of from about 0.5 psi to about 6.0 psi. In some preferred examples the pressure on the saline bag is 2 psi or 4 psi. The nozzle is then rotated about its longitudinal axis by a fixed amount, the test is repeated, and the area affected by fluid is calculated. FIG. 63B shows a top view of a test bed after a test has been run. An area that is void of kidney stone fragments can be seen on the surface and the area can be measured using the grid pattern on the surface.

In preferred examples of the test, the nozzle is rotated 90 degrees such that the four test runs are able to approximate the three-dimensional volume affected by the irrigation port arrangement on the nozzle. Further, the distance of the nozzle above the grid surface can be changed to approximate a larger or smaller three-dimensional volume. In some preferred examples, the distance from the nozzle to the grid surface is about 6 mm. Table 4 shows the results of affected area testing in millimeters squared for several nozzle arrangements.

TABLE 4

Affected area for certain nozzle designs

| Design | Top (mm$^2$) | Bottom (mm$^2$) | Left (mm$^2$) | Right (mm$^2$) |
|---|---|---|---|---|
| K1 | 300 | 0 | 321 | 375 |
| K2 | 274 | 0 | 383 | 0 |
| K3 | 279 | 0 | 375 | 98 |
| K4 | 675 | 0 | 466 | 633 |
| K5 | 64 | 130 | 397 | 296 |
| L1 | 0 | 239 | 143 | 208 |
| L2 | 109 | 196 | 242 | 339 |
| L3 | 426 | 50 | 432 | 434 |
| L4 | 384 | 168 | 384 | 386 |

The grid surface test bed approximates a large volume that is open and effectively infinite as compared to anatomical scale cavities. Another test method can be used to approximate a closed system like the renal pelvis or the calyces of a kidney.

In one example of a closed system test apparatus, kidney stone fragments or simulated kidney stone fragments having a size range of from about 1.8 mm to 2.0 mm are placed into a test tube. The length and diameter of the test tube defines the volume of the test cavity. For example, a test tube having a 14 mm diameter and a 100 mm length can approximate a closed environment with an anatomically relevant scale. The test apparatus includes a fixture or mount for aligning the distal end of the device, including the nozzle, concentrically with the cross-section of the test tube. The distal end of the nozzle can be advanced and retracted with respect to the end of the test tube while irrigation fluid is applied at a given pressure. The extent of motion of the kidney stone fragments as a function of distance is measured. Table 5 shows the results of closed environment testing such that the distances in the table reflect the maximum distance from which a nozzle design can cause motion in stone fragments in the test apparatus when irrigation fluid is supplied at 2 psi.

TABLE 5

Fluidizing distance for certain nozzle designs

| Design | Distance (mm) |
|---|---|
| K1 | 19 |
| K3 | 20 |
| K4 | 22 |
| K5 | 16 |
| L1 | 24 |
| L2 | 15 |
| L3 | 22 |
| L4 | 22 |

Empirical testing of various nozzle configurations disclosure herein has demonstrated some preferred performance characteristics for the aspects of the method in which it is desirable to fluidize kidney stone fragments. The fluid velocity in some preferred examples is in the range of from about 0.50 m/s to about 1.50 m/s when the applied pressure is 2 psi and preferably is at least about 1.00 m/s. The fluid velocity in other preferred examples is in the range of from about 0.9 m/s to about 2.00 m/s when the applied pressure is 4 psi and preferably is at least about 1.45 m/s.

Figure 64:
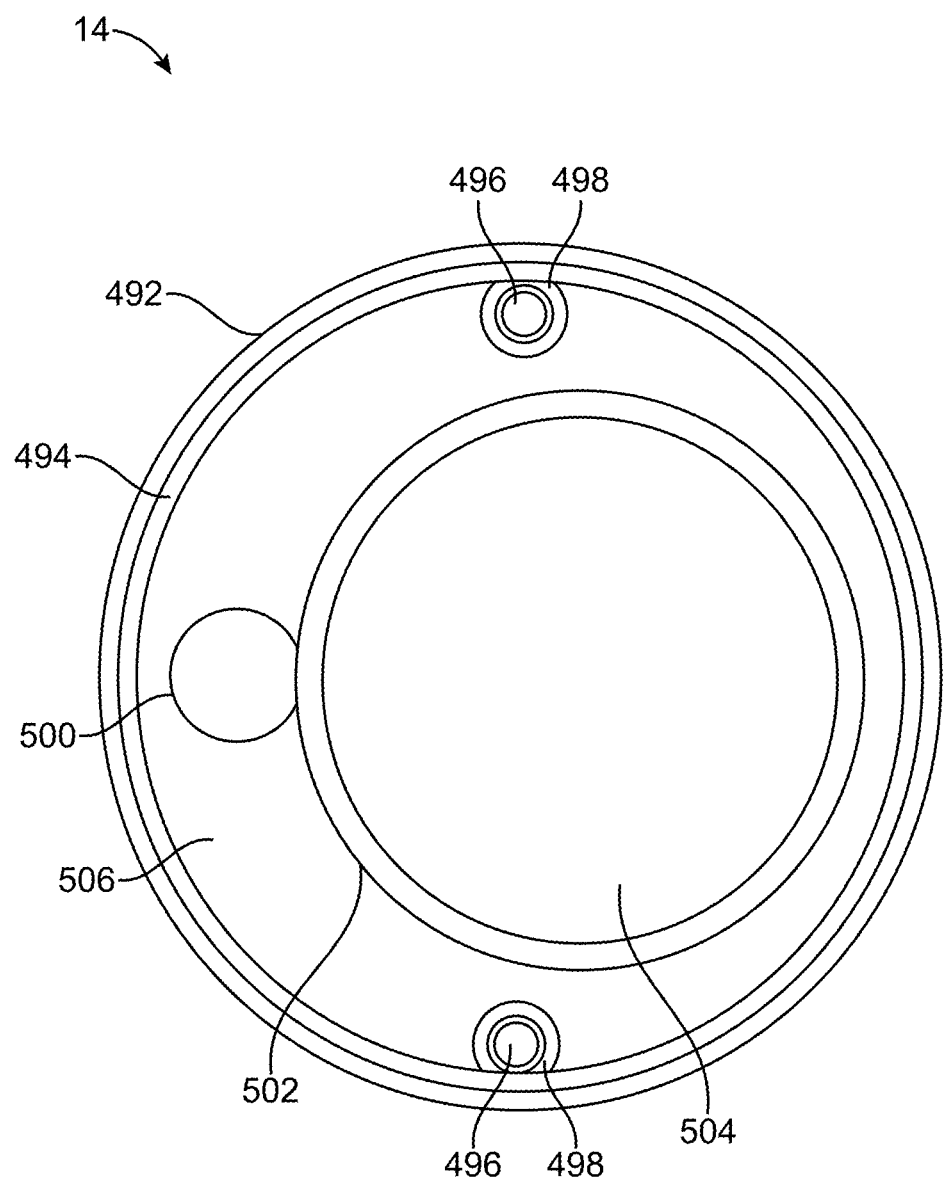
FIG. 64 illustrates a cross-sectional view of a section of the catheter shaft assembly.

FIG. 64 illustrates a cross-sectional view of a portion of a catheter 14. The outer member of the catheter 14 includes an outer jacket 492 and an outer hypotube 494. Within the outer member are pull wires 496 positioned within pull wire hypotubes 498 such that the pull wires 496 are free to slide longitudinally with respect to the pull wire hypotubes 498. In some examples, the pull wire hypotubes 498 can be fixed against the outer member and on opposite sides of the outer member. In other examples, the pull wire hypotubes 498 are fixed only at the distal end of the catheter 14. An electrical cable 500 is also within the outer member and connects the image sensor in the distal assembly with the handle. The electrical cable 500 is free to move within the outer member but is fixed at or near its distal and proximal ends within the outer member. A vacuum shaft 502 that encompasses a vacuum lumen 504 is also within the outer member and connects the vacuum lumen 504 defined by the nozzle tip with the handle 12. The vacuum shaft 502 is also free to move within the outer member but is fixed at or near its distal and proximal ends within the outer member. The remaining space within the outer member that is not occupied by the pull wire hypotubes 498, the electrical cable 500, or the vacuum shaft 502 is the irrigation space 506 through which irrigation fluid can flow from the handle to the conduits in the distal assembly. Because the electrical cable 500 and the vacuum shaft 502 are free to move within the outer member, the irrigation space 506 is not a fixed shape. One advantage of this arrangement is that there is no dedicated irrigation shaft, which decreases the number of structures within the catheter shaft assembly 14. Fewer structures results in ease of manufacture and increased flexibility in the catheter shaft assembly. For example, when the catheter shaft is generally straight, the irrigation space may take the general shape of an annulus between the outer member and the vacuum shaft but when the catheter shaft is curved the irrigation space may take the general shape of a crescent as the vacuum shaft is pressed against the inner wall of the outer member.

Tool Guiding Device

The above catheter advancements have provided the ability to combine the camera, laser, aspiration, and irrigation components into one system, to streamline kidney stone removal procedure and reduce the chances of adverse consequences associated with kidney stone treatment procedures, most particularly the need to repeat the insertion and removal of the ureteroscope and the extraction catheter to remove all of the stones. However, a challenge associated with catheter systems has been the inability to maintain a suitable catheter diameter. The consolidation of components, especially a laser, requires additional channels, which would make the catheter larger in profile than desired. Larger diameter catheters can cause more tissue irritation and injury when navigated thought the ureter, renal pelvis, and renal calyces. In some instances, a large diameter catheter may not be able to access the kidney at all because of a narrow and/or tortuous ureter. Accordingly, for maintaining a low catheter profile, existing lumens, such as the vacuum lumen (as described above), can be used for the laser and other tools. The use of the vacuum lumen is plausible because it is wide enough to accommodate a laser. Laser fibers have diameters smaller than vacuum lumens (the diameter of the vacuum lumen is much larger than the diameter of the working channel of traditional ureteroscope that receives the laser device). However, this significant difference in diameter causes the laser fiber to move within the vacuum lumen. Unwanted movement of the laser fiber prevents the clinician from being able to target stones with precision. Any side-to-side movement of the laser fiber in the vacuum lumen not only makes it difficult to fragmentize the stones, but also can increase the risk of the laser causing damage to nearby tissues. The embodiments of the tool guiding device provide a tool for allowing, inter alia, a laser to be effectively used with an extraction catheter system for fragmenting kidney stones while concomitantly allowing stones to flow past the laser and through the vacuum lumen.

A vacuum lumen (for e.g., lumen 404 and 504 as described above) of the catheter and nozzle can be used for insertion and retraction of stone fragmentation-inducing device such as a lithotripsy device or, most preferably, a laser lithotripsy device. An inner diameter of the inner tube or the diameter of the vacuum lumen (e.g., 404 and 504) needs to be large enough to accommodate passage of numerous stone fragments without clogging. In the embodiments of the present inventions, diameter of the vacuum lumen (e.g., 404 and 504) can be, for example, 2.0 mm to 3.0 mm, or in some configurations about 2.5 mm. Laser fibers and lithotripsy devices, however, have diameters considerably smaller than the vacuum lumen diameter. This significant difference in diameter causes the fragmentation-inducing device to move around or shift, during operation, within the vacuum lumen. The unintended movement of the laser makes it difficult for the physical to target stones with precision.

Figure 65:
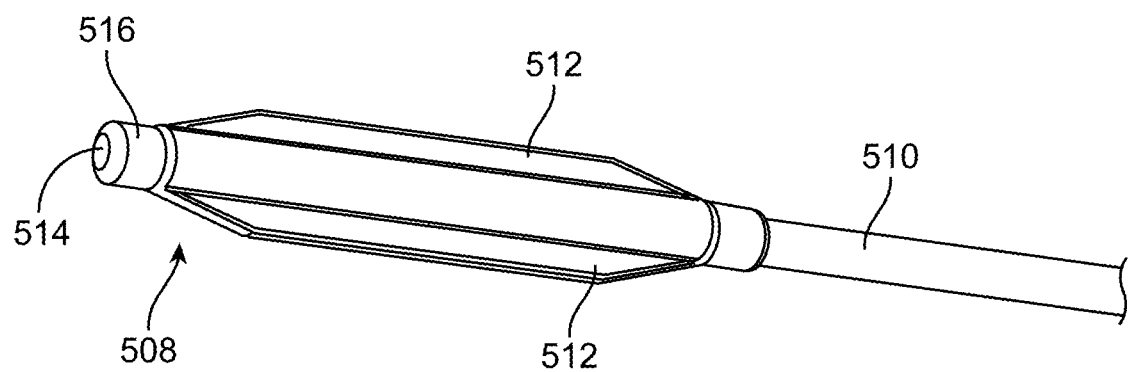
FIG. 65 is a partial perspective view of an embodiment of a guide.

Accordingly, the embodiments of the present inventions provide an intermediate device for securing the fragmentation-inducing device (preferably a laser device or fiber) into the vacuum lumen (e.g., 404 and 504). The intermediate device is configured to completely prevent or significantly minimize the movement of the laser fiber at the distal end of the vacuum lumen, while not impeding the functionality of the vacuum lumen and allowing fluid and solids to flow past the laser fiber. FIG. 65 illustrates the intermediate device, referring to herein as a guide 508. The guide 508 includes an elongated body or tube 510 that is configured to be inserted through a working channel (e.g., port 42 and 138) of the handle 12 and through a proximal end of the catheter 14, and pushed through the vacuum lumen (e.g., vacuum lumen 404 and 504) until a distal end of the guide 508 is positioned precisely at or approximately adjacent to the distal end of the vacuum lumen (e.g., at end of distal assembly 400 and nozzle tip 408). In one embodiment, the length of the guide 508 is equivalent to length the vacuum lumen in which it is to be placed. Preferably, the guide 508 is configured such that the distal tip of the guide 508 does not extend beyond the distal end opening of the vacuum lumen 404 (or nozzle tip 408) when the guide 508 is placed completely within the vacuum lumen or in operational position—that is, holding the laser tip at the distal end of the vacuum lumen 404 (or nozzle tip 408). The guide 508 includes at least 2 wings, ridges, flanges, or extensions 512, terms which are used herein interchangeably. The wings 512 project or extend out from a distal segment of the elongated body 510. In one embodiment, the wings 512 extend from the distal segment of the elongate body 510 such that when the elongated body 510 is placed at its operational position within the vacuum lumen 404, the wings 510 reside at the distal most segment of the vacuum lumen 404 of the nozzle tip 408. The wings 510 can be monolithic extensions of the elongated body 510—meaning, the body 510 and the wings 512 are made from or molded from one piece. Alternatively, the wings 512 can be extension of a smaller tube that is disposed over and attached to the distal segment of the elongated body 510. A lumen 514 extends though the center of the elongated body 510 for receiving the fragmentation-inducing device, preferably a laser fiber. The lumen 514 has a diameter for accommodating the laser fiber that is used. In other words, the dimeter of the lumen 514 is large enough to allow a laser fiber to be freely inserted therein and retracted therefrom, but small enough to prevent or significantly minimize any non-rotational or side-to-side movement of the laser fiber. The very distal end of the guide 508, in front of the wings 512, can include knob segment 516 having a tapered end of a smaller diameter than the elongated body 510. The knob segment 516 facilitates the insertion of the guide 508 into an access port of the handle 12 and vacuum lumen (e.g., 404 and 504). The vacuum lumen (e.g., 404 and 504) of the nozzle tip 408 can include a tapered segment (not illustrated). The knob segment 516 can come into contact against this smaller tapered end of the nozzle tip 408 to act as a stop and prevent the guide 508 from extending out from the vacuum lumen 404.

Figure 66:
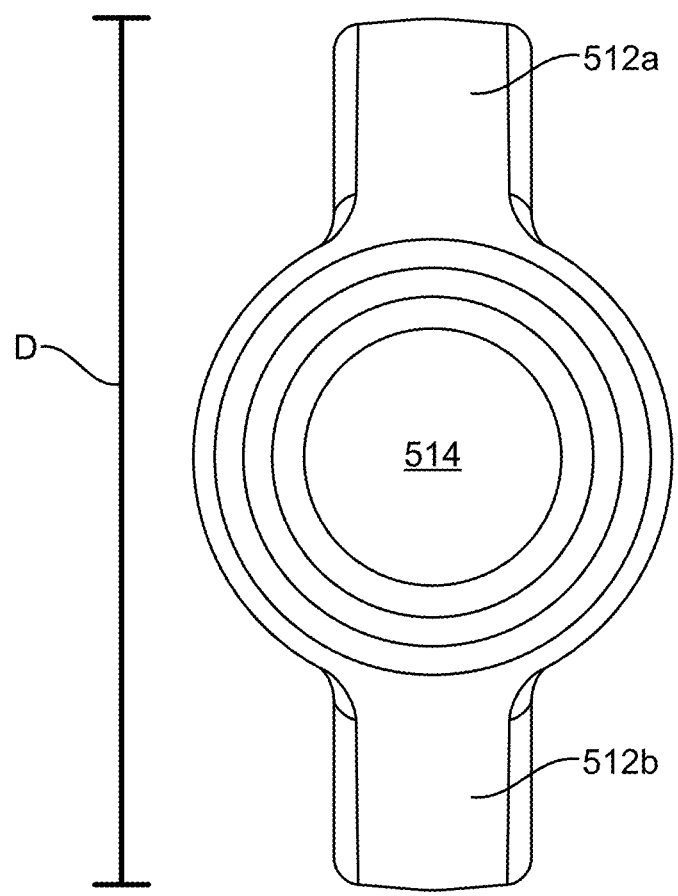
FIG. 66 is a front-end view of an embodiment of the guide.

FIG. 66 illustrates a front-end view of an embodiment of the guide 508. The guide includes (or consists of) two wings 512a and 512b extending from the elongated body 510. The wings 512a and 512b are sized to allow the guide 508 to freely glide into and out of the vacuum lumen (e.g., lumens 404 and 504, and nozzle lumen e.g., lumen 438), while preventing side-to-side or non-rotational movement of the winged-section of the guide 508 within the vacuum lumen (and nozzle lumen). In other words, the greatest diameter D of the guide 508, which includes the width (i.e., height) of the wings 512, should be slightly smaller than the inner diameter of the vacuum lumen to allow the wings 512 to traverse through the vacuum lumen, yet prevent significant side-to-side movement of the wings 512 within the vacuum lumen. In one embodiment, the diameter D can match or be about equal to the inner diameter of the vacuum lumen (e.g., vacuum lumen 404 of FIGS. 48A and 48B). Here, the wings 512 can be made from a softer or more pliable plastic material that allows the wings 512 to slightly compress when fitted through the vacuum lumen.

While a preferred two-wing design is illustrated in FIG. 66, the guide 508 can include (or consist of) three wings 512 or four wings 512. While the embodiments of the inventions can include any number of wings, a 2 to 4 wing design is preferred because a greater number of wings can cause stones to clog the vacuum lumen or be lodged between the vacuum lumen and the elongated body 510, thus encumbering the functionality of the vacuum lumen.

Figure 67:
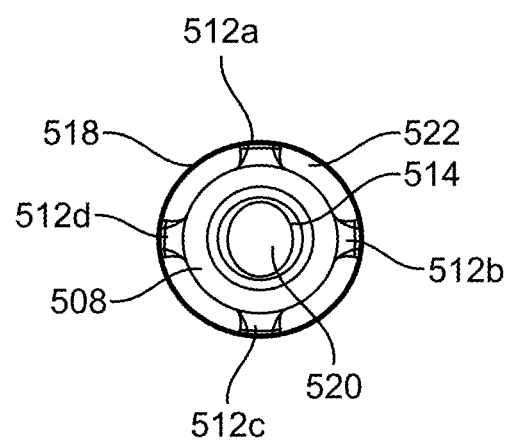
FIG. 67 is a schematic front-end view of an embodiment of the guide positioned inside of a vacuum tube.

FIG. 67 is a general schematic front-end view of the guide 508 comprising (or consisting of) four wings 512a-512d positioned at the distal most end of a vacuum tube 518 (or, for example, vacuum shaft 406 of FIGS. 48A and 48B) to secure a tip of a laser device or fiber at the distal tip of the vacuum tube 518. A laser device or fiber 520 is schematically shown positioned in the lumen 514 of the guide 508. The lumen's 514 restricted diameter, while allowing insertion and retraction of the laser fiber 520 through the guide 508, prevents or significantly minimizes movement of the laser fiber 520 within the vacuum tube 518 that is not intended by the physician. The stability of the laser 520 allows the physician to apply laser pulses to a kidney stone with great accurately, thus effectively fragmentizing the stones while reducing the risk of injury caused by deviated laser pulses. Wings 512a-512d should be of sufficient width or height (i.e., distance between the elongated body 510 and the vacuum tube 518) to create gaps 522 between the guide 508 and the vacuum tube 518. The gaps 522 allow the vacuum lumen to apply suction for removal of fluids, debris, and kidney stone fragments during the entire laser procedure. The number of wings 512 dictates the number of gaps 522. For example, two wings 512 provide two large gaps 522, three wings 512 provide three intermediate sized gaps 522, and the illustrated four-wing 512 configuration provides four smaller gaps 522. Larger gaps 522 are preferred to minimize the chances of stones becoming clogged or lodged at the entry point or along a distal section of the guide 508.

FIG. 67 shows four wings 512a-512d, where the circumferential distance is the same between any two neighboring wings. That is, the distance between each of 512a-512b, 512b-512c, 512c-512d, and 512d-512a is equal. In one embodiment, the circumferential distance between two neighboring wings can be different from the distance of another pair of neighboring wings (even if there is one shared wing). For example, the distance between neighboring wings 512a-512b and 512c-512d can be the same and the distance between 512a-512d and 512b-512c can be the same, but the distance between 512a-512b or 512d-512c is less than the distance between 512a-512d or 512b-512c. This configuration provides two small gaps 522 to allow passage of smaller stones and two large gaps 522 to allow passage of larger stones that may not have been able to be removed if the gaps 522 where the same size. In a three-wing configuration, the distance between each wing can vary, thus provided three gaps 522 each having a different size. Alternatively, in a three-wing configuration, the distance between two pairs of the neighboring wings can be the same while the third pair is spaced at a different distance. In some embodiments, in lieu or in addition to changing the distance between the wings 512 to vary the size of the gaps 522, widths (distance between the elongated tube 510 and vacuum lumen 518) of the wings can vary so provide gaps 522 of different sizes. By provided wings 512 having different widths, the position of the laser head will be shifted relative to the center of the vacuum lumen. Accordingly, in some embodiments, at least two different sized gaps 522 can be provided.

Figure 68:
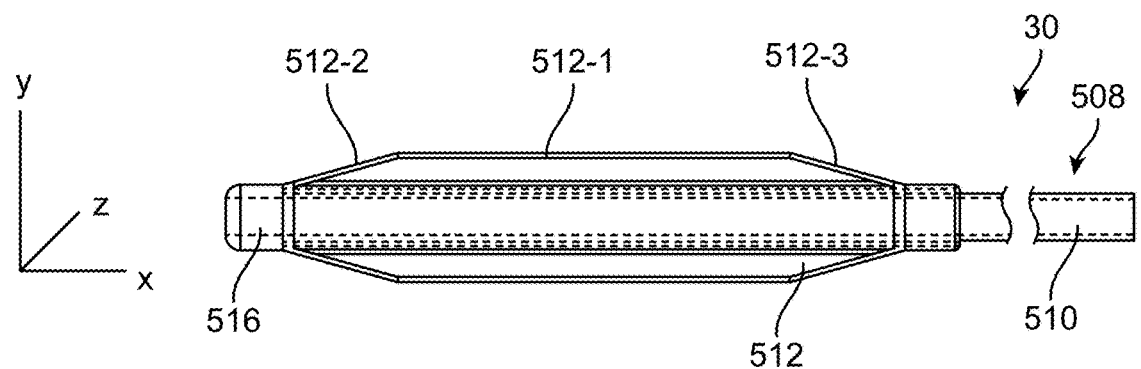
FIG. 68 is a schematic view of a distal section of an embodiment of the guide.
Figure 69A:
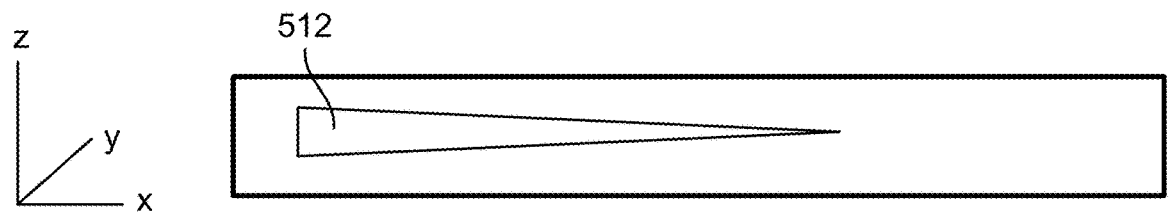
FIGS. 69A and 69B are top plan views illustrating various embodiments of wings or extensions for the guide.
Figure 69B:
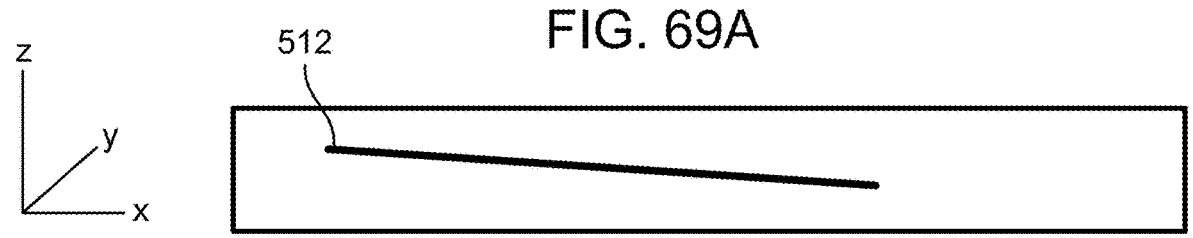

FIG. 68 is an embodiment of the wing 512 design. The wing 512 includes a middle section 512-1 extending into a distal 512-2 and proximal 512-3 segments. The length (in the x-direction, i.e., along the longitudinal axis) of the middle section 512-1 is greater than the length of the distal 512-2 and proximal 512-3 segments. The middle section 512-1 can have a constant width (in the y-direction, i.e., along the radial axis). The middle section 512-1 can have a rectangular shape, which allows it to have sufficient surface contact with an inner side of the vacuum lumen to create stability and prevent any unintended shifting of the guide's 508 distal end, where the wings 512 are located. The distal 512-2 and proximal 512-3 segments of the wing 34 slope or taper from the middle section 512-1 to the elongated tube 32. The thickness (in the z-direction) of the wing 512 can be the same along its entire span. In an alternative embodiment, the thickness (in the z-direction) of the wing 512 can vary so that the wing 512 is tapered along the x- or longitudinal direction. For example, as best illustrated in FIG. 69A, the wing 512 can have its thickest dimension at its leading, distal end and its thinnest dimension in its proximal end. In one embodiment, the sidewalls of the wing 512 can converge at an angle, as is shown in FIG. 69A, to provide the wing 512 with a shape of an isosceles triangle when viewed from the top. In accordance with another embodiment, as illustrated in FIG. 69B, the longitudinal axis of the wing 512 is not aligned with the longitudinal x-axis of the guide 508. The longitudinal axis of the wing 512 is rotated with respect to the x-axis of the guide 508. In accordance with another embodiment, not illustrated, the wings 512 can have a radius of curvature long the longitudinal direction. The wings 512 can be positioned symmetrically around the elongated body or tube 510, or alternatively, the wings 512 are positioned asymmetrically around the elongated body or tube 510.

Figure 70:
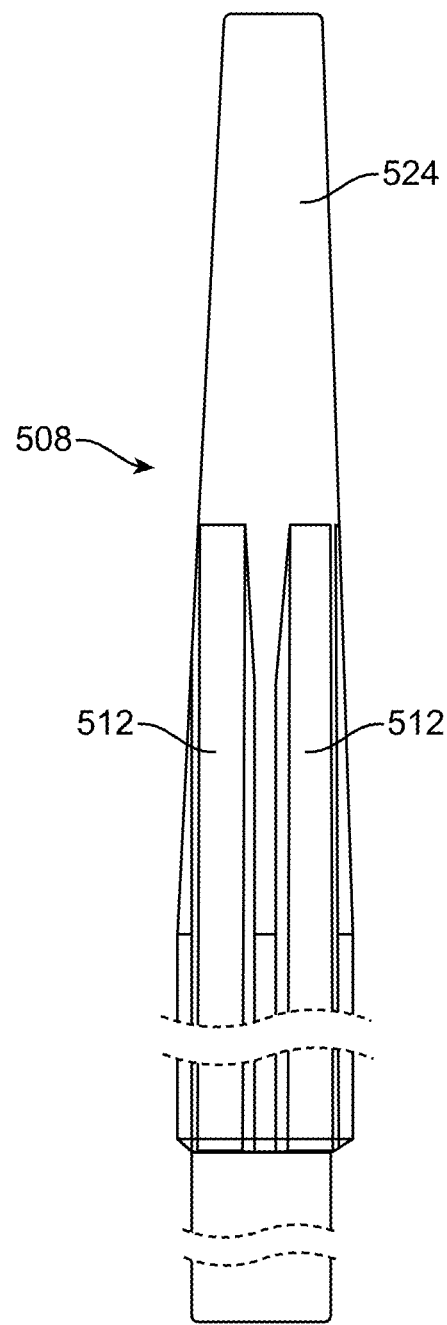
FIG. 70 is a partial side plan view of an embodiment of the guide.

FIG. 70 illustrates another embodiment of the guide 508. The guide 508 includes a distal end section 524 that is configured to extend out of the vacuum lumen (e.g., lumen 404 and 438 or nozzle tip 408) when the guide 30 is placed in position. The distal end section 524 can be a soft tip, for example. The wings 512 are positioned proximal to the distal end section 524 but are intended to reside at the distal end segment of the vacuum tube.

Figure 71A:
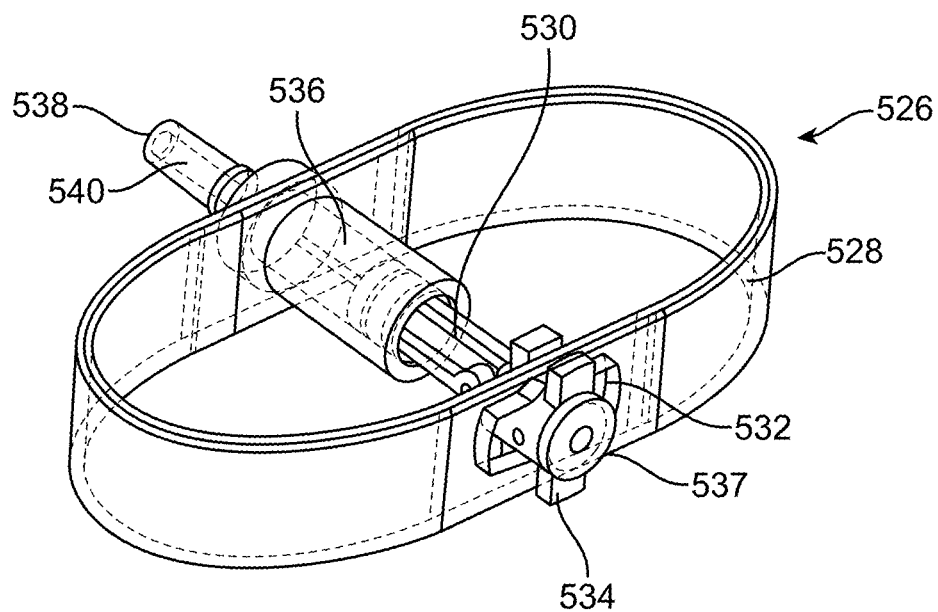
FIG. 71A is a perspective view of an embodiment of an actuator to actuate the guide.
Figure 71B:
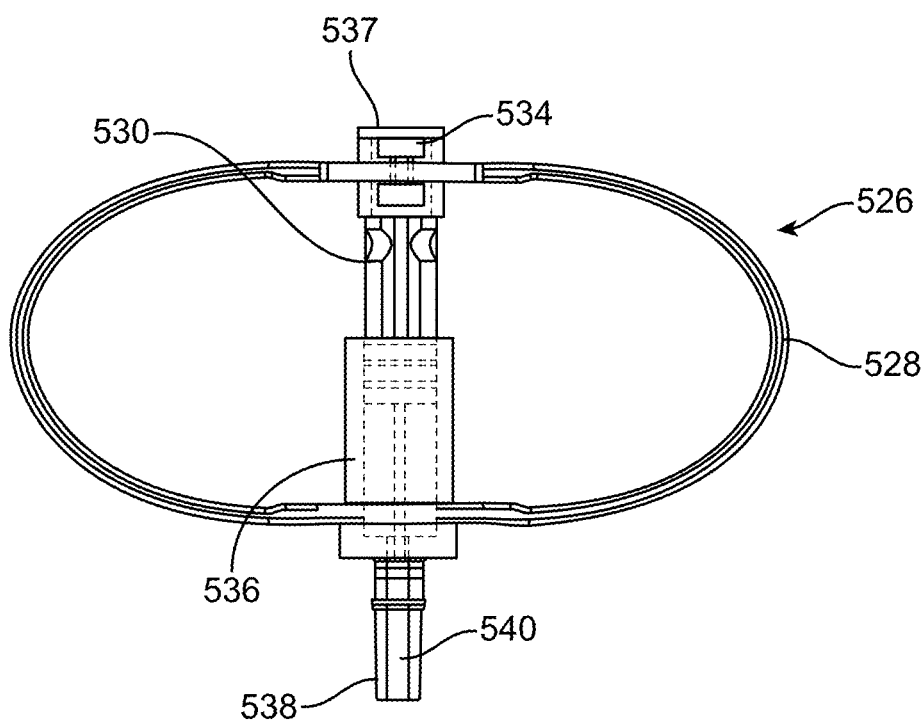
FIG. 71B is a top plan view of an embodiment of the actuator.

The guide 508 fixedly supports the head of the laser fiber at the distal tip of a vacuum lumen or nozzle tip while allowing the vacuum lumen to aspirate stones, debris, and fluids during the laser procedure and concomitantly with the fragmentation of kidney stones. However, the presence of the guide 508 reduces the inner working diameter of the vacuum lumen. Thus, the guide 508 increases the chance of larger sized stones gathered and/or becoming lodged at the entry point of the vacuum lumen, as well as in the gaps 522 or between the wings 512. Such clogging can reduce evacuation efficiency and require manual debris clearance or increasing internal pressures. The flow indicator 322 of handle 12 (as described above) can provide feedback to a user of clogging and reduction in evacuation. Accordingly, a device can be used to cause back-and-forth movement, vibration, or oscillation of the guide 508 to clear or extricate lodged or clogged stones. Minor back-and-forth movement of the guide 508 can be effective at dislodging debris and clearing the vacuum lumen. In accordance with one embodiment, as illustrated in FIGS. 71A and 71B, an actuator 526 is provided that can be permanently attached to or removable coupled with the guide 508. The actuator 526 can include a biasing band 528. The biasing band 528 is a self-resetting body, such that the inward compression (i.e., squeezing) and release of the band 528 can cause the back-and-forth movement of the guide 508 and the wings 512 within the vacuum lumen (for e.g., lumen 404 and 438). A shaft 530 has one end penetrating through a hole 532 of the band 528. The shaft 530 can be fixedly secured to the band 528 by two pairs of opposing tabs 534 extending from the shaft 530. A cylindrical housing 536 receives an opposing end of the shaft 530. The shaft 530 can move telescopically, back-and-forth, within the cylindrical housing 536 when the band 528 is compressed and released. The cylindrical housing 536 is coupled to the opposing side of the band 528 to which the shaft 530 is coupled. The shaft 530 can include a shaft head 537 that can be permanently attached to a proximal tail of the guide 508, or alternatively, the shaft head 537 can be configured to be able to be removably coupled to the proximal tail of the guide 508. For example, the shaft head 537 and the proximal tail of the guide 508 can have female/male coupling members. A tubular member 538 can extend from the proximal end of the cylindrical housing 536. The member 538 can be configured to connect to and disconnect from a handle (e.g., handle 12 described above) of a catheter. An access channel 540 can extend from the member 538, the cylinder housing 536, and the shaft 530 and communicate with the lumen 514 of the guide 508. The laser fiber can be inserted into the inlet opening of the access channel 540, fed through the actuator 526, and inserted into the lumen 514 of the guide 508. The laser fiber can be pushed through the lumen 514 of the guide 508 until the laser's head reaches the distal tip of the vacuum lumen (or nozzle tip), where wings 512 of the guide 508 prevent any unintended movement of the laser's head.

Figure 72:
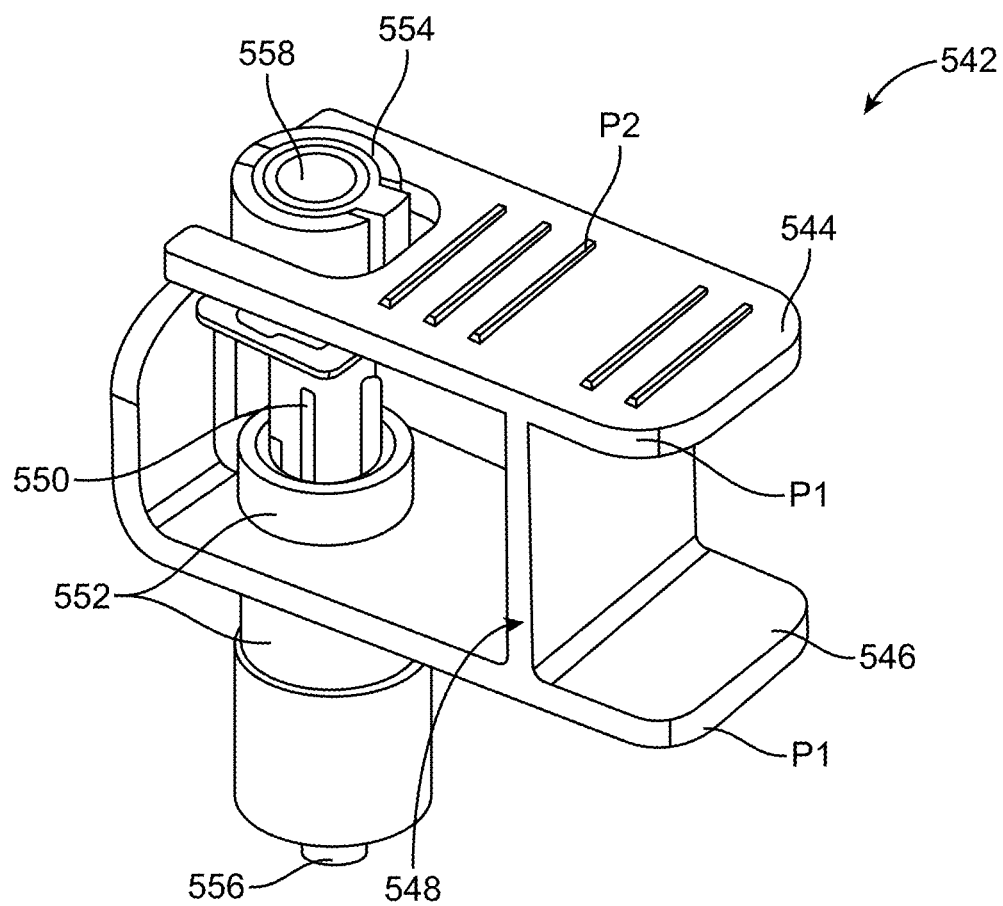
FIG. 72 is a perspective view of an embodiment of the actuator.

FIG. 72 illustrates another embodiment of an actuator 542. The actuator 542 can be permanently attached to or removably coupled with the guide 508. The actuator 542 can include a first (or as oriented in the figure, an upper or distal) lever 544 coupled to a second (or lower or proximal) lever 546 via a fulcrum bar 548. The actuator 542 is self-resetting, such that the inward compression (i.e., squeezing) and release of levers 544 and/or 546 can cause the back- and forth movement of the guide 508 and the wings 512 within the vacuum lumen (for example, lumen 404 and 428). A shaft 550 is coupled to the upper lever 544 and extends out of an opening of the upper lever 544. A cylindrical housing 552 receives an opposing end of the shaft 550. The shaft 550 can move telescopically, back-and-forth, within the cylindrical housing 552 when levers 554 and/or 546 are compressed and released. The cylindrical housing 552 is coupled to the lower lever 546. The shaft 550 includes a shaft head 554 that can be permanently attached to a proximal tail of the guide 508, or alternatively, the shaft head 554 can be configured to be able to be removably coupled to the proximal tail of the guide 508. For example, the shaft head 554 and the proximal tail of the guide 508 can have female/male coupling members. A tubular member 556 can extend from the proximal end of the cylindrical housing 552. The tubular member 556 can be configured to connect to and disconnect from a handle (e.g., handle 12 described above) of a catheter. A channel 558 is accessible from the member 556, and can extend from the member 558, the cylindrical housing 552, and the shaft 550, and communicate with the lumen 514 of the guide 508. The laser fiber can be inserted into the inlet opening of the access channel 558, fed through the actuator 542, and inserted into the lumen 514 of the guide 508. The laser fiber can be pushed through the lumen 514 of the guide 508 until the laser's head reaches the distal tip of the vacuum lumen or nozzle tip, where the wings 512 of the guide 508 prevent any unintended movement of the laser fiber's head. In operation, if the actuator 542 is squeezed inward at position P1 (e.g., the upper lever 554 and lower lever 546 are pinched towards each other), the shaft 550 actuates outwards (upwards in the illustration) and away from the lower lever 546). Here, the upper lever 544 and/or lower lever 546 pivot about the fulcrum arm 548 to create a wider gap between the levers 544/546 at the shaft end of the actuator 542 and a smaller gap between the levers 544/546 at the end labeled position P1. If the actuator 542 is squeezed inward at position P2, (e.g., the upper lever 554 and lower lever 546 are pinched towards each other or the upper lever 554 is pushed downwards towards the lower lever 546), the shaft 550 actuates inwards (downwards in the illustration) and towards the lower lever 546). Here, the upper lever 544 and/or lower lever 546 pivot about the fulcrum arm 548 to create a smaller gap between the levers 544/546 at the shaft end of the actuator 542 and a wider gap between the levers 544/546 at the end labeled position P1. Thus, the movement of the shaft head 554 can be either away from or towards the lower lever 546 based on the force that is applied either at P1 or P2.

For the treatment of kidney stones, the catheter can be directed into the kidney with a use of guidewire. The guide 508 can be inserted into the vacuum lumen before the insertion of the catheter into the patient. The lumen 514 of the guide 508 can be used to receive the guidewire for navigating the catheter over the guidewire. Alternatively, the guide 508 can be inserted into the catheter at any time during the procedure, including when the catheter has reached its intended position. If a guidewire is with the lumen 514, the guidewire is removed followed by insertion of the laser fiber. The laser fiber is directed through the lumen 514 of the guide 508 until the laser's head reaches the end of the knob 516. A physician can apply laser pulses to kidney stones concomitantly with aspirating debris, stones, and fluids through the catheter and nozzle vacuum lumen. Should any stones become lodged at the opening of the guide 508, the actuator 526 or 542 can be used to move the guide 508 within the vacuum lumen to dislodge the stones. After the laser procedure, the guide 508 can be removed and the vacuum lumen can be used for the extraction of the remaining un-fragmented or fragmented stones for the treatment of kidney stones.

The various examples, aspects, and embodiments of the kidney stone removal systems disclosed herein provide various advantages when used to treat kidney stones. One advantage is the ability to prevent or to mitigate the possibility of overpressurizing the kidney during kidney stone treatment. In conventional laser lithotripsy of kidney stones, irrigation fluid can be introduced during ureteroscopy and/or during laser lithotripsy. In most cases, the irrigation fluid can drain out of the kidney only via the narrow space between the ureteroscope and the access sheath. This narrow space can become narrowed further by debris such as kidney stone fragments, clots, or other substances. When the egress of fluid from the kidney is limited by such a narrow space, continued infusion of irrigation fluid creates the risk of high pressures in the kidney, which can cause sepsis and/or other complications. The kidney stone removal system disclosed herein provides a much larger egress channel via the large diameter vacuum lumen. Further, it is possible to apply vacuum through the large diameter vacuum lumen while introducing irrigation fluid. The large diameter of the vacuum lumen in combination with the ability to apply vacuum while delivering irrigation fluid significantly reduces the likelihood of overpressurizing the kidney, resulting in safer kidney stone removal procedures.

Another advantage of the kidney stone removal systems disclosed herein is the ability to prevent or mitigate thermal damage to the kidney during laser lithotripsy. Heat is generated within the kidney during laser lithotripsy of kidney stone, in particular with higher power lasers. This heat can be damaging to the kidney and is a concern for physicians when performing laser lithotripsy. Irrigation fluid can help dissipate the heat via conductive heat transfer, but as described herein irrigation fluid can also build up within the kidney if the pathway for draining is relatively narrow. The kidney stone removal system disclosed herein provides a much larger egress channel via the large diameter vacuum lumen in combination with the ability to apply vacuum while delivering irrigation fluid. The kidney stone removal system disclosed herein can maintain a safe temperature within the kidney by rapidly removing heated irrigation fluid from the kidney and introducing relatively cooler irrigation fluid in a continuous manner during laser lithotripsy. In the examples, aspects, and embodiments of the kidney stone removal system that include a laser guide, heated irrigation fluid can easily and rapidly flow through the vacuum lumen even while the laser fiber is being used to fragment kidney stones and comparatively cooler irrigation fluid can easily and rapidly enter the kidney via the irrigation ports on the nozzle. This rapid heat transfer via irrigation fluid rapidly introduced and removed from the kidney significantly reduces the likelihood of thermal damage to the kidney, resulting in safer kidney stone removal procedures.

Another advantage of the kidney stone removal systems disclosed herein is the ability to improve visibility in the kidney during laser lithotripsy. In conventional laser lithotripsy, debris from fragmenting kidney stones frequently obscures the view from the imaging portion of a ureteroscope and makes it difficult for a physician to see areas of interest within the kidney and/or the kidney stones being fragmented. Physicians often describe a "snow globe" effect during laser lithotripsy in which debris is ejected from the kidney stone in a random and chaotic manner that quickly fills their field of view. The kidney stone removal system disclosed herein can improve visibility by rapidly removing debris fluidized in the irrigation fluid from the kidney through the large diameter vacuum lumen and introducing clear irrigation fluid in a continuous manner during laser lithotripsy. In the examples, aspects, and embodiments of the kidney stone removal system that include a laser guide, debris suspended or fluidized in irrigation fluid can easily and rapidly flow through the vacuum lumen even while the laser fiber is being used to fragment kidney stones. Further, rather than a random and chaotic field of view, the kidney stone removal system disclosed herein provides a predictable pattern as debris moves in a regular motion across the field of view to the vacuum lumen. Such a regular pattern makes it easier for a physician to stay oriented with anatomical landmarks in the field of view. Still further, because of the comparatively large egress channel (as compared to the narrow channel between the ureteroscope and access sheath) more debris is removed and removed faster using the kidney stone removal system disclosed herein. In some cases, even with little or no applied vacuum the large diameter of the vacuum lumen creates sufficient passive outflow to substantially improve visibility. The large diameter of the vacuum lumen in combination with the ability to apply vacuum while delivering irrigation fluid and in combination with the regular debris flow pattern significantly improves visibility during laser lithotripsy, resulting in safer, more efficient, and more effective kidney stone removal procedures.

Another advantage of the kidney stone removal systems disclosed herein is the ability to rapidly apply and remove therapeutic or diagnostic agents in the kidney during laser lithotripsy. The irrigation fluid can have chemical or biological agents applied to it from the source bag or using a port adjacent to the system handle. These agents can be therapeutic, such as, but not limited to, hemostatic, antibiotic, and/or lytic agents. And these agents can be diagnostic, such as, but not limited to, contrast agents.

Another advantage of the kidney stone removal systems disclosed herein is the orientation of the irrigation ports with respect to the distal end of the vacuum lumen. The irrigation ports deliver irrigation fluid at a departure angle with respect to the central axis of the cross section of the vacuum lumen. This angle, in combination with the vacuum applied via the vacuum lumen, creates a flow pattern that affects a volume much larger than the diameter of the distal end of the device. And this flow pattern can be regular rather than turbulent and can reduce, mitigate, and/or eliminate vortices that can form when conventional ureteroscopes deliver fluid to a kidney. Further, it has been empirically shown that irrigation ports that deliver fluid in a straight line distally from the end of the ureteroscope tip can push debris away from the distal tip, which makes it difficult to aspirate the debris. In contrast, the kidney stone removal systems disclosed herein can bring debris closer to the vacuum lumen by producing regular flow patterns that initially diverge away from the nozzle and return back to the central axis of the nozzle at distance from the distal end of the nozzle. The kidney stone removal systems disclosed herein do not need to be pointed directly at kidney stone fragments to affect them and to bring them close to the vacuum lumen. Thus, the effective area of the kidney stone removal systems disclosed herein is significantly greater than the area directly in front of the nozzle and this effective area can be used to clear calyces of debris without the nozzle being pointed directly at the debris.

Another advantage of the kidney stone removal systems disclosed herein is that the irrigation ports can provide a flow rate independent of the tool being used within the vacuum lumen. Conventional ureteroscopes typically provide irrigation through the working channel and this same working channel is used to provide access for laser fibers or baskets. The presence of a tool within the working channel alters the fluid dynamics and changes the flow rate and other flow characteristics. In contrast, the kidney stone removal systems disclosed herein delivers irrigation fluid via dedicated irrigation ports such that the flow characteristics are independent of the tool being used, if any, in the vacuum lumen.

As used herein, connected, attached, coupled or in communication with are terms which can be used interchangeably and when a feature or element is referred to herein as being connected, attached, coupled or in communication with to another feature or element, it can be directly connected to the other feature or element or intervening features or elements may be present. In contrast, when a feature or element is referred to as being directly connected to another feature or element, there are no intervening features or elements present.

When a feature or element is referred to herein as being "on" another feature or element, it can be directly on the other feature or element or intervening features and/or elements may also be present. In contrast, when a feature or element is referred to as being directly on another feature or element, there are no intervening features or elements present.

Although the above descriptions refer to "embodiments," any one of the above-described features or embodiments can be use, implemented, or combined with any other of the features or embodiments described herewith.

As used herein, the singular forms "a", "an" and "the" are intended to include the plural forms as well, unless the context clearly indicates otherwise.

It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof.

As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

When a feature is said to be disposed "adjacent" another feature, it may be positioned next to the other feature without any overlapping or underling portions, or it may have portions that overlap or underlie the adjacent feature.

The spatially relative terms, "proximal," "distal," and the like, may be used herein for ease of description to describe one element's or feature's relationship to another. It will be understood that proximal describes a spatial location closer to the user or the intended position of the user while distal describe a location farther from the user or the intended position of the user. Further, when used with respect to a minimally invasive device like a catheter, proximal and distal locations refer to the portion of the device that is intended to be closer to or farther from the user, respectively, and do not change when the device is in use.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element could be termed a second feature/element, and similarly, a second feature/element could be termed a first feature/element without departing from the teachings of the present invention.

As used herein including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to the value," "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Disclosed herein are systems, devices, and methods for the guided removal of objects in vivo. In particular, the systems, devices, and methods may be adapted to traverse compact areas, such as the urinary tract, and to remove debris, such as kidney stones or fragments of kidney stones, via aspiration through a vacuum tube. As used herein, the term "kidney stones" may refer to fragments of kidney stones, including fragments that have been created by therapeutic fracturing of kidney stones, such as with the device described herein or by another device. The term "kidney stones" may refer to stone or fragments of stones located in the ureter as well as in the kidney and the systems, devices, and methods disclosed herein may be capable of removing kidney stones from the kidney or ureter.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived therefrom, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

It is understood that this disclosure, in many respects, is only illustrative of the numerous alternative device embodiments of the present invention. Changes may be made in the details, particularly in matters of shape, size, material and arrangement of various device components without exceeding the scope of the various embodiments of the invention. Those skilled in the art will appreciate that the exemplary embodiments and descriptions thereof are merely illustrative of the invention as a whole. While several principles of the invention are made clear in the exemplary embodiments described above, those skilled in the art will appreciate that modifications of the structure, arrangement, proportions, elements, materials and methods of use, may be utilized in the practice of the invention, and otherwise, which are particularly adapted to specific environments and operative requirements without departing from the scope of the invention. In addition, while certain features and elements have been described in connection with particular embodiments, those skilled in the art will appreciate that those features and elements can be combined with the other embodiments disclosed herein.

What is claimed is:

1. A kidney stone removal mechanism comprising:
    an irrigation tube configured to transport a volume of an irrigation fluid supplied through an inlet, the irrigation tube having a portion passing within and contactable with a trigger mechanism through which a first amount of the volume of the irrigation fluid passes; and
    a bypass structure connected at only two places with the irrigation tube and configured to receive a second amount of the volume of the irrigation fluid and to allow the second amount of the volume of the irrigation fluid to be transported through a first part of the irrigation tube and transferred through a second part of the irrigation tube to be discharged from an outlet without any of the second amount of the volume of the irrigation fluid passing through the portion of the irrigation tube passing within and contactable with the trigger mechanism,
    wherein the first amount of the volume of irrigation fluid bypasses the bypass structure; and
    wherein the trigger mechanism includes a trigger operable by a user, the trigger mechanism operable to selectively constrict, close, and open the irrigation tube to irrigate an area of treatment upon user operation of the trigger.

2. The kidney stone removal mechanism of claim 1, wherein
    the irrigation tube is one continuous passageway that connects the inlet to the outlet and extends from the first part of the irrigation tube to the second part of the irrigation tube, and has a middle segment between the first part and the second part of the irrigation tube passing within and contactable with the trigger mechanism; and
    the bypass structure which is connected at only two places with the irrigation tube has a first end opening connected to the first part of the irrigation tube and a second end opening connected to the second part of the irrigation tube to allow the second amount of the volume of the irrigation fluid being transported through the first part of the irrigation tube and transferred to the second part of the irrigation tube to be discharged from the outlet without any of the second amount of the volume of the irrigation fluid passing through the middle segment of the irrigation tube passing within and contactable with the trigger mechanism.

3. The kidney stone removal mechanism of claim 1, wherein the bypass structure comprises a flow restriction.

4. The kidney stone removal mechanism of claim 1, wherein user depression of the trigger progressively opens the irrigation tube.

5. The kidney stone removal mechanism of claim 1, further comprising a vacuum tube configured to be activated by the operation of the trigger mechanism, wherein the operation of the trigger mechanism concurrently opens the irrigation tube.

6. The kidney stone removal mechanism of claim 1, further comprising:
    a catheter connected at a proximal end of the catheter to a distal end of the kidney stone removal mechanism, the catheter having a distal tip at a distal end of the catheter; and
    a steering mechanism, located at a proximal end of the kidney stone removal mechanism, the steering mechanism operable to steer the distal tip to facilitate removal of partial or entire kidney stones.

7. A kidney stone removal mechanism comprising:
    an irrigation tube configured to transport irrigation fluid, the irrigation tube having a portion passing within and contactable with a trigger mechanism; and
    a bypass structure having a first end opening connected to a first part of the irrigation tube and a second end opening connected to a second part of the irrigation tube, the bypass structure configured to allow a volume of the irrigation fluid supplied through an inlet to be transported from the first part of the irrigation tube to the second part of the irrigation tube to be discharged from an outlet without allowing any of the volume of the irrigation fluid passing through the bypass structure to be diverted to the portion of the irrigation tube passing within and contactable with the trigger mechanism;
    wherein the trigger mechanism includes a trigger operable by a user, the trigger mechanism operable to selectively constrict, close, and open the irrigation tube to irrigate an area of treatment upon user operation of the trigger, wherein
    the irrigation tube is one continuous passageway that connects the inlet to the outlet and extends from the first part of the irrigation tube to the second part of the irrigation tube, and has a middle segment between the first part and the second part of the irrigation tube passing within and contactable with the trigger mechanism; and
    wherein the bypass structure which is connected at only two places with the irrigation tube has the first end opening connected to the first part of the irrigation tube and the second end opening connected to the second part of the irrigation tube to allow the volume of the irrigation fluid being transported through the first part of the irrigation tube and transferred to the second part of the irrigation tube to be discharged from the outlet without allowing any of the volume of the irrigation fluid passing through the bypass structure to be diverted to the middle segment of the irrigation tube passing within and contactable with the trigger mechanism.

* * * * *